(12) United States Patent
Mukerji et al.

(10) Patent No.: US 7,067,285 B2
(45) Date of Patent: *Jun. 27, 2006

(54) DESATURASE GENES AND USES THEREOF

(75) Inventors: Pradip Mukerji, Gahanna, OH (US); Yung-Sheng Huang, Upper Arlington, OH (US); Tapas Das, Worthington, OH (US); Jennifer Thurmond, Columbus, OH (US); Amanda Eun-Yeong Leonard, Columbus, OH (US); Suzette L. Pereira, Westerville, OH (US)

(73) Assignee: Abbott Laboratories, Abbott Park, IL (US)

( * ) Notice: Subject to any disclaimer, the term of this patent is extended or adjusted under 35 U.S.C. 154(b) by 29 days.

This patent is subject to a terminal disclaimer.

(21) Appl. No.: 10/054,534

(22) Filed: Jan. 22, 2002

(65) Prior Publication Data

US 2003/0167525 A1 Sep. 4, 2003

Related U.S. Application Data

(63) Continuation-in-part of application No. 09/769,863, filed on Jan. 25, 2001, now Pat. No. 6,635,451.

(51) Int. Cl.
C12P 21/02 (2006.01)
C07H 21/04 (2006.01)
C07H 15/11 (2006.01)
C12N 15/74 (2006.01)
A01N 63/04 (2006.01)

(52) U.S. Cl. .................. 435/71.1; 435/325; 435/320.1; 435/254.11; 435/189; 536/23.1; 536/23.2; 800/8; 424/93.21

(58) Field of Classification Search ............... 536/23.1, 536/23.2; 800/8; 435/325, 320.1, 254.11, 435/71.1, 189; 424/93.21
See application file for complete search history.

(56) References Cited

U.S. PATENT DOCUMENTS

| | | | |
|---|---|---|---|
| 4,582,788 A | 4/1986 | Erlich | 435/6 |
| 4,666,701 A | 5/1987 | Horrobin et al. | 514/558 |
| 4,683,194 A | 7/1987 | Saiki et al. | 435/6 |
| 4,683,202 A | 7/1987 | Mullis | 435/91.2 |
| 4,758,592 A | 7/1988 | Horrobin et al. | 514/549 |
| 4,826,877 A | 5/1989 | Stewart et al. | 514/560 |
| 4,943,674 A | 7/1990 | Houck et al. | 800/287 |
| 4,945,050 A | 7/1990 | Sanford et al. | 435/459 |
| 5,004,863 A | 4/1991 | Umbeck | 800/314 |
| 5,106,739 A | 4/1992 | Comai et al. | 800/294 |
| 5,107,065 A | 4/1992 | Shewmaker et al. | 800/29 |
| 5,116,871 A | 5/1992 | Horrobin et al. | 514/560 |
| 5,159,135 A | 10/1992 | Umbeck | 800/314 |
| 5,175,095 A | 12/1992 | Martineau et al. | 435/69.1 |
| 5,188,958 A | 2/1993 | Moloney et al. | 800/300 |
| 5,231,020 A | 7/1993 | Jorgensen et al. | 800/281 |
| 5,416,011 A | 5/1995 | Hinchee et al. | 800/294 |
| 5,420,034 A | 5/1995 | Kridl et al. | 435/419 |
| 5,447,974 A | 9/1995 | Peng | 523/415 |
| 5,463,174 A | 10/1995 | Moloney et al. | 800/294 |
| 5,518,908 A | 5/1996 | Corbin et al. | 800/279 |
| 5,552,306 A | 9/1996 | Thomas et al. | 435/134 |
| 5,569,834 A | 10/1996 | Hinchee et al. | 800/312 |
| 5,589,379 A | 12/1996 | Kridl et al. | 435/419 |
| 5,631,152 A | 5/1997 | Fry et al. | 800/268 |
| 5,700,671 A | 12/1997 | Prieto et al. | 800/25 |
| 5,750,176 A | 5/1998 | Prieto et al. | 426/580 |
| 5,912,120 A | 6/1999 | Goldstein et al. | 435/6 |
| 5,972,664 A | 10/1999 | Knutzon et al. | 435/136 |
| 2002/0156254 A1 * | 10/2002 | Qiu et al. | 536/23.1 |

FOREIGN PATENT DOCUMENTS

| | | |
|---|---|---|
| EP | 050424 | 9/1985 |
| EP | 084796 | 5/1990 |
| EP | 201184 | 12/1992 |
| EP | 258017 | 4/1997 |
| EP | 237362 | 10/1998 |
| EP | 1035207 A | 9/2000 |
| WO | WO 93/06712 A | 4/1993 |
| WO | WO 93/11245 | 6/1993 |
| WO | WO 94/11516 | 5/1994 |
| WO | WO 95/24494 | 9/1995 |
| WO | WO 96/13591 | 5/1996 |
| WO | WO 99/61602 A | 12/1999 |

(Continued)

OTHER PUBLICATIONS

Kelder et al. Expression of fungal desaturase genes in cultured mammalian cells. Mol Cell Biochem. Mar. 2001;219(1-2):7-11.*

(Continued)

*Primary Examiner*—David Guzo
*Assistant Examiner*—Daniel M. Sullivan
(74) *Attorney, Agent, or Firm*—Cheryl L. Becker

(57) ABSTRACT

The subject invention relates to the identification of genes involved in the desaturation of polyunsaturated fatty acids at carbon 5 (i.e., "Δ5-desaturase") and at carbon 6 (i.e., "Δ6-desaturase") and to uses thereof. In particular, Δ5-desaturase may be utilized, for example, in the conversion of dihomo-γ-linolenic acid (DGLA) to arachidonic acid (AA) and in the conversion of 20:4n-3 to eicosapentaenoic acid (EPA). Delta-6 desaturase may be used, for example, in the conversion of linoleic (LA) to γ-linolenic acid (GLA). AA or polyunsaturated fatty acids produced therefrom may be added to pharmaceutical compositions, nutritional compositions, animal feeds, as well as other products such as cosmetics.

16 Claims, 15 Drawing Sheets

FOREIGN PATENT DOCUMENTS

| WO | WO 00/20603 A | 4/2000 |
|----|---------------|--------|
| WO | WO 00/0075341 | 12/2000 |
| WO | WO 02/26946   | 4/2002 |

OTHER PUBLICATIONS

Houdebine LM. Transgenic animal bioreactors. Transgenic Res. 2000;9(4-5):305-20.*

Richards FM. Protein stability: still an unsolved problem. Cell Mol Life Sci. Oct. 1997;53(10):790-802.*

Qiu, Xiao, et al., "Identification of a DELTA4 Fatty Acid Desaturase from *Thraustochytrium* sp. Involved in the Biosynthesis of Docosahexanoic Acid by Hetrologous Expression in *Saccharomyces cerevisia* and *Brassica juncea*," *Journal of Biological Chemistry*, vol. 276, No. 34, (Aug. 24, 2001) pp. 31561-31566.

Saito, Tamao and Ochia, Hiroshi, "Identification of DELTA5-Fatty Acid Desaturase from the Cellular Slime Mold Dictyostelium Discoideum," *Eur. J. Biochem.*, vol. 265, (1999), pp. 809-814.

Leonard, Amanda E., et al., "cDNA Cloning and Characterization of Human DELTA5-Desaturase Involved in the Biosynthesis of Arachidonic Acid," *Biochem J.*, vol. 347, (2000), pp. 719-724.

Cho, Hyekyung P., et al., "Cloning, Expression, and Fatty Acid Regulations of the Human DELTA-5 Desaturase," *The Journal of Biological Chemistry*, vol 274, No. 52, (Dec. 24, 1999) pp. 37335-37339.

Sakuradani, Eiji, et al., "DELTA6-Fatty Acid Desaturase from and Arachidonic Acid-Producing *Mortierella* Fungus Gene Cloning and its Heterologous Expression in a Fungus, *Aspergillus*," *GENE: An International Journal on Genes and Genomes*, vol. 238, No. 2, (1999), pp. 445-453.

Huang, Yung-Sheng, et al., "Cloning of DELTA12- and DELTA6-Desaturases from *Mortierella alpina* and Recombinant Production of GAMMA-Linolenic Acid in *Saccharomyces cerevisiae*," *Lipids*, vol. 34, No. 7, (Jul. 1999), pp. 649-659.

Alonso, D. Lopez, et al., "Plants as 'Chemical Factories' for the Production of Polyunsaturated Fatty Acids," *Biotechnology Advances*, vol. 18, (2000), pp. 481-497.

*The Faseb Journal, Abstracts, Part I*, Abstract 3093, p. A532, Experimental Biology 98, San Francisco, CA (Apr. 18-22, 1998).

Altschul, et al., *Nucleic Acids Research*, Gapped Blast and PSI-Blast: A New Generation of Protein Database Search Programs, 25: 3389-3402 (1997).

Okamuro & Goldberg, *Biochemistry of Plants*, Regulation of Plant Gene Expression: General Principles, 15:1-82 (1989).

Turner & Foster, *Molecular Biotechnology*, The Potential Exploitation of Plant Viral Translational Enhancers in Biotechnology for Increased Gene Expression, 3:225 (1995).

Ingelbrecht, et al., *Plant Cell*, Different 3' End Regions Strongly Influence the Level of Gene Expression in Plant Cells, 1:671-680 (1989).

Klein, et al, *Nature (London)*, High-Velocity Microprojectiles for Delivering Nucleic Acids Into Living Cells, 327:70-73 (1987).

Ishida Y., et al., *Nature Biotech*, High Efficiency Transformation of Maize (*Zea mays* L.) Mediated by *Agrobacterium tumefaciens*, 14:745-750 (1996).

Mulles, et al, *Cold Spring Harbor Symp. Quant. Biol.*, Specific Enzymatic Amplification of DNA In Vitro: The Polymerase Chain Reaction, 51:263-273 (1986).

Jones, et al. *EMBO J.*, High Level Expression of Introduced Chimaeric Genes in Regenerated Trasformed Plants, 4:2411-2418 (1985).

DeAlmeida, et al. *Mol. Gen. Genetics*, Transgenic Expression of Two Marker Genes Under The Control of an *Arabiodopsis rbcS* Promoter: Sequences Encoding the Rubisco Transit Peptide Increase Expression Levels, 218:78-86 (1989).

Schnieke, et al. *Science*, Human Factor IX Transgenic Sheep Produced by Transfer of Nuclei From Transfected Fetal Fibroblasts, 278:2130-2133 (1997).

McCabe et al., *BiolTechnology*, Stable Transformation of Soybean (Glycine Max) by Particle Acceleration, 6: 923 (1988).

Christou, et al, *Plant Physicol*, Stable Transformation of Soybean Callus by DNA-Coated Gold Particles, 87:671-674 (1988).

McKently et al., *Plant Cell Rep*, Agrobacterium-Mediated Transformation of Peanut (*Arachis hypogaea* L.) Embryo Azes and the Development of Transgenic Plants, 14:699-703 (1995).

Grant, et al. *Plant Cell Rep*, Transformation of Peas (*Pisum sativum* L.) Using Immature Cotyledons, 15:254-258 (1995).

Bytebler, et al., *Proc Natl Acad Sci*, T-DNA Organization in Tumor Cultures and Transgenic Plants of the Monocotyledon Asparagus Officinalis, (USA) 84:5354 (1987).

Wan & Lemaux, *Plant Physiol*, Gerneration of large Numbers of Independently Transformed Fertile Barley Plants, 10:37 (1994).

Rhodes, et al., *Science*, Genetically Transformed Maize Plants from Protoplasts, 240:204 (1988).

Gordon-Kamm, et al., *Plant Cell*, Transformation of Maize Cells and Regeneration of Fertile Transgenic Plants, 2:603-618 (1990).

Fromm, et al., *BiolTechnology*, Inheritance and Expression of Chimeric Genes in the Progeny of Transgenic Maize Plants, 8:833 (1990).

Koziel, et al., *BioTechnology*, Field Performance of Elite Transgenic Maize Plants Expressing an Insecticidal Protein Derived from *Bacillus thuringiensis*, 11:194 (1993).

Armstrong, et al. *Crop Science*, Cell Biology & Molecular Genetics, 35:550-557 (1995).

Somers, et al., *BiolTechnology*, Fertile, Transgenic Oat Plants, 10:15 89 (1992).

Horn, et al., *Plant Cell Rep*, Transgenic Plants of Orchardgrass (*Dactylis glomerata* L.) From Protoplast, 7:469 (1988).

Park, et al., *Plant Mol. Biol.*, T-DNA Integration Into Genomic DNA of Rice Following Agrobacterium Inoculation of Isolated Shoot Apices, 32:1135-1148 (1996).

Abnedina, et al., *Aust. J. Plant Physiol.*, An Efficient Transformation System for the Australian Rice Cultivar, Jarrah, 24:133-141 (1997).

Zhang & Wu, *Theor. Appl. Genet*, Efficient Regeneration of Transgenic Plants from Rice Protoplasts and Correctly Regulated Expression of the Foreign Gene in the Plants, 76:835 (1988).

Baltraw & Hall, *Plant Sci.*, Expression of a Chimeric Neomycin Phosphotransferase II Gene in First and Second Genration Trasgenic Rice Plants, 86:191-202 (1992).

Christou, et al., *Biol Technology*, Production of Transgenic Rice (*Oryza sativa* L.) Plants From Agronomically Important Indica and Japonica Varieties Via Electric Discharge Particle Acceleration of Exogenous DNA Into Immature Zygotic Embryos, 9:957 (1991).

De La Pena, et al., *Nature*, Transgenic Rye Plants Obtained by Injecting DNA Into Young Floral Tillers, 325:274 (1987).

Bower & Birch, *Plant J.*, Transgenic Sugarcane Plants Via Microprojectile Bombardment, 2:409 (1992).

Wang, et al. *Biol Technology*, Transgenic Plants of Tall Fescue (*Festuca acrundinacea* Schreb.) Obtained by Direct Gene Transfer to Protoplasts, 10:691 (1992).

Vasil, et al. *Biol Technology*, Herbicide Resistant Fertile Transgenic Wheat Plants Obtained by Microprojectile Bombardment of Regenerable Embryogenic Callus, 10:667 (1992).

Marcotte, et al., *Nature*, Regulation of a Wheat Promoter by Abscisic Acid in Rice Protoplasts, 335-454-457 (1988).

McCarty, et al. *Plant Cell*, Molecular Analysis of Vivparous-1: An Abscisic Acid-Senseitive Muntant of Maize, 1:523-532 (1989).

McCarty, et al., *Cell*, The Viviparous-1 Developmental Gene of Maize Encodes a Novel Transcriptional Activator, 66:895-905 (1991).

Hattori, et al., *Genes Dev.*, The Viviparous-1 Gene and Abscisic Acid Activate the C1 Regulatory Gene for Anthocyanin Biosynthesis During Seed Maturation in Maize, 6:609-618 (1992).

Goff, et al., *EMBO J.*, Transactivation of Anthocyanin Biosynthetic Genese Following Transfer of B Regulatory Genes into Maize Tissues, 9:2517-2522 (1990).

Horrobin, et al., *Am. J. Clin. Nutr.*, Fatty Acid Metabolism in Health and Disease: The Role of Δ-6-Desaturase, 57:7325-7345.

Brenner, et al., *Adv. Exp. Med. Biol.*, Function and Biosynthesis of Lipids, 83:85-101 (1976).

Hoge, et al., *Exp. Mycology*, Absence of Differneces in Polysomal RNAs From Vegetative Monokaryotic and Dikaryotic Cells of the Fungus Schizophyllum Commune, 6:225-232 (1982).

Okuley, et al., *The Plant Cell*, Arabiodopisis FAD2 Gene Encodes the Enzyme That is Essential for Polyunsaturated Lipid Synthesis, 6:147-158 (1994).

* cited by examiner

Fatty Acid Biosynthetic Pathway

Figure 2

Gene Sequence of Delta 6- Desaturase from *Synechocystis dictine* (ATCC 56851)

```
   1  ATGGTCCAGG GGCAAAAGGC CGAGAAGATC TCGTGGGCGA CCATCCGTGA
  51  GCACAACCGC CAAGACAACG CGTGGATCGT GATCCACCAC AAGGTGTACG
 101  ACATCTCGGC CTTTGAGGAC CACCCGGGCG GCGTCGTCAT GTTCACGCAG
 151  GCCGGCGAAG ACGCGACCGA TGCGTTCGCT GTCTTCCACC CGAGCTCGGC
 201  GCTCAAGCTC CTCGAGCAGT ACTACGTCGG CGACGTCGAC CAGTCGACGG
 251  CGGCCGTCGA CACGTCGATC TCGGACGAGG TCAAGAAGAG CCAGTCGGAC
 301  TTCATTGCGT CGTACCGCAA GCTGCGCCTT GAAGTCAAGC GCCTCGGCTT
 351  GTACGACTCG AGCAAGCTCT ACTACCTCTA CAAGTGCGCC TCGACGCTGA
 401  GCATTGCGCT TGTGTCGGCG GCCATTTGCC TCCACTTTGA CTCGACGGCC
 451  ATGTACATGG TCGCGGCTGT CATCCTTGGC CTCTTTTACC AGCAGTGCGG
 501  CTGGCTCGCC CATGACTTTC TGCACCACCA AGTGTTTGAG AACCACTTGT
 551  TTGGCGACCT CGTCGGCGTC ATGGTCGGCA ACCTCTGGCA GGGCTTCTCG
 601  GTGCAGTGGT GGAAGAACAA GCACAACACG CACCATGCGA TCCCCAACCT
 651  CCACGCGACG CCCGAGATCG CCTTCCACGG CGACCCGGAC ATTGACACGA
 701  TGCCGATTCT CGCGTGGTCG CTCAAGATGG CGCAGCACGC GGTCGACTCG
 751  CCCGTCGGGC TCTTCTTCAT GCGCTACCAA GCGTACCTGT ACTTTCCCAT
 801  CTTGCTCTTT GCGCGTATCT CGTGGGTGAT CCAGTCGGCC ATGTACGCCT
 851  TCTACAACGT TGGGCCCGGC GGCACCTTTG ACAAGGTCCA GTACCCGCTG
 901  CTCGAGCGCG CCGGCCTCCT CCTCTACTAC GGCTGGAACC TCGGCCTTGT
 951  GTACGCAGCC AACATGTCGC TGCTCCAAGC GGCTGCGTTC CTCTTTGTGA
1001  GCCAGGCGTC GTGCGGCCTC TTCCTCGCGA TGGTCTTTAG CGTCGGCCAC
1051  AACGGCATGG AGGTCTTTGA CAAGGACAGC AAGCCCGATT TTTGGAAGCT
1101  GCAAGTGCTC TCGACGCGCA ACGTGACGTC GTCGCTCTGG ATCGACTGGT
1151  TCATGGGCGG CCTCAACTAC CAGATCGACC ACCACTTGTT CCCGATGGTG
1201  CCCGGCACA  ACCTCCCGGC GCTCAACGTG CTCGTCAAGT CGCTCTGCAA
1251  GCAGTACGAC ATCCATACCC ACGAGACGGG CTTCATCGCG GGCATGGCCG
1301  AGGTCGTCGT GCACCTCGAG CGCATCTCGA TCGAGTTCTT CAAGGAGTTT
1351  CCCGCCATGT AA
```

Figure 3
Amino Acid Sequence of Delta 6- Desaturase from *Synechocystis distinx* (ATCC 56851)

```
1    MYQGQKAEKI  SWATIREHNR  QDNAKIVIHH  KVYDISAFED  HPGGVVMFTQ
51   AGEDATDAFA  VFHPSSALKL  LEQYYVGDVD  QSTAAVDTSI  SDEVKKSQSD
101  FIASYRKLRL  EVKRLGLYDS  SKLYYLYKCA  STLSIALYSA  AICLHFDSTA
151  MYMVAAVILG  LFYQQCGWLA  HDFLHHQVFE  NHLEGDLVGV  MYGNLMQGFS
201  VQWWKNKHNT  HHAIPNLHAT  PEIAFHGDPD  IDTMPILAWS  LKMAQHAVDS
251  PVGLFFMRYQ  AYLYFPILLF  ARISWYIQSA  MYAFYNVGPG  GTEDKVQYPL
301  LFRAGLLLYY  GWNLGLVYAA  NMSLLQAAAF  LFVSQASCGL  FLAMYFSVGH
351  NGMEVFDKDS  KPDFWKLQVL  STRNVTSSLH  IDWEMGGLNY  QIDHHLFPMV
401  PRHNLPALNV  LVKSLCKQYD  IPYHETGFIA  GMAEVVVHLF  RISIFFFKEF
451  PAM*
```

Figure 4
Gene Sequence of Delta 5- Desaturase from *Saprolegnia diclina* (ATCC 56851)

```
   1 ATGGCCCCGC AGACGGAGCT CCGCCAGCGC CACGCCGCCG TCGCCGAGAC
  51 GCCGGTGGCC GGCAAGAAGG CCTTTACATG GCAGGAGGTC GCGCAGCACA
 101 ACACGGCGGC CTCGGCCTGG ATCATTATCC GCGGCAAGGT CTACGACGTG
 151 ACCGAGTGGG CCAACAAGCA CCCCGGCGGC CGCGAGATGG TGCTGCTGCA
 201 CGCCGGTCGC GAGGCCACCG ACACGTTCGA CTCGTACCAC CCGTTCAGCG
 251 ACAAGGCCGA GTCGATCTTG AACAAGTATG AGATTGGCAC GTTCACGGGC
 301 CCGTCCGAGT TTCCGACCTT CAAGCCGGAC ACGGGCTTCT ACAAGGAGTG
 351 CCGCAAGCGC GTTGGCGAGT ACTTCAAGAA GAACAACCTC ATCCGCAGG
 401 ACGGCTTCCC GGGCCTCTGG CGCATGATGG TCGTGTTTGC GGTCGCCGGC
 451 CTCGCCTTGT ACGGCATGCA CTTTTCGACT ATCTTTGCGC TGCAGCTCGC
 501 GGCCGCGGCG CTCTTTGGCG TCTGCCAGGC GCTGCCGCTG CTCCACGTCA
 551 TGCACGACTC GTCGCACGCG TCGTACACCA ACATGCCGTT CTTCCATTAC
 601 GTCGTCGGCC GCTTTGCCAT GGACTGGTTT GCCGGCGGCT CGATGGTGTC
 651 ATGGCTCAAC CAGCACGTCG TGGGCCACCA CATCTACACG AACGTCGCGG
 701 GCTCGGACCC GGATCTTCCG GTCAACATGG ACGGCGACAT CCGCCGCATC
 751 GTGAACCGCC AGGTGTTCCA GCCCATGTAC GCATTCCAGC ACATCTACCT
 801 TCCGCCGCTC TATGGCGTGC TTGGCCTCAA GTTCCGCATC CAGGACTTCA
 851 CCGACACGTT CGGCTCGCAC ACGAACGGCC CGATCCGCGT CAACCCGCAC
 901 GCGCTCTCGA CGTGGATGGC CATGATCAGC TCCAAGTCGT TCTGGGCCTT
 951 CTACCGCGTG TACCTTCCGC TTGCCGTGCT CCAGATGCCC ATCAAGACGT
1001 ACCTTGCGAT CTTCTTCCTC GCCGAGTTTG TCACGGGCTG GTACCTCGCG
1051 TTCAACTTCC AAGTAAGCCA TGTCTCGACC GAGTGCGGCT ACCCATGCGG
1101 CGACGAGGCC AAGATGGCGC TCCAGGACGA GTGGGCAGTC TCGCAGGTCA
1151 AGACGTCGGT CGACTACGCC CATGGCTCGT GGATGACGAC GTTCCTTGCC
1201 GGCGCGCTCA ACTACCAGGT CGTGCACCAC TTGTTCCCCA GCGTGTCGCA
1251 GTACCACTAC CCGGCGATCG CGCCATCAT CGTCGACGTC TGCAAGGAGT
1301 ACAACATCAA GTACGCCATC TTGCCGGACT TTACGGCGGC GTTCGTTGCC
1351 CACTTGAAGC ACCTCCGCAA CATGGGCCAG CAGGGCATCG CCGCCACGAT
1401 CCACATGGGC TAA
```

Figure 5
Amino Acid Sequence of Delta 5- Desaturase from *Saprolegnia diclina* (ATCC 56851)

```
  1    MAPQTEIRQR HAAVAETPYA GKKAETWQEY AQHNTAASAM IIIRGKYYDY
 51    TEWANKHPGG REMYLLHAGR EATDTEDSYH PFSDKAESIL NKYEIGTETG
101    PSEEPTEKED TGFYKECRKR YGEYEKKNNL HPQDGEPGLM RMMVYEAVAG
151    LALYGMHEST IFALQLAAAA LEGVCQALPL LHVMHDSSHA SYTNMPFEHY
201    VVGREAMDWE AGGSMVSKIN QHVVGHHIYT NVAGSDPDLP VMMDGDIRRI
251    VNRQVEQPMY AFQHIYLPPL YGVLGLKERI QDFTDTEGSH TNGPIRVNPH
301    ALSTHMMAMIS SKSEHAFYRV YLPLAVLQMP IKTYLAIEF L AEFYTGWYLA
351    FNEQVSHVST ECGYPCGDEA KMAIQDEWAV SQVKTSVDYA HGSWMTTELA
401    GAINYQVYHH LEPSVSQYHY PAIAPIIVDV CKEYNIKYAI LPDFTAAFVA
451    HLKHLRMMGQ QGIAATIHMG *
```

Figure 6
Gene Sequence of Delta 5- Desaturase from *Thraustochytrium aureum* (ATCC 34304)

```
   1  ATGGGACGCG GCGGCGAAGG TCAGGTGAAC AGCGCGCAGG TGGCACAAGG
  51  CGGTGCGGGA ACGCGAAAGA CGATCCTGAT CGAGGGCGAG GTCTACGATG
 101  TCACCAACTT TAGGCACCCC GGCGGGTCGA TCATCAAGTT TCTCACGACC
 151  GACGGCACCG AGGCTGTGGA CGCGACGAAC GCGTTTCGCG AGTTTCACTG
 201  CCGGTCGGGC AAGGCGGAAA AGTACCTCAA GAGCCTGCCC AAGCTCGGCG
 251  CGCCGAGCAA GATGAAGTTT GACGCCAAGG AGCAGGCCCG GCGCGACGCG
 301  ATCACGCGAG ACTACGTCAA GCTGCGCGAG GAGATGGTGG CCGAGGGCCT
 351  CTTCAAGCCC GCGCCCCTCC ACATTGTCTA CAGGTTTGCG GAGATCGCAG
 401  CCCTGTTCGC GGCCTCGTTC TACCTGTTTT CGATGCGCGG AAACGTGTTC
 451  GCCACGCTCG CGGCCATCGC AGTCGGGGGC ATCGCGCAGG GCCGCTGCGG
 501  CTGGCTCATG CACGAGTGCG GACACTTCTC GATGACCGGG TACATCCCGC
 551  TTGACGTGCG CCTGCAGGAG CTGGTGTACG GCGTGGGGTG CTCGATGTCG
 601  GCGAGCTGGT GGCGCGTTCA GCACAACAAG CACCACGCGA CCCCGCAGAA
 651  ACTCAAGCAC GACGTCGACC TCGACACCCT GCCGCTCGTT GCGTTCAACG
 701  AGAAGATCGC CGCCAAGGTG CGCCCCGGCT CGTTCCAGGC CAAGTGGCTC
 751  TCGGCGCAGG CGTACATTTT TGCGCCGGTG TCCTGCTTCC TGGTTGGTCT
 801  CTTCTGGACC CTGTTTCTGC ACCCGCGCCA CATGCCGCGC ACGAGCCACT
 851  TTGCTGAGAT GGCCGCCGTC GCGGTGCGCG TCGTGGGCTG GGCGGCGCTC
 901  ATGCACTCGT TCGGGTACAG CGGGAGCGAC TCGTTCGGTC TCTACATGGC
 951  CACCTTTGGC TTTGGCTGCA CCTACATCTT CACCAACTTT GCGGTCAGCC
1001  ACACGCACCT CGACGTCACC GAGCCGGACG AGTTCCTGCA CTGGGTCGAG
1051  TACGCCGCGC TGCACACGAC CAACGTGTCC AACGACTCGT GGTTCATCAC
1101  CTGGTGGATG TCGTACCTCA ACTTTCAGAT CGAGCACCAC CTCTTTCCGT
1151  CGCTGCCCCA GCTCAACGCC CCGCGCGTCG CCCGCGCGT CCGCGCCCTC
1201  TTCGAGAAGC ACGGCATGGC TTACGACGAG CGCCCGTACC TTACCGCGCT
1251  TGGCGACACG TTTGCCAACC TGCACGCCGT GGGCCAAAAC GCGGGCCAGG
1301  CGGCGGCCAA GGCCGCTTAG
```

Figure 7

Amino Acid Sequence of Delta 5- Desaturase from *Thraustochytrium aureum* (ATCC 34304)

```
  1  MRGGEGQYN  SAQVPQGGAG  TRKTILIEGE  YYDVTNFRHP  GGSIIKFLTT
 51  DGTEAYDATN  AFREEHCRSS  KAEKYLKSLP  KIGAPSKMKF  DAKEQARRDA
101  ITRDYVKLRE  EMVAEGLFKP  APLHIVYRFA  EIAALEAASF  YLFSMRGNVE
151  ATLAAIAVGG  IAQSRCGYIM  HECGHESMTG  YIPLDVRLQE  LVYGVGCSMS
201  ASWWRYQHNK  HHATPQKLKH  DVDLDTLPIV  AFNEKIAAKV  REGSFQAKHL
251  SBQAYIFAPV  SCFLVGLFWT  LELHERHMPR  TSHFAEMARV  AVRVVGMAAL
301  MHSEGYSSSD  SEGLYMAIFG  FGCTYIFTNF  AVSHTHLDVT  EPDEFLHWVE
351  YAALHTTNYS  NDSWFITHHM  SYLNFQIEHH  LFPSLPQLNA  PRVAPRVRAL
401  FEKHGMAYDE  RPYLTALGDT  FRNLHAVGQN  AGQAAAKAA
```

Figure 8

```
   1  GAATTCACCA TGGGTCGCGG AGCACAGGGA GAGCCAAGGC AGGCCACAGA
  51  GCTGAAGAGC AGCCCAAGTG AGCAGCGTAA GGTGTTGCTC ATTGACGGGC
 101  AGCTGTACGA TGCAACCAAC TTCAGGCATC CTGGTGGCTC CATCATCAAA
 151  TATTTGTGCA CCGATGGCAA GGAGGTAGTT GATGCAACCG AAGCGTACAA
 201  GGAGTTCCAC TGCAGATCCT CGAAGGCGGT CAAGTACCTC AACTCCCTGC
 251  CAAAGATCGA CGGCCCAATC AAGTACAAAT ACGACGCAAA GGAGCAGGCT
 301  CGCCATGACA AACTCACGAG GGAGTATGTA GCTCTCCGCG AACAGCTCGT
 351  CAAGGAGGGA TACTTTGACC CCAGCCCGCT CCACATTATC TACAGATGCG
 401  CCGAGTTGGC AGCCATGTTC GCTCTCTCGT TCTACCTTTT CTCCTTCAAG
 451  GGTAACGTCA TGGCCACTAT TGCTGCCATC GTGATTGGGG GGTGCGTGCA
 501  GGGTCGTTGT GGGTGGCTCA TGCATGAAGC TGGCCACTAC AGCATGACCG
 551  GAAACATCCC TGTTGACTTG CGCCTTCAAG AGTTTTTGTA CGGAATTGGG
 601  TGTGGCATGA GCGGGGCTTG GTGGAGAAGC CAGCACAACA AGCACCACGC
 651  CACCCCCCAA AAGCTCAAGC ATGACGTTGA TTTGGACACT CTTCCTCTTG
 701  TCGCCTGGAA CGAGAAAATT GCCCGTCGCG TCAAGCCAGG TAGCTTCCAG
 751  GCAAAGTGGC TTCATCTCCA GGGATACATC TTTGCCCCAG TCTCCTGCCT
 801  TCTCGTTGGT CTCTTCTGGA CTTTGTACTT GCATCCTCGC CACATGATCC
 851  GCACCAAGCG CAACTTCGAG ATATTTTCTG TCGCTCTGCG CTACGTATGC
 901  TGGTTCTCGC TTCTTTTGAG CATGGGCTAC ACTGTCGGAG AGTTCTGGG
 951  TCTCTATGTG CTTACTTTTG GACTTGGCTG TACCTACATC TTTACGCATT
1001  TTGCTGTAAG CCACACCCAC TTGCCAGTGT CCGAGGAGGA CGAGTACCTG
1051  CACTGGGTCG AGTACGCTGC GCTGCACACC ACGAACGTTG CCATCGACTC
1101  GTACGTTGTC ACCTGGCTGA TGAGCTACCT CAACTTTCAG ATCGAGCACC
1151  ACTTGTTCCC TTGCTGCCCG CAGTTCCGCC ACCCTGCAAT CTCTTCTCGC
1201  GTCAAGAAAC TTTTCGAGGA CAATGGTCTG GTATACGACG CCCGCTCATA
1251  CGTCCAGGCG CTCAAGGATA CCTTCGGCAA CCTACACGAA GTGGGCGTCA
1301  ACGCTGGCCA AGCTGCCAAG AGCGAGTAAG ATCTCGAG
```

Start/stop underlined

Figure 9

```
  1  MGRGAQGEPR QATELKSSPS EQRKVLLIDG QLYDATNERH PGGSIIKYLC
 51  TDGKEVVDAT EAYKEFHCRS SKAVKYLNSL PKIDGPIKYK YDAKEQARHD
101  KLTREYVALR EQLVKEGYFD PSPLHIIYRC AELAAMFALS FYLFSEKGNV
151  MATIAAIVIG GCVQGRCGWL MHEAGHYSMT GNIPVDLRLQ EELYGIGCGM
201  SGAWRSQHN  KHHATPQKLK HDVDLDTLPL VAWNEKIARR VKPGSFQAKW
251  LHLQGYIFAP VSCLLVGLFW TLYLHPRHMI RTKRNFEIES VALRYVCWFS
301  LLLSMGYTVG ESLGLYVLTF GLGCTYIFTH FAVSHTHLPV SEEDEYLHWV
351  EYAALHTTNV AIDSYVVTWL MSYLNFQIEH HLFPCCPQFR HPAISSRVKK
401  LFEDNGLVYD ARSYVQALKD TFGNLHEVGV NAGQAAKSE
```

Figure 10

|  |  |  |  |  |  |
|---|---|---|---|---|---|
| 1 | CCATGGGCCG | CGGCGGCGAG | AAAAGCGAGG | TGGACCAGGT | GCAGCCACAA |
| 51 | AAGACCGAGC | AGCTCCAGAA | GGCCAAGTGG | GAGGATGTTG | TTCGCATCAA |
| 101 | TGGAGTCGAA | TACGACGTCA | CGGACTATCT | CAGAAAACAC | CCTGGTGGCA |
| 151 | GCGTGATCAA | GTACGGGCTT | GCCAACACCG | GCGCTGATGC | CACGTCCCTC |
| 201 | TTTGAAGCGT | TCCACATGCG | CTCAAAGAAG | GCTCAGATGG | TGCTCAAGTC |
| 251 | TCTCCCAAAG | CGTGCTCCGG | TCCTCGAGAT | CCAGCCAAAC | CAGCTTCCAG |
| 301 | AGGAGCAGAC | CAAGGAGGCG | GAGATGCTGC | GTGATTTTAA | AAAATTTGAG |
| 351 | GATGAGATTC | GCCGGGATGG | ATTGATGGAA | CCTTCCTTCT | GGCATCGCGC |
| 401 | TTACAGATTA | TCAGAGCTTG | TAGGTATGTT | CACGCTCGGC | CTCTACCTCT |
| 451 | TCTCGTTAAA | CACTCCTCTG | TCTATTGCTG | CTGGTGTCCT | CGTCCACGGT |
| 501 | CTCTTTGGTG | CATTCTGTGG | ATGGTGCCAG | CATGAGGCAG | GCCACGGCTC |
| 551 | CTTTTTTAC | AGCCTTTGGT | GGGCAAGCG | TGTACAGGCC | ATGTTGATCG |
| 601 | GGTTTGGTCT | AGGAACATCC | GGCGACATGT | GGAACATGAT | GCAACAACAAG |
| 651 | CATCATGCTG | CCACCCAAAA | GGTTCATCAC | GACCTTGACA | TTGACACAAG |
| 701 | TCCTTTTGTA | GCTTTTCTTCA | ACACTGCATT | TGAGAAAAAC | AGATGGAAGG |
| 751 | GCTTTTCCAA | GGCTTGGGTC | CGCTTTCAGG | CTTTCACGTT | CATTCCTGTC |
| 801 | ACCAGCGGCA | TGATCGTCAT | GCTGTTCTGG | CTGTTTTTC | TCCACCCTCG |
| 851 | CCGGTCGTT | CAAAAGAAGA | ACTTTGAGGA | GGGTTTTTGG | ATGCTGTCGA |
| 901 | GCCACATTGT | GCGCACCTAT | CTCTTCCACC | TTGTGACCGG | CTGGGAGAGC |
| 951 | CTCGCTGCAT | GCTACCTTGT | TGGGTATTGG | GCGTGCATGT | GGGTGTCCGG |
| 1001 | TATGTATTTG | TTTGGCCACT | TTTCGCTCTC | CCACACTCAT | ATGGACATTG |
| 1051 | TGGAGGCGGA | CGTGCATAAG | AACTGGGTCA | GGTACGCTGT | TGACCACACT |
| 1101 | GTTGACATCA | GCCCATCCAA | CCCGCTCGTG | TGCTGGGTCA | TGGGTTACCT |
| 1151 | CAACATGCAG | ACCATCCACC | ACTTGTGGCC | TGCCATGCCC | CAGTACCACC |
| 1201 | AGGTCGAGGT | CTCACGCCGC | TTTGCCATCT | TCGCCAAAAA | ACACGGCCTC |
| 1251 | AACTACCGCG | TCGTCTCTTA | CTTTGAGGCT | TGGCGCCTGA | TGCTCCAAAA |
| 1301 | TCTTGCTGAC | GTCGGTTCCC | ACTACCATGA | GAACGGTGTC | AAGCGCGCCC |
| 1351 | CAAAGAAAGC | CAAGGCGCAG | TAGAAAGCTA | T |  |

Start/stop underlined

Figure 11

```
  1  MGRGGEKSEV  DQVQPQKTEQ  LQKAKWEDVV  RINGVEYDVT  DYLRKHPGGS
 51  VIKYGLANTG  ADATSLFEAF  HMRSKKAQMV  LKSLPKRAPV  LEIQPNQLPE
101  EQTKEAEMLR  DEKKFEDEIR  RDGLMEPSFW  HRAYRLSELV  GMFTLGLYLF
151  SLNTPLSIAA  GVLVHGLFGA  FCGWCQHEAG  HGSFFYSLWW  GKRVQAMLIG
201  FGLGTSGDMW  NMMHNKHHAA  TQKVHHDLDI  DTTPFVAFFN  TAFEKNRWKG
251  FSKAWVRFQA  FTFIPVTSGM  IVMLFWLFFL  HPRRVVQKKN  FEEGFWMLSS
301  HIVRTYLFHL  VTGWESLAAC  YLVGYWACMW  VSGMYLFGHF  SLSHTHMDIV
351  EADVHKNWVR  YAVDHTVDIS  PSNPLVCWVM  GYLNMQTIHH  LWPAMPQYHQ
401  VEVSRRFAIF  AKKHGLNYRV  VSYFEAAWRLM  LQNLADVGSH  YHENGVKRAP
451  KKAKAQ
```

Figure 12

```
pRAT-2a    1  MGRGAQGEPRQATELKSSPSEQRKVLL-IDGQLYDATNFRHPGGS-   45
pRAT-2c    1  MGRGAQGEPRQATELKSSPSEQRKVLL-IDGQLYDATNFRHPGGS-   45 pRAT-2a   46  IKYLCTDGKEVVDATEAYKEFHCRSSKADKYLNSLPK-IDGPIKYK   90
pRAT-2c   46  IKYLCTDGKEVVDATEAYKEFHCRSSKAVKYLNSLPK-IDGPIKYK   90 pRAT-2a   91  YDAKEQARHDKLTREYVALREQLVKEGYFDPSPLH--IYRCAELAA  135
pRAT-2c   91  YDAKEQARHDKLTREYVALREQLVKEGYFDPSPLH--IYRCAELAA  135 pRAT-2a  136  MFALSFYLFSFKGNVVATIAA-IV-IGGCVQGRCGWLMHEAGHYSMT  180
pRAT-2c  136  MFALSFYLFSFKGNVMATIAA-IV-IGGCVQGRCGWLMHEAGHYSMT  180 pRAT-2a  181  GNIPVDLRLQEFLYG-IGCGMSGAWWRRQHNKHHATPQKLKHDVDL  225
pRAT-2c  181  GNIPVDLRLQEFLYG-IGCGMSGAWWRSQHNKHHATPQKLKHDVDL  225 pRAT-2a  226  DTLPLVAWNEKIARRVKPGSFQAKWPHLQGY-IFAPVSCLLVGLFW  270
pRAT-2c  226  DTLPLVAWNEKIARRVKPGSFQAKWLHLQGY-IFAPVSCLLVGLFW  270 pRAT-2a  271  TLYLHPRHMIRTKRNFE--IFSVALRYVCWFSLLLSMGYTVGESLGL  315
pRAT-2c  271  TLYLHPRHMIRTKRNFE--IFSVALRYVCWFSLLLSMGYTVGESLGL  315 pRAT-2a  316  YVLTFGLGCTY-IFTHFAVSHTHLPVSEEDEYLHWVEYAALHTTNV  360
pRAT-2c  316  YVLTFGLGCTY-IFTHFAVSHTHLPVSEEDEYLHWVEYAALHTTNV  360 pRAT-2a  361  AIDSYVVTWLMSYLNFQIEHHHLFPCCPQFRHPAISSRVKKLFEDN  405
pRAT-2c  361  AIDSYVVTWLMSYLNFQIEHHHLFPCCPQFRHPAISSRVKKLFEDN  405 pRAT-2a  406  GLVYDARSYVQALKDTFGNLHEVGVNAGQAAKSE  439
pRAT-2c  406  GLVYDARSYVQALKDTFGNLHEVGVNAGQAAKSE  439
```

Figure 13

| | | | |
|---|---|---|---|
| pRAT-1a | 1 | MGRGGEKSEVDQVQPQKTEQLQKAKWEDVVRINGVEYDVTDYLR | 44 |
| pRAT-1b | 1 | MGRGGEKSEVDQVQPQKTEQLQKAKWEDVVRINGVEYDVTDYLR | 44 |
| pRAT-1a | 45 | KHPGGSVIKYGLANTGADATSLFEAFHMRSKKAQMVLKSLPKRA | 88 |
| pRAT-1b | 45 | KHPGGSVIKYGLANTGADATSLFEAFHMRSKKAQMVLKSLPKRA | 88 |
| pRAT-1a | 89 | PVLEIQPNQLPEEQTKEAEMLRDFKKFEDEIRRDGLMEPSFWHR | 132 |
| pRAT-1b | 89 | PVLEIQPNQLPEEQTKEAEMLRDFKKFEDEIRRDGLMEPSFWHR | 132 |
| pRAT-1a | 133 | AYRLSELVGMFTLGLYLFSLNTPLSIAAGVLVHGLFGAFCGWCQ | 176 |
| pRAT-1b | 133 | AYRLSELVGMFTLGLYLFSLNTPLSIAAGVLVHGLFGAFCGWCQ | 176 |
| pRAT-1a | 177 | HEAGHGSFFYSLWWGKRVQAMLIGFGLGTSGDMWNMMHNKHHAA | 220 |
| pRAT-1b | 177 | HEAGHGSFFYSLWWGKRVQAMLIGFGLGTSGDMWNVMHNKHHAA | 220 |
| pRAT-1a | 221 | TQKVHHDLDIDTTPFVAFFNTAFEKNRWKGFSKAWVRFQAFTFI | 264 |
| pRAT-1b | 221 | TQKVHHDLDIDTTPFVAFFNTAFEKNRWKGFSKAWVRFQAFTFI | 264 |
| pRAT-1a | 265 | PVTSGMIVMLFWLFFLHPRRVVQKKNFEEGFWMLSSHIVRTYLF | 308 |
| pRAT-1b | 265 | PVTSGMIVMLFWLFFLHPRRVVQKKNFEEGFWMLSSHIVRTYLF | 308 |
| pRAT-1a | 309 | HLVTGWESLAACYLVGYWACMWVSGMYLFGHFSLSHTHMDIVEA | 352 |
| pRAT-1b | 309 | HLVTGWESLAACYLVGYWACMWVSGMYLFGHFSLSHTHMDIVEA | 352 |
| pRAT-1a | 353 | DVHKNWVRYAVDHTVDISPSNPLVCWVMGYLNMQTIHHLWPAMP | 396 |
| pRAT-1b | 353 | DVHKNWVRYAVDHTVDISPSNPLVCWVMGYLNMQTIHHLWPAMP | 396 |
| pRAT-1a | 397 | QYHQVEVSRRFAIFAKKHGLNYRVVSYFEAWRLMLQNLADVGSH | 440 |
| pRAT-1b | 397 | QYHQVEVSRRFAIFAKKHGLNYRVVSYFEAWRLMLQNLADVGSH | 440 |
| pRAT-1a | 441 | YHENGVKRAPKKAKAQ | 456 |
| pRAT-1b | 441 | YHENGVKRAPKKAKAQ | 456 |

Figure 14

```
   1 ATGGTGGCAG GCAAATCAGG CGCTGCGGCG CACGTGACTC ACAGCTCGAC
  51 ATTGCCCCGT GAGTACCATG GCGCGACCAA CGACTCGCGC TCTGAGGCGG
 101 CCGACGTCAC CGTCTCTAGC ATCGATGCTG AAAAGGAGAT GATCATCAAC
 151 GGCCGCGTGT ATGACGTGTC GTCATTTGTG AAGCGGCACC CAGGTGGCTC
 201 GGTGATCAAG TTCCAGCTGG CGCCGACGC GAGCGACGCG TACAACAACT
 251 TTCACGTCCG CTCCAAGAAG GCGGACAAGA TGCTGTATTC GCTCCCGTCC
 301 CGGCCGGCCG AGGCCGGCTA CGCCCAGGAC GACATCTCCC GCGACTTTGA
 351 GAAGCTGCGC CTCGAGCTGA AGGAGGAGGG CTACTTCGAG CCCAACCTGG
 401 TGCACGTGAG CTACAGGTGT GTGGAGGTTC TTGCCATGTA CTGGGCTGGC
 451 GTCCAGCTCA TCTGGTCCGG GTACTGGTTC CTCGGCGCGA TCGTGGCCGG
 501 CATTGCGCAG GGCCGCTGCG GCTGGCTCCA GCATGAGGGT GGGCACTACT
 551 CGCTCACCGG CAACATCAAG ATCGACCGGC ATCTGCAGAT GGCCATCTAT
 601 GGGCTTGGCT GCGGCATGTC GGGCTGCTAC TGGCGCAACC AGCACAACAA
 651 GCACCACGCC ACGCCGCAGA AGCTCGGGAC CGACCCCGAC CTGCAGACGA
 701 TGCCGCTGGT GGCCTTCCAC AAGATCGTCG GCGCCAAGGC GCGAGGCAAG
 751 GGCAAGGCGT GGCTGGCGTG GCAGGCGCCG CTCTTCTTTG GCGGGATCAT
 801 CTGCTCGCTC GTCTCTTTCG GCTGGCAGTT CGTGCTCCAC CCCAACCACG
 851 CGCTGCGCGT GCACAATCAC CTGGAGCTCG CGTACATGGG CCTGCGGTAC
 901 GTGCTGTGGC ACCTGGCCTT TGGCCACCTC GGGCTGCTGA GCTCGCTCCG
 951 CCTGTACGCC TTTTACGTGG CCGTGGGCGG CACCTACATC TTCACCAACT
1001 TCGCCGTCTC GCACACCCAC AAGGACGTCG TCCCGCCCAC CAAGCACATC
1051 TCGTGGGCAC TCTACTCGGC CAACCACACG ACCAACTGCT CCGACTCGCC
1101 CTTTGTCAAC TGGTGGATGG CCTACCTCAA CTTCCAGATC GAGCACCACC
1151 TCTTCCCGTC GATGCCGCAG TACAACCACC CCAAGATCGC CCGCGGGTG
1201 CGCGCGCTCT TCGAGAAGCA CGGGGTCGAG TATGACGTCC GGCCATACCT
1251 GGAGTGTTTT CGGGTCACGT ACGTCAACCT GCTCGCCGTA GGCAACCCGG
1301 AGCACTCCTA CCACGAGCAC ACGCACTAG
```

Figure 15

```
  1  MVAGKSGAAA HVTHSSTLPR EYHGATNDSR SEAADVTVSS IDAEKEMIIN

51  GRVYDVSSFV KRHPGGSVIK FQLGADASDA YNNFHVRSKK ADKMLYSLPS

101  RPAEAGYAQD DISRDFEKLR LELKEEGYFE PNLVHVSYRC VEVLAMYWAG

151  VQLIWSGYWF LGAIVAGIAQ GRCGWLQHEG GHYSLTGNIK IDRHLQMAIY

201  GLGCGMSGCY WRNQHNKHHA TPQKLGTDPD LQTMPLVAFH KIVGAKARGK

251  GKAWLAWQAP LFFGGIICSL VSFGWQFVLH PNHALRVHNH LELAYMGLRY

301  VLWHLAFGHL GLLSSLRLYA FYVAVGGTYI FTNFAVSHTH KDVVPPTKHI

351  SWALYSANHT TNCSDSPFVN WWMAYLNFQI EHHLFPSMPQ YNHPKIAPRV

401  RALFEKHGVE YDVRPYLECF RVTYVNLLAV GNPEHSYHEH TH
```

DESATURASE GENES AND USES THEREOF

The subject application is a Continuation-In-Part of pending U.S. patent application Ser. No. 09/769,863, filed on Jan. 25, 2001 now U.S. Pat. No. 6,635,451, which is hereby incorporated in its entirety by reference.

BACKGROUND OF THE INVENTION

1. Technical Field

The subject invention relates to the identification and isolation of genes that encodes enzymes (i.e., *Thraustochytrium aureum* Δ5-desaturase, *Saprolegnia diclina* Δ5-desaturase, *Saprolegnia diclina* Δ6-desaturase and *Isochrysis galbana* Δ5-desaturase) involved in the synthesis of polyunsaturated fatty acids and to uses thereof. In particular, Δ5-desaturase catalyzes the conversion of, for example, dihomo-γ-linolenic acid (DGLA) to arachidonic acid (AA) and (n-3)-eicosatetraenoic acid (20:4n-3) to eicosapentaenoic acid (20:5n-3). Delta-6 desaturase catalyzes the conversion of, for example, α-linolenic acid (ALA) to stearidonic acid (STA). The converted products may then be utilized as substrates in the production of other polyunsaturated fatty acids (PUFAs). The product or other polyunsaturated fatty acids may be added to pharmaceutical compositions, nutritional composition, animal feeds as well as other products such as cosmetics.

2. Background Information

Desaturases are critical in the production of long-chain polyunsaturated fatty acids that have many important functions. For example, polyunsaturated fatty acids (PUFAs) are important components of the plasma membrane of a cell, where they are found in the form of phospholipids. They also serve as precursors to mammalian prostacyclins, eicosanoids, leukotrienes and prostaglandins. Additionally, PUFAs are necessary for the proper development of the developing infant brain as well as for tissue formation and repair. In view of the biological significance of PUFAs, attempts are being made to produce them, as well as intermediates leading to their production, in an efficient manner.

A number of enzymes are involved in PUFA biosynthesis in addition to Δ5-desaturase and Δ6-desaturase. For example, elongase (elo) catalyzes the conversion of γ-linolenic acid (GLA) to dihomo-γ-linolenic acid (DGLA) and of stearidonic acid (18:4n-3) to (n-3)-eicosatetraenoic acid (20:4n-3). Linoleic acid (LA, 18:2-Δ9,12 or 18:2n-6) is produced from oleic acid (18:1-Δ9) by a Δ12-desaturase. GLA (18:3-Δ6,9,12) is produced from linoleic acid by a Δ6-desaturase.

It must be noted that animals cannot desaturate beyond the Δ9 position and therefore cannot convert oleic acid into linoleic acid. Likewise, α-linolenic acid (ALA, 18:3-Δ9,12, 15) cannot be synthesized by mammals. However, α-linolenic acid can be converted to stearidonic acid (STA, 18:4-Δ6,9,12,15) by a Δ6-desaturase (see PCT publication WO 96/13591 and *The Faseb Journal,* Abstracts, Part I, Abstract 3093, page A532 (Experimental Biology 98, San Francisco, Calif., Apr. 18–22, 1998); see also U.S. Pat. No. 5,552,306), followed by elongation to (n-3)-eicosatetraenoic acid (20: 4-Δ8,11,14,17) in mammals and algae. This polyunsaturated fatty acid (i.e., 20:4-Δ8,11,14,17) can then be converted to eicosapentaenoic acid (EPA, 20:5-Δ5,8,11,14,17) by a Δ5-desaturase, such as that of the present invention. Other eukaryotes, including fungi and plants, have enzymes which desaturate at carbon 12 (see PCT publication WO 94/11516 and U.S. Pat. No. 5,443,974) and carbon 15 (see PCT publication WO 93/11245). The major polyunsaturated fatty acids of animals therefore are either derived from diet and/or from desaturation and elongation of linoleic acid or α-linolenic acid. In view of these difficulties, it is of significant interest to isolate genes involved in PUFA synthesis from species that naturally produce these fatty acids and to express these genes in a microbial, plant, or animal system which can be altered to provide production of commercial quantities of one or more PUFAs.

One of the most important long chain PUFAs, noted above, is arachidonic acid (AA). AA is found in filamentous fungi and can also be purified from mammalian tissues including the liver and adrenal glands. As noted above, AA production from dihomo-γ-linolenic acid is catalyzed by a Δ5-desaturase. EPA is another important long-chain PUFA. EPA is found in fungi and also in marine oils. As noted above, EPA is produced from (n-3)-eicosatetraenoic acid and is catalyzed by a Δ5-desaturase. In view of the above discussion, there is a definite need for the Δ5-desaturase and Δ6-desaturase enzymes, the respective genes encoding these enzymes, as well as recombinant methods of producing these enzymes. Additionally, a need exists for oils containing levels of PUFAs beyond those naturally present as well as those enriched in novel PUFAs. Such oils can only be made by isolation and expression of the Δ5-desaturase and Δ6-desaturase genes.

All U.S. patents, priority documents and publications referred to herein are hereby incorporated in their entirety by reference.

SUMMARY OF THE INVENTION

The present invention includes an isolated nucleotide sequence or fragment comprising or complementary to at least about 50% of a nucleotide sequence comprising SEQ ID NO:13 (FIG. 2), SEQ ID NO:19 (FIG. 4), SEQ ID NO:28 (FIG. 6), SEQ ID NO:30 (FIG. 8), SEQ ID NO:32 (FIG. 10) or SEQ ID NO:34 (FIG. 14). In particular, the isolated nucleotide sequence may be represented by SEQ ID NO:13, SEQ ID NO:19, SEQ ID NO:28, SEQ ID NO:30, SEQ ID NO:32 or SEQ ID NO:34. These sequences may encode a functionally active desaturase which utilizes a polyunsaturated fatty acid as a substrate.

Furthermore, the present invention encompasses an isolated nucleotide sequence or fragment comprising or complementary to a nucleotide sequence encoding a polypeptide having desaturase activity and having at least 50% identity or similarity to an amino acid sequence selected from the group consisting of SEQ ID NO:20, SEQ ID NO:29, SEQ ID NO:31, SEQ ID NO:33 and SEQ ID NO:35.

The nucleotide sequences may be derived from, for example, a fungus such as *Saprolegnia diclina* (SEQ ID NO:13 and SEQ ID NO:19) or *Thraustochytrium aureum* (SEQ ID NO:28, SEQ ID NO:30 and SEQ ID NO:32), or an algae such as, for example, *Isochrysis galbana* (SEQ ID NO:34).

The present invention also includes purified proteins or polypeptides (SEQ ID NO:14 (FIG. 3), SEQ ID NO:20 (FIG. 5), SEQ ID NO:29 (FIG. 7), SEQ ID NO: 31 (FIG. 31), SEQ ID NO:33 (FIG. 11) and SEQ ID NO:35 (FIG. 15)) encoded by the nucleotide sequences referred to above.

Additionally, the present invention includes a purified polypeptide which desaturates polyunsaturated fatty acids at carbon 5 or carbon 6 and has at least about 50% amino acid identity or similarity to the amino acid sequence of the purified proteins referred to directly above (i.e., SEQ ID NO:14, SEQ ID NO:20, SEQ ID NO:29, SEQ ID NO:31, SEQ ID NO:33 and SEQ ID NO:35).

Furthermore, the present invention also encompasses a method of producing a desaturase (i.e., Δ5 or Δ6). This method comprises the steps of: a) isolating the nucleotide sequence comprising SEQ ID NO:19, SEQ ID NO:28, SEQ ID NO:13, SEQ ID NO:30, SEQ ID NO:32, or SEQ ID NO:34 as appropriate; b) constructing a vector comprising: i) the isolated nucleotide sequence operably linked to ii) a promoter or some type of regulatory sequence; and c) introducing the vector into a host cell for a time and under conditions sufficient for expression of the Δ5-desaturase or Δ6-desaturase, as appropriate. The host cell may be, for example, a eukaryotic cell or a prokaryotic cell. In particular, the prokaryotic cell may be, for example, *E. coli*, Cyanobacteria or *B. subtilis*. The eukaryotic cell may be, for example, a mammalian cell, an insect cell, a plant cell or a fungal cell (e.g., a yeast cell such as *Saccharomyces cerevisiae, Saccharomyces carlsbergensis, Candida* spp., *Lipomyces starkey, Yarrowia lipolytica, Kluyveromyces* spp., *Hansenula* spp., *Trichoderma* spp. or *Pichia* spp.).

Additionally, the present invention also encompasses a vector comprising: a) a nucleotide sequence as represented by SEQ ID NO:13, SEQ ID NO:19, SEQ ID NO:28, SEQ ID NO:30, SEQ ID NO:32 or SEQ ID NO:34 operably linked to b) a promoter or regulatory sequence. The invention also includes a host cell comprising this vector. The host cell may be, for example, a eukaryotic cell or a prokaryotic cell. Suitable eukaryotic cells and prokaryotic cells are as defined above.

Moreover, the present invention also includes a plant cell, plant or plant tissue comprising the above vector, wherein expression of the nucleotide sequence of the vector results in production of at least one polyunsaturated fatty acids by the plant cell, plant or plant tissue. The polyunsaturated fatty acid may be, for example, selected from the group consisting of AA, EPA, GLA or STA, depending upon whether the nucleotide sequence encodes a Δ5- or Δ6-desaturase. The invention also includes one or more plant oils or acids expressed by the above plant cell, plant or plant tissue.

Additionally, the present invention also encompasses a transgenic plant comprising the above vector, wherein expression of the nucleotide sequence of the vector results in production of a polyunsaturated fatty acid in seeds of the transgenic plant.

Also, the invention includes a mammalian cell comprising the above vector wherein expression of the nucleotide sequence of the vector results in production of altered levels of AA, EPA, GLA and/or STA when the cell is grown in a culture media comprising a fatty acid selected from the group consisting of, for example, LA, ALA, DGLA and ETA.

It should also be noted that the present invention encompasses a transgenic, non-human mammal whose genome comprises a DNA sequence encoding a Δ5-desaturase or a Δ6-desaturase, operably linked to a promoter or regulatory sequence. The DNA sequence may be represented by SEQ ID NO:13 (Δ6), SEQ ID NO:19 (Δ5), SEQ ID NO:28 (Δ5), SEQ ID NO:30 (Δ5), SEQ ID NO:32 (Δ6) and SEQ ID NO:34 (Δ5). Additionally, the present invention includes a fluid (e.g., milk) produced by the transgenic, non-human mammal wherein the fluid comprises a detectable level of at least Δ5-desaturase or at least Δ6-desaturase, as appropriate.

Additionally, the present invention includes a method (i.e., "first" method) for producing a polyunsaturated fatty acid comprising the steps of: a) isolating the nucleotide sequence represented by, for example, SEQ ID NO:19, SEQ ID NO:28, SEQ ID NO:30 or SEQ ID NO:34; b) constructing a vector comprising the isolated nucleotide sequence; c) introducing the vector into a host cell under time and conditions sufficient for expression of Δ5-desaturase enzyme; and d) exposing the expressed human Δ5-desaturase enzyme to a substrate polyunsaturated fatty acid in order to convert the substrate to a product polyunsaturated fatty acid. The substrate polyunsaturated fatty acid may be, for example, DGLA or 20:4n-3 and the product polyunsaturated fatty acid may be, for example, AA or EPA, respectively. This method may further comprise the step of exposing the product polyunsaturated fatty acid to an elongase or desaturase in order to convert the product polyunsaturated fatty acid to another polyunsaturated fatty acid (i.e., "second" method). In this method containing the additional step (i.e., "second" method), the product polyunsaturated fatty acid may be, for example, AA or EPA, and the "another" polyunsaturated fatty acid may be adrenic acid or (n-3)-docosapentaenoic acid, respectively. The method containing the additional step may further comprise a step of exposing the another polyunsaturated fatty acid to an additional desaturase or elongase in order to convert the another polyunsaturated fatty acid to a final polyunsaturated fatty acid (i.e., "third" method). The final polyunsaturated fatty acid may be, for example, (n-6)-docosapentaenoic acid or docosahexaenoic (DHA) acid.

Additionally, the present invention includes a method for producing a polyunsaturated fatty acid comprising the steps of: a) isolating the nucleotide sequence represented by SEQ ID NO:13 or SEQ ID NO:33; b) constructing a vector comprising the isolated nucleotide sequence; c) introducing the vector into a host cell for a time and under conditions sufficient for expression of Δ6-desaturase enzyme; and d) exposing the expressed Δ6-desaturase enzyme to a substrate polyunsaturated fatty acid in order to convert the substrate to a product polyunsaturated fatty acid. The substrate polyunsaturated fatty acid may be, for example, LA or ALA, and the product polyunsaturated fatty acid may be, for example, GLA or STA, respectively. This method may further comprise the step of exposing the product polyunsaturated fatty acid to an elongase (or desaturase) in order to convert the product polyunsaturated fatty acid to another polyunsaturated fatty acid. In this method containing the additional step, the product polyunsaturated fatty acid may be, for example, GLA or STA, and the "another" polyunsaturated fatty acid may be DGLA or eicosatetraenoic acid (ETA), respectively. The method containing the additional step may further comprise a step of exposing the another polyunsaturated fatty acid to an additional desaturase (or elongase) in order to convert the another polyunsaturated fatty acid to a final polyunsaturated fatty acid. The final polyunsaturated fatty acid may be, for example, AA or EPA.

The present invention also encompasses a nutritional composition comprising at least one polyunsaturated fatty acid selected from the group consisting of the product polyunsaturated fatty acid produced according to the methods described above, the another polyunsaturated fatty acid produced according to the methods described above, and the final polyunsaturated fatty acid produced according to the methods described above. The product polyunsaturated fatty acid may be, for example, AA, EPA, GLA or STA, depending upon whether one is using a Δ5- or Δ6-desaturase nucleotide sequence. The another polyunsaturated fatty acid may be, for example, adrenic acid, (n-3)-docosapentaenoic acid, DGLA and EPA, again depending upon whether one is using a Δ5- or Δ6-desaturase nucleotide sequence. The final polyunsaturated fatty acid may be, for example, (n-6)- docosapentaenoic acid, DHA, AA or EPA, again, depending upon whether one is using a Δ5- or Δ6-desaturase nucleotide sequence.

The present invention also includes a pharmaceutical composition comprising 1) at least one polyunsaturated fatty acid (PUFA) selected from the group consisting of the "product" PUFA produced according to the methods described above, the "another" PUFA produced according to the methods described above, or the "final" PUFA produced according to the methods described above and 2) a pharmaceutically acceptable carrier.

Additionally, the present invention encompasses an animal feed or cosmetic comprising at least one PUFA selected from the group consisting of the product PUFA produced according to the methods described above, the another PUFA produced according to the methods described above and the final PUFA produced according to the methods described above. These PUFAs have been listed above and are exemplified in FIG. 1.

Additionally, the present invention encompasses a method of preventing or treating a condition caused by insufficient intake of polyunsaturated fatty acids comprising administering to the patient the nutritional composition above in an amount sufficient to effect prevention or treatment.

It should also be noted that each nucleotide and amino acid sequence referred to herein has been assigned a particular sequence identification number. The Sequence Listing (which is found herein) lists each such sequence and its corresponding number.

BRIEF DESCRIPTION OF THE DRAWINGS

FIG. 2 illustrates the nucleotide sequence encoding Δ6-desaturase of *Saprolegnia diclina* (ATCC 56851)(SEQ ID NO:13).

FIG. 3 illustrates the amino acid sequence of Δ6-desaturase of *Saprolegnia diclina* (ATCC 56851)(SEQ ID NO:14).

FIG. 4 illustrates the nucleotide sequence encoding Δ5desaturase of *Saprolegnia diclina* (ATCC 56851)(SEQ ID NO:19).

FIG. 5 illustrates the amino acid sequence of Δ5-desaturase of *Saprolegnia diclina* (ATCC 56851)(SEQ ID NO:20).

FIG. 6 illustrates the nucleotide sequence encoding Δ5-desaturase of *Thraustochytrium aureum* (ATCC 34304) (SEQ ID NO:28).

FIG. 7 illustrates the amino acid sequence of Δ5-desaturase of *Thraustochytrium aureum* (ATCC 34304)(SEQ ID NO:29).

FIG. 8 illustrates the nucleotide sequence encoding Δ5-desaturase from *Thraustochytrium aureum* (BICC7091) (SEQ ID NO:30).

FIG. 9 illustrates the translated amino acid sequence of Δ5-desaturase from *Thraustochytrium aureum* (BICC7091) (SEQ ID NO:31).

FIG. 10 illustrates the nucleotide sequence encoding Δ6-desaturase from *Thraustochytrium aureum* (BICC7091) (SEQ ID NO:32).

FIG. 11 illustrates the translated amino acid sequence of Δ6-desaturase from *Thraustochytrium aureum* (BICC7091) (SEQ ID NO:33).

FIG. 12 illustrates the Δ5-desaturase amino acid sequence identity between pRAT-2a and pRAT-2c clones.

FIG. 13 illustrates the Δ6-desaturase amino acid sequence identity between pRAT-1a and pRAT-1b clones.

FIG. 14 illustrates the nucleotide sequence encoding Δ5-desaturase gene from *Isochrysis galbana* CCMP1323 (SEQ ID NO:34).

FIG. 15 illustrates the translated amino acid sequence from Δ5-desaturase from *Isochrysis galbana* CCMP1323 (SEQ ID NO:35).

DETAILED DESCRIPTION OF THE INVENTION

Figure 1:
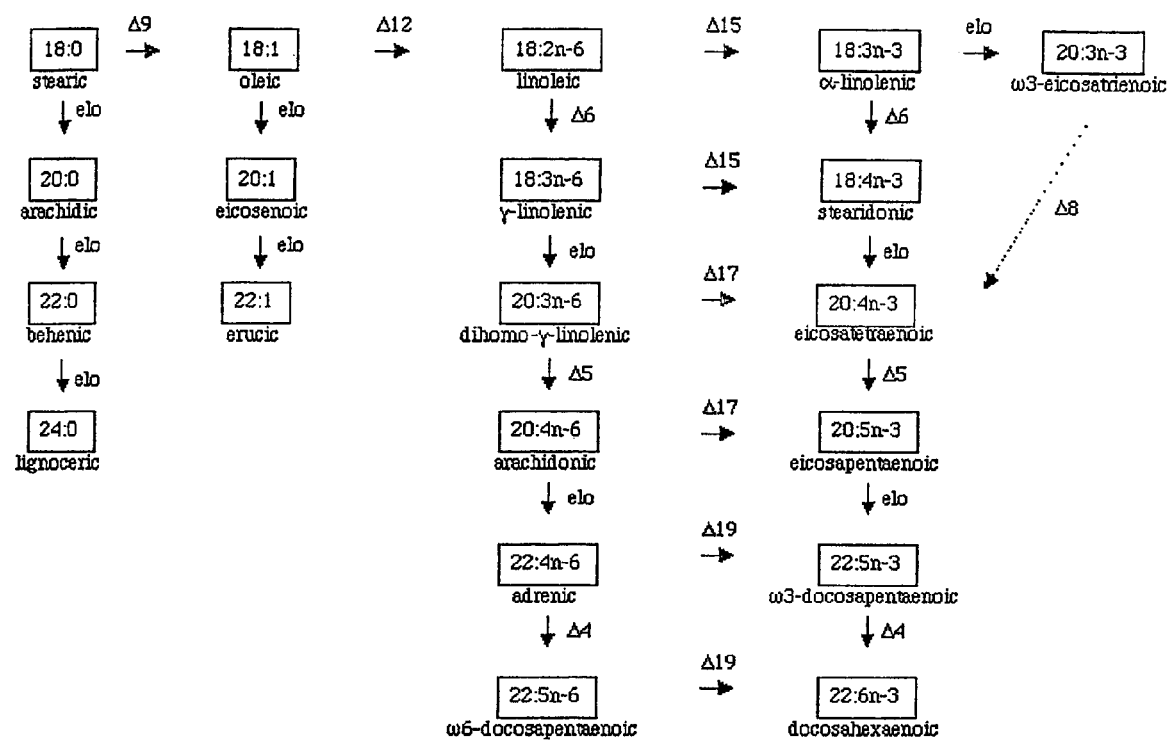
FIG. 1 illustrates the fatty acid biosynthetic pathway and the roles of Δ5desaturase and Δ6-desaturase in this pathway.

The subject invention relates to the nucleotide and translated amino acid sequences of a Δ5-desaturase gene derived from *Saprolegnia diclina*, a Δ6-desaturase gene derived from *Saprolegnia diclina*, two Δ5-desaturase genes derived from *Thraustochytrium aureum* and a Δ6-desaturase gene derived from *Isochrysis galbana*. Furthermore, the subject invention also includes uses of these genes and of the enzymes encoded by these genes. For example, the genes and corresponding enzymes may be used in the production of polyunsaturated fatty acids such as, for instance, arachidonic acid, eicosapentaenoic acid, and/or adrenic acid which may be added to pharmaceutical compositions, nutritional compositions and to other valuable products.

The Δ5-Desaturase Genes, the Δ6-Desaturase Genes, and Enzymes Encoded Thereby

As noted above, the enzymes encoded by the Δ5-desaturase genes and the Δ6-desaturase genes of the present invention are essential in the production of highly unsaturated polyunsaturated fatty acids having a length greater than 20 and 18 carbons, respectively. The nucleotide sequence of the isolated *Thraustochytrium aureum* Δ5-desaturase gene (ATCC 34304) is shown in FIG. 6, and the amino acid sequence of the corresponding purified protein is shown in FIG. 7. The nucleotide sequence of the isolated *Saprolegnia diclina* Δ5-desaturase gene is shown in FIG. 4, and the amino acid sequence of the corresponding purified protein is shown in FIG. 5. The nucleotide sequence of the isolated *Saprolegnia diclina* Δ6-desaturase gene is shown in FIG. 2, and the amino acid sequence of the corresponding purified protein is shown in FIG. 3. The nucleotide sequence of the isolated *Thraustochytrium aureum* (BICC7091) Δ5-desaturase gene is shown in FIG. 8, and the amino acid sequence of the corresponding purified protein is shown in FIG. 9. The nucleotide sequence of the isolated *Thraustochytrium aureum* Δ6-desaturase gene is shown in FIG. 10, and the amino acid sequence of the corresponding purified protein is shown in FIG. 11. Finally, the nucleotide sequence of the isolated *Isochrysis galbana* Δ5-desaturase gene is shown in FIG. 14, and the amino acid sequence of the corresponding purified protein is shown in FIG. 15.

As an example of the importance of the genes of the present invention, the isolated Δ5-desaturase genes convert DGLA to AA or convert eicosatetraenoic acid to EPA. AA, for example, cannot be synthesized without the Δ5-desaturase genes and enzymes encoded thereby. The isolated Δ6-desaturase gene of the present invention converts, for example, linoleic acid (18:2n-6) to γ-linoleic acid (GLA) and γ-linolenic acid (GLA) to stearidonic acid (STA).

It should be noted that the present invention also encompasses nucleotide sequences (and the corresponding encoded proteins) having sequences comprising or complementary to at least about 50%, preferably at least about 60%, more preferably at least about 70%, even more preferably at least about 80%, and most preferably at least about 90% of the nucleotides in sequence (i.e., having sequence identity) to SEQ ID NO:19 (i.e., the nucleotide sequence of the Δ5-desaturase gene of *Saprolegnia diclina*), SEQ ID NO:13 (i.e., the nucleotide sequence of the Δ6-desaturase gene of *Thraustochyrium aureum*), SEQ ID NO:28 (i.e., the nucleotide sequence of the Δ5-desaturase gene of *Thraustochytrium aureum* (ATCC 34304), SEQ ID NO:30 (i.e., the nucleotide sequence of the Δ5-desaturase gene of *Thraustochytrium aureum* (BICC7091), SEQ ID NO:32 (i.e., Δ6-desaturase gene of *Thraustochytrium aureum*) and SEQ ID NO:34 (i.e., Δ5-desaturase gene of *Isochrysis galbana*), described herein. (All integers between 50% and 100% are also considered to be within the scope of the present invention with respect to percent identity.) Such sequences may be derived from human sources as well as other non-human sources (e.g., *C. elegans* or mouse).

Furthermore, the present invention also encompasses fragments and derivatives of the nucleotide sequences of the present invention (i.e., SEQ ID NO:13, SEQ ID NO:19, SEQ ID NO:28, SEQ ID NO:30, SEQ ID NO:32 and SEQ ID NO:34), as well as of the sequences derived from other sources, and having the above-described complementarity or correspondence. Functional equivalents of the above-sequences (i.e., sequences having Δ5-desaturase activity or Δ6-desaturase activity, as appropriate) are also encompassed by the present invention.

The invention also includes a purified polypeptide which desaturates polyunsaturated fatty acids at the carbon 5 position or carbon 6 position and has at least about 50% amino acid similarity or identity, preferably at least about 60% similarity or identity, more preferably at least about 70% similarity or identity, even more preferably at least about 80% similarity or identity, and most preferably at least about 90% similarity or identity to the amino acid sequences (i.e., SEQ ID NO:14 (shown in FIG. 3), SEQ ID NO:20 (shown in FIG. 5), SEQ ID NO:29 (shown in FIG. 7), SEQ ID NO:31 (shown in FIG. 9), SEQ ID NO:33 (shown in FIG. 11) and SEQ ID NO:35 (shown in FIG. 15)) of the above-noted proteins which are, in turn, encoded by the above-described nucleotide sequences. All integers between 50–100% similarity or identity are also included within the scope of the invention.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments. "Percentage of sequence identity" is calculated by comparing two optimally aligned sequences over a particular region, determining the number of positions at which the identical base occurs in both sequence in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Clustal Macaw Pileup (http://cmgm.stanford.edu/biochem218/11Multiple.pdf; Higgins et al., CABIOS. 5L151–153 (1989)), FASTDB (Intelligenetics), BLAST (National Center for Biomedical Information; Altschul et al., Nucleic Acids Research 25:3389–3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

For purposes of the present invention, "complementarity is defined as the degree of relatedness between two DNA segments. It is determined by measuring the ability of the sense strand of one DNA segment to hybridize with the antisense strand of the other DNA segment, under appropriate conditions, to form a double helix. In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity between two amino acid sequences is defined as the presence of a series of exactly alike or invariant amino acid residues in both sequences.) The definitions of "complementarity", "identity" and "similarity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

The present invention also encompasses an isolated nucleotide sequence which encodes PUFA desaturase activity and that is hybridizable, under moderately stringent conditions, to a nucleic acid having a nucleotide sequence comprising or complementary to the nucleotide sequence comprising SEQ ID NO:13 (shown in FIG. 2), SEQ ID NO:19 (shown in FIG. 4), SEQ ID NO:28 (shown in FIG. 6), SEQ ID NO:30 (shown in FIG. 8), SEQ ID NO:32 (shown in FIG. 10) or SEQ ID NO:34 (shown in FIG. 14). A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

As used herein, an "isolated nucleic acid fragment or sequence" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (A "fragment" of a specified polynucleotide refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferable at least about 25 nucleotides identical or complementary to a region of the specified nucleotide sequence.) Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "fragment or subfragment that is functionally equivalent" and "functionally equivalent fragment or subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric constructs to produce the desired phenotype in a transformed plant. Chimeric constructs can be designed for use in co-suppression or antisense by linking a nucleic acid fragment or subfragment thereof, whether or not it encodes an active enzyme, in the appropriate orientation relative to a plant promoter sequence.

The terms "homology", "homologous " "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

"Gene" refers to a nucleic acid fragment that expresses a specific protein, including regulatory sequences preceding (5' non-coding sequences) and following (3' non-coding sequences) the coding sequence.

"Native gene" refers to a gene as found in nature with its own regulatory sequences. In contrast, "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment.)

A "foreign" gene refers to a gene not normally found in the host organism, but that is introduced into the host organism by gene transfer. Foreign genes can comprise native genes inserted into a non-native organism, or chimeric constructs. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) *Nature* (London) 327:70–73; U.S. Pat. No. 4,945,050), or an Agrobacterium-mediated method using an-appropriate Ti plasmid containing the transgene (Ishida Y. et al., 1996, Nature Biotech. 14:745–750). The term "transformation" as used herein refers to both stable transformation and transient transformation.

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al, *Cold Spring Harbor Symp. Quant. Biol.* 51:263–273 (1986); Erlich et al, European Patent Application 50,424; European Patent Application 84,796; European Patent Application 258,017, European Patent Application 237,362; Mullis, European Patent Application 201,184, Mullis et al U.S. Pat. No. 4,683,202; Erlich, U.S. Pat. No. 4,582,788; and Saiki et al, U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20–50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be itself or may be used in conjunction with a vector. If a vector is used then the choice of vector is dependent upon the method that will be used to transform host plants as is well known to those skilled in the art. For example, a plasmid vector can be used.

The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Production of the Δ5-Desaturase Enzymes and the Δ6-Desaturase Enzymes

Once the gene encoding any one of the desaturase enzymes has been isolated, it may then be introduced into either a prokaryotic or eukaryotic host cell through the use of a vector or construct. The vector, for example, a bacteriophage, cosmid or plasmid, may comprise the nucleotide sequence encoding either of the Δ5-desaturase enzymes, or the Δ6-desaturase enzyme, as well as any regulatory sequence (e.g., promoter) which is functional in the host cell and is able to elicit expression of the desaturase encoded by the nucleotide sequence. The regulatory sequence is in operable association with or operably linked to the nucleotide sequence. (As noted above, regulatory is said to be "operably linked" with a coding sequence if the regulatory sequence affects transcription or expression of the coding sequence.) Suitable promoters include, for example, those from genes encoding alcohol dehydrogenase, glyceraldehyde-3-phosphate dehydrogenase, phosphoglucoisomerase, phosphoglycerate kinase, acid phosphatase, T7, TPI, lactase, metallothionein, cytomegalovirus immediate early, whey acidic protein, glucoamylase, and promoters activated in the presence of galactose, for example, GAL1 and GAL10. Additionally, nucleotide sequences which encode other proteins, oligosaccharides, lipids, etc. may also be included within the vector as well as other regulatory sequences such as a polyadenylation signal (e.g., the poly-A signal of SV-40T-antigen, ovalalbumin or bovine growth hormone). The choice of sequences present in the construct is dependent upon the desired expression products as well as the nature of the host cell.

As noted above, once the vector has been constructed, it may then be introduced into the host cell of choice by methods known to those of ordinary skill in the art including, for example, transfection, transformation and electroporation (see *Molecular Cloning: A Laboratory Manual*, $2^{nd}$ ed., Vol. 1–3, ed. Sambrook et al., Cold Spring Harbor Laboratory Press (1989)). The host cell is then cultured under suitable conditions permitting expression of the genes leading to the production of the desired PUFA, which is then recovered and purified.

Examples of suitable prokaryotic host cells include, for example, bacteria such as *Escherichia coli, Bacillus subtilis* as well as cyanobacteria such as *Spirulina* spp. (i.e., blue-green algae). Examples of suitable eukaryotic host cells include, for example, mammalian cells, plant cells, yeast cells such as *Saccharomyces cerevisiae, Saccharomyces carlsbergensis, Lipomyces starkey, Candida* spp. such as *Yarrowia* (*Candida*) *lipolytica, Kluyveromyces* spp., *Pichia* spp., *Trichoderma* spp. or *Hansenula* spp., or fungal cells such as filamentous fungal cells, for example, *Aspergillus, Neurospora* and *Penicillium*. Preferably, *Saccharomyces cerevisiae* (baker's yeast) cells are utilized.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the enzyme(s) of interest (i.e., one or more of the Δ5-desaturases, one or more of the Δ6-desaturases, or a combination thereof), and ultimately the PUFA(s) of interest. More specifically, once the above-described construct is created, it may be inserted into the pronucleus of an embryo. The embryo may then be implanted into a recipient female. Alternatively, a nuclear transfer method could also be utilized (Schnieke et al., *Science* 278:2130–2133 (1997)). Gestation and birth are then permitted (see, e.g., U.S. Pat. Nos. 5,750,176 and 5,700,671). Milk, tissue or other fluid samples from the offspring should then contain altered levels of PUFAs, as compared to the levels normally found in the non-transgenic animal. Subsequent generations may be monitored for production of the altered or enhanced levels of PUFAs and thus incorporation of the gene encoding the desired desaturase enzyme into their genomes. The mammal utilized as the host may be selected from the group consisting of, for example, a mouse, a rat, a rabbit, a pig, a goat, a sheep, a horse and a cow. However, any mammal may be used provided it has the ability to incorporate DNA encoding the enzyme of interest into its genome.

For expression of a desaturase polypeptide, functional transcriptional and translational initiation and termination regions are operably linked to the DNA encoding the desaturase polypeptide. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. Expression in a plant tissue and/or plant part presents certain efficiencies, particularly where the tissue or part is one which is harvested early, such as seed, leaves, fruits, flowers, roots, etc. Expression can be targeted to that location with the plant by utilizing specific regulatory sequence such as those of U.S. Pat. Nos. 5,463,174, 4,943,674, 5,106,739, 5,175,095, 5,420,034, 5,188,958, and 5,589,379. Alternatively, the expressed protein can be an enzyme which produces a product which may be incorporated, either directly or upon further modifications, into a fluid fraction from the host plant. Expression of a desaturase gene, or antisense desaturase transcripts, can alter the levels of specific PUFAs, or derivatives thereof, found in plant parts and/or plant tissues. The desaturase polypeptide coding region may be expressed either by itself or with other genes, in order to produce tissues and/or plant parts containing higher proportions of desired PUFAs or in which the PUFA composition more closely resembles that of human breast milk (Prieto et al., PCT publication WO 95/24494). The termination region may be derived from the 3' region of the gene from which the initiation region was obtained or from a different gene. A large number of termination regions are known to and have been found to be satisfactory in a variety of hosts from the same and different genera and species. The termination region usually is selected as a matter of convenience rather than because of any particular property.

As noted above, a plant (e.g., *Glycine max* (soybean) or *Brassica napus* (canola)) or plant tissue may also be utilized as a host or host cell, respectively, for expression of the desaturase enzyme which may, in turn, be utilized in the production of polyunsaturated fatty acids. More specifically, desired PUPAS can be expressed in seed. Methods of isolating seed oils are known in the art. Thus, in addition to providing a source for PUFAs, seed oil components may be manipulated through the expression of the desaturase gene, as well as perhaps other desaturase genes and elongase genes, in order to provide seed oils that can be added to nutritional compositions, pharmaceutical compositions, animal feeds and cosmetics. Once again, a vector which comprises a DNA sequence encoding the desaturase operably linked to a promoter, will be introduced into the plant tissue or plant for a time and under conditions sufficient for expression of the desaturase gene. The vector may also comprise one or more genes that encode other enzymes, for example, $\Delta 4$-desaturase, elongase, $\Delta 12$-desaturase, $\Delta 15$-desaturase, $\Delta 17$-desaturase, and/or $\Delta 19$-desaturase. The plant tissue or plant may produce the relevant substrate (e.g., DGLA (in the case of $\Delta 5$-desaturase), ALA (in the case of $\Delta 6$-desaturase), etc.) upon which the enzymes act or a vector encoding enzymes which produce such substrates may be introduced into the plant tissue, plant cell or plant. In addition, substrate may be sprayed on plant tissues expressing the appropriate enzymes. Using these various techniques, one may produce PUFAs (e.g., n-6 unsaturated fatty acids such as AA, or n-3 fatty acids such as EPA or STA) by use of a plant cell, plant tissue or plant. It should also be noted that the invention also encompasses a transgenic plant comprising the above-described vector, wherein expression of the nucleotide sequence of the vector results in production of a polyunsaturated fatty acid in, for example, the seeds of the transgenic plant.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens*, and obtaining transgenic plants have been published for cotton (U.S. Pat. Nos. 5,004,863, 5,159,135, 5,518, 908); soybean (U.S. Pat. Nos. 5,569,834, 5,416,011, McCabe et. al., *BiolTechnology* 6:923 (1988), Christou et al., *Plant Physiol.* 87:671–674 (1988)); *Brassica* (U.S. Pat. No. 5,463,174); peanut (Cheng et al., *Plant Cell Rep.* 15:653–657 (1996), McKently et al., *Plant Cell Rep.* 14:699–703 (1995)); papaya; and pea (Grant et al., *Plant Cell Rep.* 15:254–258, (1995)).

Transformation of monocotyledons using electroporation, particle bombardment, and *Agrobacterium* have also been reported. Transformation and plant regeneration have been achieved in asparagus (Bytebier et al., *Proc. Natl. Acad. Sci.* (USA) 84:5354, (1987)); barley (Wan and Lemaux, *Plant Physiol* 104:37 (1994)); *Zea mays* (Rhodes et al., *Science* 240:204 (1988), Gordon-Kamm et al., *Plant Cell* 2:603–618 (1990), Fromm et al., *BiolTechnology* 8:833 (1990), Koziel et al., *BiolTechnology* 11: 194, (1993), Armstrong et al., *Crop Science* 35:550–557 (1995)); oat (Somers et al., *BiolTechnology* 10: 15 89 (1992)); orchard grass (Horn et al., *Plant Cell Rep.* 7:469 (1988)); rice (Toriyama et al., *TheorAppl. Genet.* 205:34, (1986); Part et al., *Plant Mol. Biol.* 32:1135–1148, (1996); Abedinia et al., *Aust. J. Plant Physiol.* 24:133–141 (1997); Zhang and Wu, *Theor. Appl. Genet.* 76:835 (1988); Zhang et al. *Plant Cell Rep.* 7:379, (1988); Battraw and Hall, *Plant Sci.* 86:191–202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *BiolTechnology* 10:691 (1992)), and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454–457 (1988); Marcotte et al., *Plant Cell* 1:523–532 (1989); McCarty et al., *Cell* 66:895–905 (1991); Hattori et al., *Genes Dev.* 6:609–618 (1992); Goff et al., *EMBO J.* 9:2517–2522 (1990)).

Transient expression systems may be used to functionally dissect gene constructs (see generally, Maliga et al., Methods in Plant Molecular Biology, Cold Spring Harbor Press (1995)). It is understood that any of the nucleic acid molecules of the present invention can be introduced into a plant cell in a permanent or transient manner in combination with other genetic elements such as vectors, promoters, enhancers etc.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, N.Y. (1997)).

The substrates which may be produced by the host cell either naturally or transgenically, as well as the enzymes which may be encoded by DNA sequences present in the vector which is subsequently introduced into the host cell, are shown in FIG. 1.

In view of the above, the present invention encompasses a method of producing the desaturase enzymes (i.e., Δ5 or Δ6) comprising the steps of: 1) isolating the nucleotide sequence of the gene encoding the desaturase enzyme; 2) constructing a vector comprising said nucleotide sequence; and 3) introducing said vector into a host cell under time and conditions sufficient for the production of the desaturase enzyme.

The present invention also encompasses a method of producing polyunsaturated fatty acids comprising exposing an acid to the enzyme such that the desaturase converts the acid to a polyunsaturated fatty acid. For example, when 20:3n-6 is exposed to a Δ5-desaturase enzyme, it is converted to AA. AA may then be exposed to elongase which elongates the AA to adrenic acid (i.e., 22:4n-6). Alternatively, Δ5-desaturase may be utilized to convert 20:4n-3 to 20:5n-3 which may be exposed to elongase and converted to (n-3)-docosapentaenoic acid. The (n-3)-docosapentaenoic acid may then be converted to DHA by use of Δ4-desaturase. Thus, Δ5-desaturase may be used in the production of polyunsaturated fatty acids which may be used, in turn, for particular beneficial purposes.

With respect to the role of Δ6-desaturase, linoleic acid may be exposed to the enzyme such that the enzyme converts the acid to GLA. An elongase may then be used to convert the GLA to DGLA. The DGLA then may be converted to AA by exposing the DGLA to a Δ5-desaturase. As another example, ALA may be exposed to a Δ6desaturase in order to convert the ALA to STA. The STA may then be converted to 20:4n-3 by using an elongase. Subsequently, the 20:4n-3 may be converted to EPA by exposing the 20:4n-3 to a Δ5-desaturase. Thus, the Δ6-desaturase may be used in the production of PUFAs which have may advantageous properties or may be used in the production of other PUFAs.

Uses of the Δ5-Desaturases Genes, the Δ6Desaturase Genes, and Enzymes Encoded Thereby As noted above, the isolated desaturase genes and the desaturase enzymes encoded thereby have many uses. For example, the gene and corresponding enzyme may be used indirectly or directly in the production of polyunsaturated fatty acids, for example, Δ5-desaturase may be used in the production of AA, adrenic acid or EPA. Delta-6 desaturase may be used either indirectly or directly in the production of GLA, DGLA, STA or 20:4n-3. ("Directly" is meant to encompass the situation where the enzyme directly converts the acid to another acid, the latter of which is utilized in a composition (e.g., the conversion of DGLA to AA). "Indirectly" is meant to encompass the situation where an acid is converted to another acid (i.e., a pathway intermediate) by the desaturase (e.g., DGLA to AA) and then the latter acid is converted to another acid by use of a non-desaturase enzyme (e.g., AA to adrenic acid by elongase or by use of another desaturase enzyme (e.g., AA to EPA by Δ17-desaturase.)). These polyunsaturated fatty acids (i.e., those produced either directly or indirectly by activity of the desaturase enzyme) may be added to, for example, nutritional compositions, pharmaceutical compositions, cosmetics, and animal feeds, all of which are encompassed by the present invention. These uses are described, in detail, below.

Nutritional Compositions

The present invention includes nutritional compositions. Such compositions, for purposes of the present invention, include any food or preparation for human consumption including for enteral or parenteral consumption, which when taken into the body (a) serve to nourish or build up tissues or supply energy and/or (b) maintain, restore or support adequate nutritional status or metabolic function.

The nutritional composition of the present invention comprises at least one oil or acid produced directly or indirectly by use of the desaturase gene, in accordance with the present invention, and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany certain metabolic conditions (e.g., metabolic disorders).

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed search. Additionally, examples of proteins which may be utilized in the nutritional composition of the invention include but are not limited to soy proteins, electrodialysed whey, electrodialysed skim milk, milk whey, or the hydrolysates of these proteins.

With respect to vitamins and minerals, the following may be added to the nutritional compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the nutritional compositions of the present invention will be of semi-purified or purified origin. By semi-purified or purified is meant a material which has been prepared by purification of a natural material or by synthesis.

Examples of nutritional compositions of the present invention include but are not limited to infant formulas, dietary supplements, dietary substitutes, and rehydration compositions. Nutritional compositions of particular interest include but are not limited to those utilized for enteral and parenteral supplementation for infants, specialist infant formulas, supplements for the elderly, and supplements for those with gastrointestinal difficulties and/or malabsorption.

The nutritional composition of the present invention may also be added to food even when supplementation of the diet is not required. For example, the composition may be added to food of any type including but not limited to margarines, modified butters, cheeses, milk, yogurt, chocolate, candy, snacks, salad oils, cooking oils, cooking fats, meats, fish and beverages.

In a preferred embodiment of the present invention, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to polyunsaturated fatty acids produced in accordance with the present invention, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art. (See also the Examples below.)

The enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutritional formulas are well known in the art and are commercially available (e.g., Similac®, Ensure®, Jevity® and Alimentum® from Ross Products Division, Abbott Laboratories, Columbus, Ohio). An oil or acid produced in accordance with the present invention may be added to any of these formulas.

The energy density of the nutritional compositions of the present invention, when in liquid form, may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

The nutritional formula may include macronutrients, vitamins, and minerals, as noted above, in addition to the PUFAs produced in accordance with the present invention. The presence of these additional components helps the individual ingest the minimum daily requirements of these elements. In addition to the provision of PUFAs, it may also be desirable to add zinc, copper, folic acid and antioxidants to the composition. It is believed that these substance boost a stressed immune system and will therefore provide further benefits to the individual receiving the composition. A pharmaceutical composition may also be supplemented with these elements.

In a more preferred embodiment, the nutritional composition comprises, in addition to antioxidants and at least one PUFA, a source of carbohydrate wherein at least 5 weight percent of the carbohydrate is indigestible oligosaccharide. In a more preferred embodiment, the nutritional composition additionally comprises protein, taurine, and carnitine.

As noted above, the PUFAs produced in accordance with the present invention, or derivatives thereof, may be added to a dietary substitute or supplement, particularly an infant formula, for patients undergoing intravenous feeding or for preventing or treating malnutrition or other conditions or disease states. As background, it should be noted that human breast milk has a fatty acid profile comprising from about 0.15% to about 0.36% as DHA, from about 0.03% to about 0.13% as EPA, from about 0.30% to about 0.88% as AA, from about 0.22% to about 0.67% as DGLA, and from about 0.27% to about 1.04% as GLA. Thus, fatty acids such as AA, EPA and/or docosahexaenoic acid (DHA), produced in accordance with the present invention, can be used to alter, for example, the composition of infant formulas in order to better replicate the PUFA content of human breast milk or to alter the presence of PUFAs normally found in a non-human mammal's milk. In particular, a composition for use in a pharmacologic or food supplement, particularly a breast milk substitute or supplement, will preferably comprise one or more of AA, DGLA and GLA. More preferably, the oil will comprise from about 0.3 to 30% AA, from about 0.2 to 30% DGLA, and/or from about 0.2 to about 30% GLA.

Parenteral nutritional compositions comprising from about 2 to about 30 weight percent fatty acids calculated as triglycerides are encompassed by the present invention. The preferred composition has about 1 to about 25 weight percent of the total PUFA composition as GLA (U.S. Pat. No. 5,196,198). Other vitamins, particularly fat-soluble vitamins such as vitamin A, D, E and L-carnitine can optionally be included. When desired, a preservative such as alpha-tocopherol may be added in an amount of about 0.1% by weight.

In addition, the ratios of AA, DGLA and GLA can be adapted for a particular given end use. When formulated as a breast milk supplement or substitute, a composition which comprises one or more of AA, DGLA and GLA will be provided in a ratio of about 1:19:30 to about 6:1:0.2, respectively. For example, the breast milk of animals can vary in ratios of AA:DGLA:GLA ranging from 1:19:30 to 6:1:0.2, which includes intermediate ratios which are preferably about 1:1:1, 1:2:1, 1:1:4. When produced together in a host cell, adjusting the rate and percent of conversion of a precursor substrate such as GLA and DGLA to AA can be used to precisely control the PUFA ratios. For example, a 5% to 10% conversion rate of DGLA to AA can be used to produce an AA to DGLA ratio of about 1:19, whereas a conversion rate of about 75% TO 80% can be used to produce an AA to DGLA ratio of about 6:1. Therefore, whether in a cell culture system or in a host animal, regulating the timing, extent and specificity of desaturase expression, as well as the expression of other desaturases and elongases, can be used to modulate PUFA levels and ratios. The PUFAs/acids produced in accordance with the present invention (e.g., AA and EPA) may then be combined with other PUFAs/acids (e.g., GLA) in the desired concentrations and ratios. Additionally, PUFA produced in accordance with the present invention or host cells containing them may also be used as animal food supplements to alter an animal's tissue or milk fatty acid composition to one more desirable for human or animal consumption.

Pharmaceutical Compositions

The present invention also encompasses a pharmaceutical composition comprising one or more of the acids and/or resulting oils produced using the desaturase genes described herein, in accordance with the methods described herein. More specifically, such a pharmaceutical composition may comprise one or more of the acids and/or oils as well as a standard, well-known, non-toxic pharmaceutically acceptable carrier, adjuvant or vehicle such as, for example, phosphate buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectible, or topical ointment or cream. Proper fluidity can be maintained, for example, by the maintenance of the required particle size in the case of dispersions and by the use of surfactants. It may also be desirable to include isotonic agents, for example, sugars, sodium chloride and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art. For example, PUFAs produced in accordance with the present invention can be tabletted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant PUFA(s). The antioxidant and PUFA components should fit within the guidelines presented above.

For intravenous administration, the PUFAs produced in accordance with the present invention or derivatives thereof may be incorporated into commercial formulations such as Intralipids™. The typical normal adult plasma fatty acid profile comprises 6.64 to 9.46% of AA, 1.45 to 3.11% of DGLA, and 0.02 to 0.08% of GLA. These PUFAs or their metabolic precursors can be administered alone or in combination with other PUFAs in order to achieve a normal fatty acid profile in a patient. Where desired, the individual components of the formulations may be provided individually, in kit form, for single or multiple use. A typical dosage of a particular fatty acid is from 0.1 mg to 20 g (up to 100 g) daily and is preferably from 10 mg to 1, 2, 5 or 10 g daily.

Possible routes of administration of the pharmaceutical compositions of the present invention include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant. The route of administration will, of course, depend upon the desired effect. For example, if the composition is being utilized to treat rough, dry, or aging skin, to treat injured or burned skin, or to treat skin or hair affected by a disease or condition, it may perhaps be applied topically.

The dosage of the composition to be administered to the patient may be determined by one of ordinary skill in the art and depends upon various factors such as weight of the patient, age of the patient, immune status of the patient, etc.

With respect to form, the composition may be, for example, a solution, a dispersion, a suspension, an emulsion or a sterile powder which is then reconstituted.

The present invention also includes the treatment of various disorders by use of the pharmaceutical and/or nutritional compositions described herein. In particular, the compositions of the present invention may be used to treat restenosis after angioplasty. Furthermore, symptoms of inflammation, rheumatoid arthritis, asthma and psoriasis may also be treated with the compositions of the invention. Evidence also indicates that PUFAs may be involved in calcium metabolism; thus, the compositions of the present invention may, perhaps, be utilized in the treatment or prevention of osteoporosis and of kidney or urinary tract stones.

Additionally, the compositions of the present invention may also be used in the treatment of cancer. Malignant cells have been shown to have altered fatty acid compositions. Addition of fatty acids has been shown to slow their growth, cause cell death and increase their susceptibility to chemotherapeutic agents. Moreover, the compositions of the present invention may also be useful for treating cachexia associated with cancer.

The compositions of the present invention may also be used to treat diabetes (see U.S. Pat. No. 4,826,877 and Horrobin et al., *Am. J. Clin. Nutr.* Vol. 57 (Suppl.) 732S–737S). Altered fatty acid metabolism and composition have been demonstrated in diabetic animals.

Furthermore, the compositions of the present invention, comprising PUFAs produced either directly or indirectly through the use of the desaturase enzymes, may also be used in the treatment of eczema, in the reduction of blood pressure, and in the improvement of mathematics examination scores. Additionally, the compositions of the present invention may be used in inhibition of platelet aggregation, induction of vasodilation, reduction in cholesterol levels, inhibition of proliferation of vessel wall smooth muscle and fibrous tissue (Brenner et al., *Adv. Exp. Med. Biol.* Vol. 83, p. 85–101, 1976), reduction or prevention of gastrointestinal bleeding and other side effects of non-steroidal anti-inflammatory drugs (see U.S. Pat. No. 4,666,701), prevention or treatment of endometriosis and premenstrual syndrome (see U.S. Pat. No. 4,758,592), and treatment of myalgic encephalomyelitis and chronic fatigue after viral infections (see U.S. Pat. No. 5,116,871).

Further uses of the compositions of the present invention include use in the treatment of AIDS, multiple sclerosis, and inflammatory skin disorders, as well as for maintenance of general health.

Additionally, the composition of the present invention may be utilized for cosmetic purposes. It may be added to pre-existing cosmetic compositions such that a mixture is formed or may be used as a sole composition.

Veterinary Applications

It should be noted that the above-described pharmaceutical and nutritional compositions may be utilized in connection with animals (i.e., domestic or non-domestic), as well as humans, as animals experience many of the same needs and conditions as humans. For example, the oil or acids of the present invention may be utilized in animal or aquaculture feed supplements, animal feed substitutes, animal vitamins or in animal topical ointments.

The present invention may be illustrated by the use of the following non-limiting examples:

EXAMPLE 1

Design of Degenerate Oligonucleotides for the Isolation of Desaturases from Fungi and cDNA Library Construction Analysis of the fatty acid composition of *Saprolegnia diclina* (*S.diclina*) (ATCC 56851) revealed the presence of a considerable amount of arachidonic acid (ARA, 20:4 n-6) and eicosapentanoic acid (EPA, 20:5 n-3). Thus, it was thought that this organism contained an active Δ6-desaturase capable of converting linoleic acid (LA, 18:2 n-6) to gamma-linolenic acid (GLA, 18:3 n-6), and an active Δ5-desaturase that would convert dihomo-gamma-linolenic acid (DGLA, 20:3 n-6) to arachidonic acid (ARA, 20:4 n-6) (FIG. 1). In addition, it was thought that *S. diclina* also contained a Δ17-desaturase capable of desaturating ARA to EPA.

The fatty acid composition analysis of *Thraustochytrium aureum* (*T. aureum*) (ATCC 34304) revealed not only ARA and EPA but also longer chain PUFAs such as adrenic acid (ADA, 22:4n-6), ω6-docosapentaenoic acid (ω6-DPA, 22:5n-6), (ω3-docosapentaenoic acid (ω3-DPA, 22:5n-3), and docosahexaenoic acid (DHA, 22:6n-3). Thus, in addition to Δ6-, Δ5- and Δ17-desaturases, it was thought that *T. aureum* perhaps contained a Δ19-desaturase which converts ADA to ω3-DPA or ω6-DPA to DHA and/or a Δ4-desaturase which desaturates ADA to ω6-DPA or ω3-DPA to DHA. The goal thus was to attempt to isolate these predicted desaturase genes from *S.diclina* and *T. aureum,* and eventually to verify the functionality by expression in an alternate host.

To isolate genes encoding functional desaturase enzymes, a cDNA library was constructed for each organism. *Saprolegnia diclina* (ATCC 56851) cultures were grown in potato dextrose media Difco #336 (Difco Laboratories, Detroit, Mich.) at room temperature for 4 days with constant agitation. The mycelia were harvested by filtration through several layers of cheese cloth, and the cultures crushed in liquid nitrogen using a mortar and pestle. Total RNA was purified from it using the Qiagen RNeasy Maxi kit (Qiagen, Valencia, Calif.) as per manufacturer's protocol.

*T. aureum* (ATCC 34304) cells were grown in BY+ Media (Difco #790) at room temperature for 4 days, in the presence of light, and with constant agitation (250 rpm) to obtain the maximum biomass. These cells were harvested by centrifugation at 5000 rpm for 10 minutes and rinsed in ice-cold RNase-free water. These cells were then lysed in a French press at 10,000 psi, and the lysed cells directly collected into TE buffered phenol. Proteins from the cell lysate were removed by repeated phenol:chloroform (1:1 v/v) extraction, followed by a chloroform extraction. The nucleic acids from the aqueous phase were precipitated out at −70° C. for 30 minutes using 0.3M (final concentration) sodium acetate (pH 5.6) and one volume of isopropanol. The precipitated nucleic acids were collected by centrifugation at 15,000 rpm for 30 minutes at 4° C., vacuum-dried for 5 minutes and then treated with DNaseI (RNase-free) in 1×DNase buffer (20 mM Tris-Cl, pH 8.0; 5 mM $MgCl_2$) for 15 minutes at room temperature. The reaction was quenched with 5 mM EDTA (pH 8.0) and the RNA further purified using the Qiagen RNeasy Maxi kit (Qiagen, Valencia, Calif.) as per the manufacturer's protocol.

mRNA was isolated from total RNA from each organism using oligo dT cellulose resin. The pBluescript II XR library construction kit (Stratagene, La Jolla, Calif.) was then used to synthesize double stranded cDNA which was then directionally cloned (5' EcoRI/3' XhoI) into pBluescript II SK(+) vector. The *S.diclina* and *T. aureum* libraries contained approximately $2.5 \times 10^6$ clones each with an average insert size of approximately 700 bp. Genomic DNA from PUFA producing cultures of *S.diclina* and *T. aureum* was isolated by crushing the culture in liquid nitrogen and purified using Qiagen Genomic DNA Extraction Kit (Qiagen, Valencia, Calif.).

The approach taken was to design degenerate oligonucleotides (i.e., primers) that represent amino acid motifs that are conserved in known desaturases. These primers could be used in a PCR reaction to identify a fragment containing the conserved regions in the predicted desaturase genes from fungi. Since the only fungal desaturases identified are Δ5- and Δ6-desaturase genes from *Mortierella alpina* (Genbank accession numbers AF067650, AB020032, respectively), desaturase sequences from plants as well as animals were taken into consideration during the design of these degenerate primers. Known Δ5- and Δ6-desaturase sequences from the following organisms were used for the design of these degenerate primers: *Mortierella alpina, Borago officinalis, Helianthus annuus, Brassica napus, Dictyostelium discoideum, Rattus norvegicus, Mus musculus, Homo sapien, Caenorhabditis elegans, Arabidopsis thaliana,* and *Ricinus communis.* The degenerate primers used were as follows using the CODEHOP Blockmaker program (http://blocks.fhcrc.org/codehop.html):

A. Protein motif 1 (SEQ ID NO:53):
$NH_3$-VYDVTEWVKRHPGG —COOH
Primer RO 834 (SEQ ID NO:1):
5'-GTBTAYGAYGTBACCGARTGGGT-BAAGCGYCAYCCBGGHGGH-3'

B. Protein Motif 2 (SEQ ID NO:54):
$NH_3$-GASANWWKHQHNVHH —COOH
Primer RO835 (Forward) (SEQ ID NO:2):
5'-GGHGCYTCCGCYAACTGGTGGAAGCAY-CAGCAYAACGTBCAYCAY-3'
Primer RO836 (Reverse) (SEQ ID NO:3)
5'-RTGRTGVACGTTRTGCTGRTGCTTCCAC-CAGTTRGCGGARGCDCC-3'

C. Protein Motif 3 (SEQ ID NO:55):
$NH_3$-NYQIEHHLFPTM —COOH
Primer RO838 (Reverse) (SEQ ID NO:4)
5'-TTGATRGTCTARCTYGTRGTRGASAARG-GVTGGTAC-3'

In addition, two more primers were designed based on the 2nd and 3rd conserved 'Histidine-box' found in known Δ6-desaturases. These were:
Primer RO753 (SEQ ID NO:5)
5'-CATCATCATNGGRAANARRTGRTG-3'
Primer RO754 (SEQ ID NO:6)
5'-CTACTACTACTACAYCAYACNTAYACNAAY-3'

The degeneracy code for the oligonucleotide sequences was:
B=C,G,T; H=A,C,T; S=C,G; R=A,G; V=A,C,G; Y=C,T; D=A+T+C; N=A,C,G, or T/U, unknown or other

EXAMPLE 2

Isolation of Δ6-Desaturase Nucleotide Sequences from *Saprolegnia diclina* (ATCC 56851)

Total RNA from *Saprolegnia diclina* (ATCC 56851) was isolated using the lithium chloride method (Hoge, et al., *Exp. Mycology* (1982) 6:225–232). Five μg of the total RNA was reverse transcribed, using the SuperScript Preamplification system (LifeTechnologies, Rockville, Md.) and the oligo $(dT)_{12-18}$ primer supplied with the kit, to generate the first strand cDNA.

To isolate the Δ6-desaturase gene, various permutations and combinations of the above mentioned degenerate oligonucleotides were used in PCR reactions. Of the various primer sets tried, the only primers to give distinct bands were RO834/RO838. PCR amplification was carried out in a 100 μl volume containing: 2 μl of the first strand cDNA template, 20 mM Tris-HCl, pH 8.4, 50 mM KCl, 1.5 mM $MgCl_2$, 200 μM each deoxyribonucleotide triphosphate and 2 pmole of each primer. Thermocycling was carried out at two different annealing temperatures, 42° C. and 45° C., and these two PCR reactions were combined, resolved on a 1.0% agarose gel, and the band of ~1000 bp was gel purified using the QiaQuick Gel Extraction Kit (Qiagen, Valencia, Calif.). The staggered ends on these fragments were 'filled-in' using T4 DNA polymerase (LifeTechnologies, Rockville, Md.) as per manufacturer's specifications, and these DNA fragments were cloned into the PCR-Blunt vector (Invitrogen, Carlsbad, Calif.). The recombinant plasmids were transformed into TOP10 supercompetent cells (Invitrogen, Carlsbad, Calif.), and clones were sequenced.

Two clones were thus isolated that showed sequence homology to previously identified Δ6-desaturases. These clones are described as follows:
 a. Clone #20-2 was partially sequenced and the deduced amino acid sequence from 702 bp showed 30.2% identity with Δ6-desaturase from *Mortierella alpina* as the highest scoring match in a TfastA search.
 b. Clone #30-1 was partially sequenced, and the deduced amino acid sequence of 687 bp showed 48.5% amino acid identity with *Mortierella alpina*'s Δ6-desaturase as the highest scoring match in a TfastA search. These two sequences also overlapped each other indicating they belonged to a single putative Δ6-desaturase from *S. diclina*. This novel Δ6-desaturase sequence was then used to design primers to retrieve the 3'- and the 5'-end of the full-length Δ6-desaturase gene from the cDNA library generated from the mRNA of *S. diclina*.

To isolate the 3'-end, PCR amplification was carried out using plasmid DNA purified from the cDNA library as the template and oligonucleotides RO923 (SEQ ID NO:7) (5'-CGGTGCAGTGGTGGAAGAACAAGCACAAC-3') and RO899 (SEQ ID NO:8) (5'-AGCGGATAACAATTTCACA-CAGGAAACAGC-3'). Oligonucleotide RO923 was designed based on the #20-2 fragment of this putative Δ6-desaturase, and oligonucleotide RO899 corresponded to sequence from the pBluescript II SK(+) vector used for preparation of the cDNA library. Amplification was carried out using 10 pmols of each primer and the Taq PCR Master Mix (Qiagen, Valencia, Calif.). Samples were denatured initially at 94° C. for 3 minutes, followed by 30 cycles of the following: 94° C. for 1 minute, 60° C. for 1 minute, 72° C. for 2 minutes. A final extension cycle at 72° C. for 10 minutes was carried out before the reaction was terminated. The PCR fragments were resolved on a 0.8% agarose gel and gel purified using the Qiagen Gel Extraction Kit. The staggered end on these fragments were 'filled-in' using T4 DNA polymerase (LifeTechnologies, Rockville, Md.) as per manufacturer's specifications, and these DNA fragments were cloned into the PCR-Blunt vector (Invitrogen, Carlsbad, Calif.). The recombinant plasmids were transformed into TOP10 supercompetent cells (Invitrogen, Carlsbad, Calif.), and clones were sequenced. Clone sd2-2 contained a 958 bp insert which was identified to contain the 3'-end of the putative Δ6-gene based on sequence homology with known Δ6-desaturases and the presence of the 'TAA' stop codon and Poly A tail.

To isolate the 5'-end of this Δ6-desaturase from *Saprolegnia diclina*, the oligonucleotide RO939 (SEQ ID NO:9) (5'-CGTAGTACTGCTCGAGGAGCTTGAGCGCCG-3') was designed based on the sequence of the #30-1 fragment identified earlier. This oligonucleotide was used in combination with RO898 (SEQ ID NO:10) (5'-CCCAGTCAC-GACGTTGTAAAACGACGGCCAG-3') (designed based on the sequence of from the pBluescript SK(+) vector) to PCR amplify the 5'-end of the Δ6-desaturase from the cDNA library. In this case, the Advantage-GC cDNA PCR kit (Clonetech, Palo Alto, Calif.) was used to overcome PCR amplification problems that occur with GC rich regions, predicted to be present at the 5'-end of this Δ6-desaturase. PCR thermocycling conditions were as follows: The template was initially denatured at 94° C. for 1 minute, followed by 30 cycles of [94° C. for 30 seconds, 68° C. for 3 minutes], and finally an extension cycle at 68° C. for 5 minutes. The PCR products thus obtained were cloned into the PCR-Blunt vector (Invitrogen, Carlsbad, Calif.) following the same protocol as described above. Clone sd21-2 was thus obtained that contained a 360 bp insert that contained the putative 'ATG' start site of the novel Δ6-desaturase. The deduced amino acid sequence of this fragment, when aligned with known Δ6-desaturases showed 37–45% identity.

This novel Δ6-desaturase gene was isolated in its entirety by PCR amplification using, the *S. diclina* cDNA library, or *S. diclina* genomic DNA as a template, and the following oligonucleotides:
 a. RO 951 (SEQ ID NO:11)
  (5'-TCAACA<u>GAATTC</u>ATGGTCCAGGGGCAAAAGG-CCGAGAAGATCTCG-3') that contained sequence from the 5' end of clone sd21-2 as well as an EcoRI site (underlined) to facilitate cloning into a yeast expression vector
 b. RO960 (SEQ ID NO:12)
  (5'-ATACGT<u>AAGCTT</u>TTACATGGCGGGAAACTCCTTGAAGA-ACTCGATCG-3') that contained sequence from the 3' end of clone sd2–2 including the stop codon as well as a HindIII site (underlined) for cloning in an expression vector.

PCR amplification was carried out using 200 ng of the cDNA library plasmid template, 10 pmoles of each primer and the Taq PCR Master Mix (Qiagen, Valencia, Calif.), or 200 ng of genomic DNA, 10 pmoles of each primer, and the Advantage-GC cDNA PCR kit (Clonetech, Palo Alto, Calif.). Thermocycling conditions were as follows: the template was initially denatured at 94° C. for 1 minute, followed by 30 cycles of [94° C. for 30 seconds, 68° C. for 3 minutes], and finally an extension cycle at 68° C. for 5 minutes. The PCR product thus obtained was digested with EcoRI/HindIII and cloned into the yeast expression vector pYX242 (Invitrogen, Carlsbad, Calif.) to generate clones pRSP1 (genomic DNA-derived) and pRSP2 (library-derived) which were then sequenced and used for expression studies.

The Δ6-desaturase full-length gene insert was 1362 bp (SEQ ID NO:13, FIG. 2) in length and, beginning with the first ATG, contained an open reading frame encoding 453 amino acids. (The nucleotide sequence encoding the Δ6-desaturase was deposited as plasmid pRSP1 with the American Type Culture Collection (ATCC), 10801 University Boulevard, Manassas, Va. 20110 under the terms of the Budapest Treaty on Jan. 23, 2001 and was accorded accession number PTA-2829.) The amino acid sequence of the full-length gene (SEQ ID NO:14, FIG. 3) contained regions of homology to Δ6-desaturases from *Mortierella alpina*, *Caenorhabditis elegans* and *Borago officinalis*. It also contained the three conserved 'histidine boxes' found in all known membrane-bound desaturases (Okuley, et al. (1994) *The Plant Cell* 6: 147–158). These were present at amino acid positions 171–176, 208–212, and 391–395. As with other membrane-bound Δ6-desaturases, the third Histidine-box motif (HXXHH) in the *S. diclina* Δ6-desaturase was found to be QXXHH. This sequence also contained a cytochrome b5 domain at the 5'-end. This cytochrome b5 domain is found in a number of membrane-bound desaturase enzymes, and cytochrome b5 is thought to function as an electron donor in these enzymes. The presence of this domain may be advantageous when expressing the desaturase in heterologous systems for PUFA production. Since the proposed use of this gene is for the reconstruction of the PUFA biosynthetic pathway in plants, the base composition of this gene may be important. (It is known that some recombinant genes show poor expression because of variations in their base composition as compared to that of the host. The overall G+C content of this gene was 59%, which is close to that of the *M. alpina* desaturases that have been successfully expressed in plants.)

EXAMPLE 3

Isolation of Δ5-Desaturase Nucleotide Sequences from *Saprolegnia diclina* (ATCC 56851)

*Saprolegnia diclina* (ATCC 56851) produces both arachidonic acid (ARA, 20:4 n-6) and eicosapentanoic acid (EPA, 20:5 n-3); thus, it was thought to have, perhaps, a Δ5-desaturase which can convert dihomo-gamma-linolenic acid (DGLA, 20:3n-6) to arachidonic acid (ARA, 20:4 n-6). As with the Δ6-desaturase isolation, for the Δ5-desaturase isolation from *S. diclina*, various combinations of the degenerate primers were used in PCR reactions, using first strand cDNA as the template. The primer combination, RO753 and RO754, generated a distinct band of 588 bp using the following PCR conditions: 2 µl of the first strand cDNA template, 20 mM Tris-HCl, pH 8.4, 50 mM KCl, 1.5 mM MgCl$_2$, 200 µM each deoxyribonucleotide triphosphate, 2 pmole of each primer and 1U cDNA polymerase (Clonetech, Palo Alto, Calif.), in a final reaction volume of 50 µl. Thermocycling was carried out as follows: an initial denaturation at 94° C. for 3 minutes, followed by 35 cycles of: denaturation at 94° C. for 30 seconds, annealing at 60° C. for 30 seconds and extension at 72° C. for 1 minute. This was followed by a final extension at 72° C. for 7 minutes, and the reaction was terminated at 4° C. This fragment thus generated was cloned (clone #18-1), sequenced and, when translated, showed 43% amino acid identity with *Mortierella alpina* Δ5-desaturase (Genbank accession #AF067654) and 38.7% identity with *Dictyostelium discoideum* Δ5-desaturase (Genbank accession #AB029311). The second PCR fragment was identified using Primers RO834 and RO838 in the reaction described in Example 2. This fragment, of approximately 1000 bp in length, was cloned (Clone #20-8) and the deduced amino acid sequence derived from 775 bp showed 42% identity with Δ5-desaturase from *Dictyostelium discoideum* Δ5-desaturase (Genbank accession #AB029311). These two sequences, #18-1 and #20-8, overlapped each other indicating they belonged to a single putative Δ5-desaturase from *S. diclina*. These sequences were then used to design primers to retrieve the 3'- and the 5'-end of the novel Δ5-desaturase gene from the cDNA library generated from the mRNA of *S. diclina*.

To isolate the 3'-end of this putative Δ5-desaturase, PCR amplification was carried out using plasmid DNA purified from the cDNA library, as the template and oligonucleotides RO851 (SEQ ID NO:15) (5'-CCATCAAGACGTACCT-TGCGATC-3') and RO899 (SEQ ID NO:8) (5'-AGCG-GATAACAATTTCACACAGGAAACAGC-3'). Oligonucleotide RO851 was designed based on the #18-1 fragment of this putative Δ5desaturase, and oligonucleotide RO899 corresponded to sequence from the pBluescript II SK(+) vector. Amplification was carried out using 200 ng of template plasmid DNA, 10 pmoles of each primer and the Taq PCR Master Mix (Qiagen, Valencia, Calif.). Samples were denatured initially at 94° C. for 3 minutes, followed by 35 cycles of the following: 94° C. for 30 seconds, 60° C. for 30 seconds, 72° C. for 1 minutes. A final extension cycle at 72° C. for 7 minutes was carried out before the reaction was terminated. The PCR fragments were cloned into the PCR-Blunt vector (Invitrogen, Carlsbad, Calif.) as per the protocol described in Example 2. The recombinant plasmids were transformed into TOP10 supercompetent cells (Invitrogen, Carlsbad, Calif.), and clones were sequenced. Clone sd12-11 contained a 648 bp insert which contained the 3'-end of the putative Δ5-gene based on sequence homology with known Δ5-desaturases and the presence of the 'TAA' stop codon and polyA tail.

The 5'-end of this Δ5-desaturase from *Saprolegnia diclina* was isolated using primers RO941 and RO898. The oligonucleotide RO941 (SEQ ID NO:16) (5'-GCT-GAACGGGTGGTACGAGTCGAACGTG-3') was designed based on the sequence of the #20-8 fragment identified earlier. This oligonucleotide was used in combination with RO898 (SEQ ID NO:10) (5'-CCCAGTCAC-GACGTTGTAAAACGACGGCCAG-3') (designed based on the sequence of from the pBluescript II SK(+) vector) in a PCR amplification reaction using the cDNA library plasmid DNA as the template. Here the Advantage-GC cDNA PCR kit (Clonetech, Palo Alto, Calif.) was used as per the manufacturer's protocol, and the thermocycling conditions were as follows: an initial denaturation was carried out at 94° C. for 1 minute, followed by 30 cycles of [denaturation at 94° C. for 30 seconds, annealing and extension 68° C. for 3 minutes], and a final extension cycle at 68° C. for 5 minutes. These PCR products were purified, cloned into the PCR-Blunt vector (Invitrogen, Carlsbad, Calif.), and sequenced as described above. Clone sd24-1 was identified to contain a 295 bp insert that contained the putative 'ATG' start site of the novel Δ5-desaturase. Analysis of the deduced amino acid sequence of this fragment showed regions of high homology with known Δ5-desaturases and also the presence of a cytochrome b5 domain.

The full-length Δ5-desaturase gene was isolated by PCR amplification using *S. diclina* genomic DNA as a template and the following oligonucleotides:

a. RO 953 (SEQ ID NO:17)

(5'-ACGAGA<u>GAATTC</u>ATGGCCCCGCAGACGGAG-CTCCGCCAG CGC-3') that contained sequence from the 5' end of clone sd24-1 as well as an EcoRI site (underlined) to facilitate cloning into a yeast expression vector; and b. RO956 (SEQ ID NO:18)

(5'-AAAAGA<u>CTCGAG</u>TTAGCCCATGTGGATCGTG-GCGGCGATGCCC TGC-3') that contained sequence from the 3' end of clone sd12-11 including the stop codon as well as a XhoI site (underlined) for cloning in an expression vector.

Conditions for the PCR amplification of the 'full length' gene were similar to those described for the amplification of the Δ6-desaturase from genomic DNA (Example 2). The PCR product thus obtained was digested with EcoRII/XhoI and cloned into the yeast expression vector pYX242 (Invitrogen, Carlsbad, Calif.). Clone pRSP3 (genomic DNA-derived) was shown to contain a 1413 bp insert and was used for expression studies.

The 1413 bp full-length gene (SEQ ID NO:19, FIG. 4) of the putative Δ5-desaturase from *S. diclina* contained an open reading frame encoding 471 amino acids (SEQ ID NO:20, FIG. 5). (The nucleotide sequence encoding the Δ5-desaturase was deposited (as plasmid pRSP3) with the American Type Culture Collection, 10810 University Boulevard, Manassas, Va. 20110 under the terms of the Budapest Treaty on Jan. 23, 2001 and was accorded accession number PTA-2928.) This translated protein showed 40.5% overall identity with the *Mortierella alpina* Δ5-desaturasae (Genbank accession #AF067654) and 39.5% identity with the *Dictyostelium discoideum* Δ5-desaturase (Genbank accession #AB022097). It also contained the three conserved 'histidine boxes' at amino acid positions 186–190, 223–228, 406–410. Like the Δ6-desaturase, this sequence also contained a cytochrome b5 domain at the 5'-end. The overall G+C content of this gene was 61.5%.

EXAMPLE 4

Expression of *S. diclina* Desaturase Genes in Baker's Yeast

Clone pRSP2, which consisted of the full length Δ6-desaturase cloned into PYX242 (Invitrogen, Carlsbad, Calif.), and clone pRSP3, which consisted of the full-length Delta 5-desaturase gene in pYX242, were transformed into competent *Saccharomyces cerevisiae* strain 334. Yeast transformation was carried out using the Alkali-Cation Yeast Transformation Kit (BIO 101, Vista, Calif.) according to conditions specified by the manufacturer. Transformants were selected for leucine auxotrophy on media lacking leucine (DOB [-Leu]). To detect the specific desaturase activity of these clones, transformants were grown in the presence of 50 μM specific fatty acid substrates as listed below:
  a. Stearic acid (18:0) (conversion to oleic acid would indicate Δ9-desaturase activity)
  b. Oleic acid (18:1) (conversion to linoleic acid would indicated Δ12-desaturase activity)
  c. Linoleic acid (18:2 n-6) (conversion to alpha-linolenic acid would indicate Δ15-desaturase activity and conversion to gamma-linolenic acid would indicate Δ6-desaturase activity)
  d. Alpha-linolenic acid (18:3 n-3) (conversion to stearidonic acid would indicate Δ6-desaturase activity)
  e. Dihomo-gamma-linolenic acid (20:3 n-6) (conversion to arachidonic acid would indicate Δ5-desaturase activity).

The negative control strain was *S. cerevisiae* 334 containing the unaltered pYX242 vector, and these were grown simultaneously. The cultures were vigorously agitated (250 rpm) and grown for 48 hours at 24° C. in the presence of 50 μM (final concentration) of the various substrates. The cells were pelleted and vortexed in methanol; chloroform was added along with tritridecanoin (as an internal standard). These mixtures were incubated for at least an hour at room temperature or at 4° C. overnight. The chloroform layer was extracted and filtered through a Whatman filter with 1 gm anhydrous sodium sulfate to remove particulates and residual water. The organic solvents were evaporated at 40° C. under a stream of nitrogen. The extracted lipids were then derivitized to fatty acid methyl esters (FAME) for gas chromatography analysis (GC) by adding 2 ml of 0.5 N potassium hydroxide in methanol to a closed tube. The samples were heated to 95° C.–100° C. for 30 minutes and cooled to room temperature. Approximately 2 ml of 14% borontrifluoride in methanol were added and the heating repeated. After the extracted lipid mixture cooled, 2 ml of water and 1 ml of hexane were added to extract the FAME for analysis by GC. The percent conversion was calculated by dividing the product produced by the sum of (the product produced + the substrate added) and then multiplying by 100.

Table 1 represents the enzyme activity of the genes isolated based on the percent conversion of substrate added. The pRSP1 clone that contained the Δ6-desaturase gene from *S. diclina* converted 28% of the 18:2n-6 substrate to 18:3n-3, as well was 37% of the 18:3n-3 substrate to 18:4n-3. This confirms that the gene encodes a Δ6-desaturase. There was no background (non-specific conversion of substrate) in this case. (All tables referred to herein are presented after the Abstract of the Disclosure.)

The pRSP3 clone that contained the Δ5-desaturase gene from *S. diclina* was capable of converting 27% of the added 20:3n-6 substrate to 20:4n-6, indicating that the enzyme it encodes is a Δ5-desaturase. In this case too, there was no background substrate conversion detected. This data indicates that desaturases with different substrate specificity can be expressed in a heterologous system and can also be used to produce polyunsaturated fatty acids.

Table 2 represents fatty acids of interest as a percentage of the total lipid extracted from *S. cerevisiae* 334 with the indicated plasmid. No glucose was present in the growth media. Affinity gas chromatography was used to separate the respective lipids. GC/MS was employed to identify the products. From this table, it is apparent that exogenously added substrates, when added in the free form was taken up by the recombinant yeast and the incorporated into their membranes. In the yeast clone containing the Δ6-desaturase gene (pRSP1), GLA (γ-18:3) was identified as a novel PUFA when LA (18:2) was added as the substrate, and arachidonic acid was detected in yeast containing the Δ5-desaturase gene (pRSP3) when DGLA (20:3) was added as a substrate.

EXAMPLE 5

Co-Expression of *S. diclina* Desaturases with Elongases

The plasmid pRSP1 (Δ6) and pRSP3 (Δ5) were individually co-transformed with pRAE73-A3, a clone that contains the Human Elongase gene (SEQ ID NO:21) in the yeast expression vector pYES2, into yeast as described in Example 4. This elongase gene catalyzes some of the elongation steps in the PUFA pathway. Co-transformants were selected on minimal media lacking leucine and uracil (DOB[-Leu-Ura]).

Table 3 shows that when 50 μM of the substrate LA (18:2 n-6) was added, that the Δ6-desaturase converted this substrate to GLA (18:3 n-6) and the elongase was able to add two carbons to GLA to produce DGLA (20:3 n-6). The percent conversion of the substrate to the final product by these co-transformed enzymes is 26.4%, with no background observed from the negative control. Similarly, the co-transformed enzymes can act on ALA (18:3n-3) to finally form (20:4n-3) with a percentage conversion of 34.39%. Thus, *S. diclina* Δ6-desaturase was able to produce a product in a heterologous expression system that could be further utilized by another heterologous enzyme from the PUFA biosynthetic pathway to produce the expected PUFA.

Table 4 shows results of the pRSP3(Δ5)/Human Elongase co-transformation experiment. In this case, substrate GLA (18:3n-6) was converted to DGLA (20:3n-6) by human elongase and this was further converted to ARA (20:4n-6) by the action of *S. diclina* Δ5-desaturase. The percent conversion of the substrate to the final product by these co-transformed enzymes is 38.6%, with no background observed from the negative control.

The other substrate tested in this case was STA (18:4 n-3) which was eventually converted to EPA (20:5n-3) by the concerted action of the two enzymes. Similar results were observed when the pRSP1 and pRSP3 were cotransformed with an elongase gene derived from *M. alpina* (pRPB2)

(SEQ ID NO:22), and both genes were shown to be functional in the presence of each other (see Table 3 and Table 4).

EXAMPLE 6

Isolation of Δ5-Desaturase Nucleotide Sequences from *Thraustochytrium aureum* (ATCC 34303)

To isolate putative desaturase genes, total RNA was Isolated as described in Example 2. Approximately 5 μg was reverse transcribed using the SuperScript Preamplification system (LifeTechnologies, Rockville, Md.) as shown in Example 2 to produce first strand cDNA. Using the degenerate primers RO834 (SEQ ID NO:1) and 838 (SEQ ID NO:4) designed with the block maker program in a 50 μl reaction, the following components were combined: 2 μl of the first strand cDNA template, 20 mM Tris-HCl, pH 8.4, 50 mM KCl, 1.5 mM MgCl$_2$, 200 μM each deoxyribonucleotide triphosphate, 2 pmole final concentration of each primer and cDNA polymerase (Clonetech, Palo Alto, Calif.). Thermocycling was carried out as follows: an initial denaturation at 94° C. for 3 minutes, followed by 35 cycles of denaturation at 94° C. for 30 seconds, annealing at 60° C. for 30 seconds and extension at 72° C. for 1 minute. This was followed by a final extension at 72° C. for 7 minutes. Two faint bands of approximately 1000 bp were separated on a 1% agarose gel, excised, and purified with the QiaQuick Gel Extraction Kit (Qiagen, Valencia, Calif.). The ends were filled in with T4 DNA polymerase and the blunt-end fragments cloned into PCR Blunt as described in Example 2. Sequencing of the obtained clones identified the partial sequence of 680 bp from clone 30-9 whose translation of 226 amino acids had 31.5% identity with Δ6-desaturase from adult zebrafish (Genbank accession number AW281238). A similar degree of amino acid (29.6%–28.7%) homology was found with human Δ6-desaturase (Genbank accession number AF126799), *Physcomitrella patens* (moss) Δ6-desaturase (Genbank accession number AJ222980), *Brassica napus* (canola) Δ8-sphingolipid desaturase (Genbank accession number AJ224160), and human Δ5-desaturase (ATCC accession number 203557, Genbank accession number AF199596). Since there was a reasonable degree of amino acid homology to known desaturases, a full-length gene encoding a potential desaturase was sought to determine its activity when expressed in yeast.

To isolate the 3' end of the gene, 10 pmol of primer RO936 (SEQ ID NO:23) (5'-GTCGGGCAAGGCG-GAAAAGTACCTCAAGAG-3') and vector primer RO899 (SEQ ID NO:8) were combined in a reaction with 100 ng of purified plasmid from the *T. aureum* cDNA library in reaction volume of 100 μl in Taq PCR Master Mix (Qiagen, Valencia, Calif.). Thermocycling conditions were as follows: an initial melt at 94° C. for 3 minutes followed by 30 cycles of 94° C. for 1 minute, 60° C. for 1 minute, and 72° C. for 2 minutes. This was followed by an extension step of 10 minutes at 72° C. Several bands, including the predicted size of 1.2 kb, were separated on a 1% agarose gel and purified as stated earlier. Also as described earlier, the ends of the fragments were blunt ended, cloned into PCR Blunt and sequenced. Fragment #70-2 of approximately 1.2 kb was sequenced and contained an open reading frame and a stop codon, which overlapped fragment 30-9.

To isolate the 5' end of the gene, RO937 (SEQ ID NO:24) (5'-AAACCTGTAGACAATGTGGAGGGGCGTGGG-3') and RO 899 (SEQ ID NO:8) were used in a 50 μl PCR reaction with Advantage-GC cDNA PCR kit (Clonetech, Palo Alto, Calif.), as per the manufacturer's protocol, with 100 ng of purified plasmid DNA from the library and 10 pmol of each primer. The thermocycling conditions were as follows: An initial denaturation was carried out at 94° C. for 1 minute, followed by 30 cycles of [denaturation at 94° C. for 30 seconds, annealing and extension 68° C. for 3 minutes], and a final extension cycle at 68° C. for 5 minutes. A band of approximately 500 bp, in the range of the expected size, was gel purified, blunt ended and cloned into PCR Blunt as previously described. Clone 95-2 contained an open reading frame with a start codon. This fragment also overlapped with clone 30-9, indicating that they were indeed pieces of the same gene.

To isolate the full-length gene, primers were designed with restriction sites 5' and 3' (underlined) with EcoRI and XhoI, respectively, as follows: 5' primer RO972 (SEQ ID NO:25)(5'-ATACTT<u>GAATTC</u>ATGGGACGCGGCGGCG-AAGGTCAGGTGAAC-3'), 3' primer RO949 (SEQ ID NO: 26) (5'-CTTATA<u>CTCGAG</u>CTAAGCGG CCTTGGCCGC-CGCCTGGCC-3') and 3' primer RO950 (SEQ ID NO:27) (5'-CTTATA<u>CTCGAG</u>TAAATGGCTCGCGAGGCGAA-GCGAGTGGC-3'). Two primers were used for the 3' end of the gene in the initial isolation attempt since the primer RO949, containing the stop codon had 66% GC content, while the alternate primer RO950, which was outside the stop codon, had only a 56% GC content. A 50 μl PCR reaction with RO972/RO949 and RO972/950 was performed with Advantage-GC cDNA PCR kit (Clonetech, Palo Alto, Calif.) under identical conditions noted in the preceding paragraph. Only the primer set RO972/950 produced a band of approximately 1.6 kb. Use of genomic DNA as a template (under identical conditions with 100 ng of target) also produced a similar-sized band. Fragments were separated on an agarose gel, gel purified, blunt-ended and cloned into PCR Blunt as previously described. Fragments were evaluated by sequencing, and a number of clones were cut with EcoRI/XhoI to excise the full length gene, ligated to pYX242 EcoRI/XhoI which had been treated with shrimp alkaline phosphatase (Roche, Indianapolis, Ind.) with the Rapid ligation kit (Roche, Indianapolis, Ind.). Clone 99-3, designated pRTA4, contained the full length gene of 1317 bp (SEQ ID NO:28, FIG. 6) and an open reading frame of 439 aa (SEQ IN NO: 29, FIG. 7). (The nucleotide sequence encoding the Δ5-desaturase was deposited with the ATCC, 10801 University Boulevard, Manassas, Va. 20110 under the terms of the Budapest Treaty on Jan. 23, 2001 and was accorded accession number PTA-2927.) This gene contained three histidine boxes at amino acid numbers 171–175, 208–212, and 376–380. The 5'-end of the gene, when translated, also shows homology to cytochrome b5.

EXAMPLE 7

Expression of *T. aureum* Desaturase Gene in Baker's Yeast

The clone pRTA4 containing the full-length gene was transformed into the yeast host *S. cerevisiae* 334 and plated on selective media as described in Example 4. The cultures were grown at 24° C. for 48 hours in minimal media lacking leucine with 50 μM of exogenous free fatty acid added as a substrate as shown in Table 5. The only conversion of a substrate was DGLA (20:3n-6) to ARA (20:4n-6). The conversion of 23.7% of the added DGLA indicates that this gene encodes for a Δ5-desaturase.

Table 6 shows some of the fatty acids as a percentage of the lipid extracted from the yeast host. For Δ5-desaturase activity, there was no background (detection of ARA observed in the negative control containing the yeast expression plasmid, PYX242.)

EXAMPLE 8

Co-Expression of *T. aureum* Desaturase Gene with Elongases

The plasmid pRTA4 was co-transformed with an additional enzyme in the PUFA pathway, pRAE73-Δ3 which contains the human elongase gene in the yeast expression vector pYES2 as described in Example 4, and co-transformants were selected on minimal media lacking leucine and uracil.

Table 7 shows that when 100 μM of the substrate DGLA was added, that the Δ5desaturase actively produced ARA, to which the elongase was able to add two carbons to produce ADA. The percent conversion of *T. aureum* Δ5-desaturase, which consists of both ARA and ADA (products), was 16.7%, with no background observed from the negative control.

In view of the above results, *T. aureum* Δ5-desaturase is able to produce a product in a heterologous expression system that can be used by an additional heterologous enzyme in the PUFA biosynthetic pathway to produce the expected PUFA.

EXAMPLE 9

Isolation of Δ5desaturase Nucleotide Sequences from *Thraustochytrium aureum* BICC7091 (T7091)

A partial desaturase candidate was isolated using the degenerate primer combination of RO834/RO838, listed in Example 1. The genomic DNA was prepared from *Thraustochytrium aureum* BICC7091 (Biocon India Ltd., Bangalore, India) using the DNeasy plant maxi kit (Qiagen, Valencia, Calif.). The T7091 gDNA was amplified with primers RO834 (5'-GTB TAY GAY GTB ACC GAR TGG GTB AAG CGY CAY CCB GGH GGH-3') (SEQ ID NO:1) and RO838 (5'-CAT GGT VGG RAA SAG RTG RTG YTC RAT CTG RTA GTT-3') (SEQ ID NO:36). PCR amplification was carried out in a 100 μl volume containing: 5 μl of isolated T7091 gDNA, 0.2 M dNTP mix, 50 pM each primer, 10 μl of 10×buffer and 1.0 U of cDNA Polymerase. Thermocycler conditions in Perkin Elmer 9600 were as follows: 94° C. for 3 min, then 35 cycles of 94° C. for 30 sec., 60° C. for 30 sec., and 72° C. for 1 min. PCR was followed by an additional extension at 72° C. for 7 minutes. The PCR amplified mixture was run on a 1.0% agarose gel, and amplified fragments of approximately 1.2 Kb and 1.4 Kb were gel purified using the Qiaquick Gel Extraction Kit (Qiagen, Valencia, Calif.). The staggered ends on these fragments were filled-in using T4 DNA Polymerase (LifeTechnologies, Rockville, Md.), the isolated fragments were cloned into the pCR-Blunt vector (Invitrogen, Co., Carlsbad, Calif.), and the recombinant plasmids were transformed into TOP10 supercompetent cells (Invitrogen, Carlsbad, Calif.).

Twenty-four clones were prepared and sequenced using ABI 373A DNA Sequencer (Applied Biosystems, Foster City, Calif.). The translated sequences were used as queries to search the GenEmbl database (Genetics Computer Group (GCG) (Madison, Wis.)), using the tFastA algorithm (a Pearson and Lipman search for similarity between a protein query sequence and any group of nucleotide sequences). A gene fragment, T7091B2, was further pursued because it had identity with known desaturases. T7091B2 had 26.8% identity in 362 amino acids with Human Δ5-desaturase (GenBank accession number AF226273).

To isolate the 3' and 5'-ends, new primers were designed based on the T7091B2 internal sequence. The T7091 cDNA library, which contains approximately 2×10$^7$ clones with an average insert size of 1 Kb, was PCR amplified using the new primers and a vector primer. The primers that produced more 5' and 3' sequences with the vector primers RO898 (5'-CCC AGT CAC GAC GTT GTA AAA CGA CGG CCA G-3')(SEQ ID NO:10) and RO899 (5'-AGC GGA TAA CAA TTT CAC ACA GGA AAC AGC-3') (SEQ ID NO:8) were RO1065 (5'-CGA CAA GAG GAA GAG TGT CCA AAT C-3') (SEQ ID NO:37) and RO1064 (5'-CGC CTT CAA GAG TTT TTG TAC GGA ATT GGG-3')(SEQ ID NO:38), respectively, for clone T7091B2. Two new primers were designed based on the T7091B2 5' and 3' sequences:

a. RO1097 (5'-CTT GTA <u>CCA TGG</u> GTC GCG GAG CAC AGG GAG-3) (SEQ ID NO:39), which has an added NcoI restriction site (underlined)

b. RO1098 (5'-TG<u>A AGC TTA</u> CTC GCT CTT GGC AGC TTG GCC-3') (SEQ ID NO:40), which has an added HindIII restriction site (underlined)

This novel Δ5-desaturase gene was isolated in its entirely by PCR amplification, using the *T. aureum* 7091 gDNA. PCR was carried out in a 50 μl volume containing:

1 μl of isolated T7091 gDNA, 0.2 μM dNTP mix, 50 pM each primer, 5 μl of 10×buffer, 1.5 μl of 50 mM MgSO$_4$, and 0.5 U of Taq DNA Polymerase. Thermocycler conditions in Perkin Elmer 9600 were as follows: 94° C. for 3 min, then 30 cycles of 95° C. for 45 sec., 55° C. for 30 sec., and 68° C. for 2 min. The PCR amplified mixture was run on a gel, an amplified fragment of approximately 1.3 Kb was gel purified, and the isolated fragment was cloned into the pYX242(NcoI/EcoRV) vector. Two clones, designated as pRAT-2a and 2c, were prepared and sequenced. (Plasmid pRAT-2c was deposited with the American Type Culture Collection, 10801 University Blvd., Manassas, Va. 20110-2209 on Jan. 14, 2002 under the terms of the Budapest Treaty and was accorded ATCC deposit number PTA-3978.) The sequences were different by four amino acids (FIG. 12), and the translated sequence had 67.4% identity in 436 amino acids with *T. aureum* (ATCC34303) Δ5-desaturase (see Example 6).

EXAMPLE 10

Isolation of Δ6-desaturase Nucleotide Sequences from *Thraustochytrium aureum* BICC7091 (T7091)

Three hundred and seventy-three templates from the T7091 cDNA library were sequenced to determine the viability of the library. The translated sequences were used as queries to search the GenEmbl database using the tFastA algorithm. Clone 602187281R1 (or clone 281 for short) had identity with several known desaturases. The 5' and 3' ends of the EST clone were sequenced in order to design primers for amplification. Primers RO1107 (5'-TTT AA<u>C CAT GGG</u> CCG CGG CGG CGA GAA AAG-3') (SEQ ID NO:41), which has an added NcoI restriction site (underlined), and RO1108 (5'-GGG AAG <u>AAG CTT</u> TCT ACT GCG CCT TGG CTT TCT TTG-3') (SEQ ID NO:42), which has an added HindIII restriction site (underlined), were used to PCR amplify the T7091 gDNA.

PCR was carried out in a 50 μl volume with Taq DNA Polymerase as above. The PCR amplified mixture was run on a gel, an amplified fragment of approximately 1.3 Kb was gel purified, and the isolated fragment was cloned into the pYX242 (NcoI/EcoRV) vector. Two clones, designated as pRAT-1a and 1b, were prepared and sequenced. The sequences were different by one amino acid (FIG. 13), and the translated sequence had 25% identity in 430 amino acids with the Human Δ5-desaturase. (Plasmid pRAT-1A was deposited with the American Type Culture Collection, 10801 University Blvd., Manassas, Va. 20110-2209 on Jan. 14, 2002 under the terms of the Budapest Treaty and was accorded ATCC deposit number PTA-3977.)

EXAMPLE 11

Expression of *T. aureum* 7091 Desaturase Genes in Baker's Yeast

Clones pRAT-2a and pRAT-2c, which consisted of the full-length Δ5desaturase cloned into pYX242 (Invitrogen, Carlsbad, Calif.), and clones pRAT-1a and pRAT-1b, which consisted of the full-length Δ6-desaturase gene in pYX242, were transformed into competent *Saccharomyces cerevisiae* 334. Yeast transformation was carried out using the Alkali-Cation Yeast Transformation Kit (BIO 101, Vista, Calif.). Transformants were selected for leucine auxotrophy on media lacking leucine (DOB[-leu]). Because the translated sequence of pRAT-1 cDNA did not have a strong identity with any particular known desaturase, several fatty acid substrates were tested to determine the activity of the expressed enzyme. To detect the specific desaturase activity of pRAT-1a and pRAT-1b clones, transformants were grown in the presence of 100 μM specific fatty acid substrates as listed below:

a. Linoleic acid (LA, 18:2n-6) (conversion to α-linolenic acid would indicate Δ15-desaturase activity and conversion to γ-linolenic acid would indicate Δ6-desaturase activity)

b. α-linolenic acid (ALA, 18:3n-3) (conversion to stearidonic acid would indicate Δ6-desaturase activity)

c. ω6-eicosadienoic acid (EDA, 20:2n-6)(conversion to dihomo-γ-linolenic acid would indicate Δ8-desaturase activity)

d. dihomo-γ-linolenic acid (DGLA, 20:3n-6) (conversion to arachidonic acid would indicate Δ5-desaturase activity)

The substrate for pRAT-2 clones was 100 μM of DGLA. *S. cerevisiae* 334 containing the unaltered pYX242 vector was used as a negative control. Both pRAT-1a and pRAT-2c were also co-transformed into *S. cerevisiae* 334 with pRAE-73-A3 (i.e, a vector containing the human elongase enzyme which converts 18C fatty acids to 20C fatty acids, SEQ ID NO:21)(see Example 5). The substrates for pRAT-1a/pRAE-73-A3 clones were LA and ALA, and the substrates for pRAT-2c/pRAE-73-Δ3 clones were LA, ALA, and GLA. The cultures were grown for 48 hours at 24° C., in selective media, in the presence of a particular substrate. Fatty acid analyses were performed as outlined in Example 4.

Table 8 includes an example of the production of AA by strain 334(pRAT-2c) vs. that by the control strain 334 (pYX242). The amount of AA produced was 22.98%, vs. no detectable amount in the control strain. Strain 334(pRAT-2a) also had no detectable amount of AA produced (data not shown). The four amino acid difference between the two clones (FIG. 12, see underlined) rendered the enzyme expressed from strain 334(pRAT-2a) to be inactive. The Δ5-desaturase activity from clone pRAT-2c was further detected when co-expressed with pRAE-73-A3 in the presence of GLA.

Table 9 is the fatty acid analysis results of the strains 334(pRAT-1a) and 334(pYX242) expressed in the presence of substrates LA, ALA, EDA, and DGLA. The Δ6-desaturation of LA will produce GLA, the Δ8-desaturation of EDA will produce DGLA, and the Δ5-desaturation of DGLA will produce AA. All three activities were detected from both strains containing the T7091 gene vs. the control strain. Based on the conversion rates, this enzyme is an active Δ6-desaturase, which can behave like a Δ5- or Δ8-desaturase, given the proper substrates. However, the conversion rates of these substrates to their respective desaturated fatty acids are low, in comparison to the substrates for a Δ6-desaturation. The single amino acid difference between the two clones (FIG. 13, see underlined) had no affect on the enzymatic activity (data not shown). The percent conversions are shown in the lower box of Table 9. The Δ6-desaturase activity was further detected when pRAT-1a was co-expressed with pRAE-73-A3 in the presence of LA or ALA. The percent conversions were not calculated for the co-expression experiment, since it is difficult to determine whether the production of the new fatty acids is due to the activity of the desaturase, or elongase, or the combination of the two enzymes.

Two different methods of isolating a novel gene were explored in order to identify desaturase genes from *T. aureum* 7091. These methods led to the isolation of the T7091 Δ5-desaturase and Δ6-desaturase genes. In the presence of these genes and the appropriate substrates, *S. cerevisiae* produced desaturated fatty acids at a much higher level than the control strain. Co-transformation of the constructs containing the T7091B2 gene (pRAT-2c) and the Human elongase gene (pRAE-73-A3) in yeast resulted in the conversion of the substrate GLA to AA. This experiment confirmed that the enzyme expressed from pRAT-2c must desaturate the DGLA (produced by the elongase) to AA. Co-transformation of the constructs containing the "281" gene (pRAT-1a) and the Human elongase gene (pRAE-73-A3) in yeast resulted in the conversion of the substrate LA to DGLA. This experiment confirmed that the enzyme expressed from pRAT-1a must desaturate LA to GLA.

EXAMPLE 13

Isolation of Δ5-Desaturase Nucleotide Sequence from *Isochrysis galbana* 1323

A partial desaturase candidate was isolated using the degenerate primer combination of RO834/RO838, listed in Example 1. The genomic DNA was prepared from *Isochrysis galbana* CCMP1323 (Provasoli-Guillard National Center for the Culture of Marine Phytoplankton (CCMP), West Boothbay Harbor, Mass.) using the DNEASY™ plant maxi kit (Qiagen, Valencia, Calif.). The *I. galbana* gDNA was amplified with primers RO834 (5'-GTB TAY GAY GTB ACC GAR TGG GTB AAG CGY CAY CCB GGH GGH-3') (SEQ ID NO:1) and RO838 (5'-CAT GGT VGG RAA SAG RTG RTG YTC RAT CTG RTA GTT-3') (SEQ ID NO:10). PCR was carried out in a 50 μl volume containing: 1 μl of isolated *I. galbana* gDNA, 0.2 μM dNTP mix, 50 pM each primer, 5 μl of 10×buffer, 1.5 μl of 50 mM MgSO$_4$, and 0.5 U of Taq DNA Polymerase. Thermocycler conditions in Perkin Elmer 9600 were as follows: 94° C. for 3 min, then 30 cycles of 95° C. for 45 sec., 55° C. for 30 sec., and 68° C. for 2 min. The PCR amplified mixture was run on a 1.0% agarose gel, and an amplified fragment of approximately 1.1 Kb was gel purified using the QIAQUICK™ Gel Extraction Kit (Qiagen, Valencia, Calif.). The staggered ends of the fragment were filled-in using T4 DNA Polymerase (LifeTechnologies, Rockville, Md.), the isolated fragment was cloned into the pCR-Blunt vector (Invitrogen, Co., Carlsbad, Calif.), and the recombinant plasmids were transformed into TOP10 supercompetent cells (Invitrogen, Carlsbad, Calif.).

Six clones were prepared and sequenced using ABI 373A DNA Sequencer (Applied Biosystems, Foster City, Calif.). All of the sequences were the same. The translated sequence of the isolated fragment had 47.5% identity in 335 amino acids with with *T. aureum* (ATCC 34303) Δ5desaturase in clone pRTA4 (Example 6), and 45.3% identity in 278 amino acids with *T. aureum* BICC7091 Δ5-desaturase in clone pRAT-2c (Example 9).

To isolate the 5' and 3'-ends, new primers were designed based on the internal sequence of the isolated *I. galbana* fragment. For the 5 prime end of the gene RO1235 (5'-CGA AGT TGG TGA AGA TGT AGG TGC CG-3') (SEQ ID NO:43) was used, while RO1232 (5'-GAG CGA CGC GTA CAA CAA CTT TCA CGT-3') (SEQ ID NO:44) was used for the 3 prime end of the gene. Approximately 1.4 μg of total RNA was used, according to the manufacturer's direction, with the Rapid amplification of cDNA ends or RACE with the GENERACER™ kit (Invitrogen, Carlsbad, Calif.) and SUPERSCRIPT™ enzyme (Invitrogen, Carlsbad, Calif.) for reverse transcription to produce cDNA target. For the initial amplification of the ends, the following thermocycling protocol was used in a Perkin Elmer 9600: initial melt at 94° C. for 2 minutes; followed by 5 cycles of 94° C. for 30 seconds and 72° C. for 3 minutes; 10 cycles of 94° C. 30 seconds, 70° C. for 30 seconds, and 72° C. for 3 minutes; and 20 cycles of 94° C. for 30 seconds, 68° C. for 30 seconds and 72° C. for 3 minutes; followed by an extension of 72° C. for 10 minutes. This first PCR reaction was performed with 10 pMol of RO1235 or RO1232 and GENERACER™ 5 prime primer (5'-CGA CTG GAG CAC GAG GAC ACT GA-3') (SEQ ID NO:45),or GENERACER™ 3 prime primer (5'-GCT GTC AAC GAT ACG CTA CGT AAC G-3') (SEQ ID NO:46), respectively, with 1 1 of THERMOZYME™ (Invitrogen, Carlsbad, Calif.) and 1 μl of cDNA in a final volume of 50 μl, according to the manufacturer's directions.

A nested reaction was performed with 2 μl of the initial reaction, 10 pmol of nested primer RO1234 (5'-AGC TCC AGG TGA TTG TGC ACG CGC AG-3') (SEQ ID NO:47) or RO1233 (5'-GAC TTT GAG AAG CTG CGC CTC GAG CTG-3') (SEQ ID NO:48) and 30 pmol the GENERACER™ nested 5 prime primer (5'-GGA CAC TGA CAT GGA CTG AAG GAG TA-3') (SEQ ID NO:49) and GENERACER™ nested 3 prime primer (5'-CGC TAC GTA ACG GCA TGA CAG TG -3') (SEQ ID NO:50) respectively, and PLATINUM TAQ™ PCRx (Clonetech, Palo Alto, Calif.) using MgSO$_4$ according to the manufacturer's protocol. The thermocycling parameter was as follows in a Perkin Elmer 9600: initial melt at 94° C. for 2 minutes; followed by 5 cycles of 94° C. for 30 seconds and 72° C. for 2 minutes; 5 cycles of 94° C. 30 seconds, 70° C. for 2 minutes; 20 cycles of 94° C. for 30 seconds, 65° C. for 30 seconds and 68° C. for 2 minutes; followed by an extension of 68° C. for 10 minutes. Agarose gel analysis of the POR products showed a band around 800 base pairs for the 5 prime reactions and approximately a 1.2 kilobase band for 3 prime reaction. Subsequent cloning into pCR Blunt (Invitrogen, Carlsbad, Calif.), transformation into Top10 competent cells (Invitrogen, Carlsbad, Calif.), and sequencing, revealed an open reading frame with both a start and stop codons.

Primers RO1309 (5'-ATG ATG GAATTC ATG GTG GCA GGC AAA TCA GGC GC-3') (SEQ ID NO:51) and RO1310 (5'-AAT AAT GTCGAC CTA GTG CGT GTG CTC GTG GTA GG-3') (SEQ ID NO:52) with restrictions sites added for cloning (see underlined EcoRI, and SalI, respectively) were used to isolate a full length gene. As shown above, 10 pmol of primers RO1309 and 1310 were used with PLATINUM TAQ™ PCRx (Clonetech, Palo Alto, Calif.) using MgSO$_4$ according to the manufacturer's protocol, with 2 μl of the cONA as target. The thermocycling parameters were as follows: initial melt at 94° C. for 2 minutes; followed by 5 cycles of 94° C. for 30 seconds and 72° C. for 2 minutes; 5 cycles of 94° C. 30 seconds, 70° C. for 2 minutes; 20 cycles of 94° C. for 30 seconds, 65° C. for 30 seconds and 68° C. for 2 minutes; followed by an extension of 68° C. for 10 minutes. The single product of the reaction was gel purified using the QiaQuick gel purification kit (Qiagen, Valencia, Calif.), cut with EcoRI and SalI, ligated to pYX242 EcoRI/XhoI linearized DNA with the Rapid ligation kit (Roche, Indianapolis, Ind.), and designated pRTG-1. The clone pRIG-1 contained a full length gene of 1329 bp (SEQ ID NO:34; FIG. 14) and an open reading frame of 442 amino acid (SEQ ID NO:35; FIG. 15). (Plasmid pRIG-1 was deposited with the American Type Culture Collection, 10801 University Blvd., Manassas, Va. 20110-2209 on Jan. 14, 2002 under the terms of the Budapest Treaty and was accorded ATCC deposit number PTA-3979.)

EXAMPLE 14

Expression of *I. galbana* Desaturase Gene in Baker's Yeast

The clone pRIG-1 containing the full-length gene was transformed into the yeast host *S. cerevisiae* 334 and plated on selective media as described in Example 4. The cultures were grown at 24° C. for 48 hours in minimal media lacking leucine, with 50 μM of exogenous free fatty acid added as a substrate as shown in Table 10. The conversion of substrates was ETA (20:4n-3) to EPA (20:5n-3) and DGLA (20:3n-6) to AA (20:4n-6). The 45.4% conversion to ARA and 59.75% conversion to EPA indicate that this gene encodes for a Δ5-desaturase. Table 10 shows some of the fatty acids as a percentage of the lipid extracted from the yeast host. For Δ5-desaturase activity, there was little or no background (detection of ARA or EPA observed in the negative control containing the yeast expression plasmid, pYX242.)

EXAMPLE 15

Co-Expression of *I. galbana* Desaturase Gene with Elongases

The plasmid pRTG-1 could be co-transformed with an additional enzyme in the PUFA pathway, such as pRAE-73-A3 which contains the human elongase gene in the yeast expression vector pYES2 as described in Example 4, and co-transformants selected on minimal media lacking leucine and uracil. Substrates such as DGLA or ETA could be added so that the Δ5-desaturase would actively produced ARA or EPA, to which the elongase is able to add two carbons to produce ADA or ω3-DPA. Therefore, *I. galbana* Δ5-desaturase could produce a product in a heterologous expression system that can be used by an additional heterologous enzyme in the PUFA biosynthetic pathway, to produce the expected PUFA.

TABLE I

Percent amino acid identities shared between Δ6-desaturases and the *S. diclina* Δ6 desaturase

|  | *S. diclina* Δ6-desaturase |
|---|---|
| Phytium-Δ6 | 59% |
| Phaeodactylum tricornatum-Δ6 | 42% |
| Mucor-Δ6 | 39% |
| Rhizopus-Δ6 | 39% |
| Mortierella alpina-Δ6 | 39% |
| Physcomitrella patens-Δ6 | 33% |
| Ceratodon purpurens-Δ6 | 36% |
| Caenorhabditis elegans-Δ6 | 31% |
| Borage-Δ6 | 27% |
| Human-Δ6 | 27% |

TABLE II

Accession Numbers of the Listed Sequences:

| Sequence | Accession Number |
|---|---|
| Phytium-Δ6 | AAL13310 |
| Phaeodactylum tricornatum-Δ6 | AAL92563 |
| Mucor-Δ6 | BAB69055 |
| Rhizopus-Δ6 | AAP83964 |
| Mortierella alpina-Δ6 | AAF08685 |
| Physcomitrella patens-Δ6 | CAA11033 |
| Ceratodon purpurens-Δ6 | CAB94993 |
| Caenorhabditis elegans-Δ6 | AAC15586 |
| Borage-Δ6 | AAC49700 |
| Human-Δ6 | AAD20018 |

Nutritional Compositions

The PUFAs described in the Detailed Description may be utilized in various nutritional supplements, infant formulations, nutritional substitutes and other nutritional solutions.

I. Infant Formulations

A. Isomil® Soy Formula with Iron:

Usage: As a beverage for infants, children and adults with an allergy or sensitivity to cows milk. A feeding for patients with disorders for which lactose should be avoided: lactase deficiency, lactose intolerance and galactosemia.

Features:
  Soy protein isolate to avoid symptoms of cow's-milk-protein allergy or sensitivity.
  Lactose-free formulation to avoid lactose-associated diarrhea.
  Low osmolality (240 mOs/kg water) to reduce risk of osmotic diarrhea.
  Dual carbohydrates (corn syrup and sucrose) designed to enhance carbohydrate absorption and reduce the risk of exceeding the absorptive capacity of the damaged gut.
  1.8 mg of Iron (as ferrous sulfate) per 100 Calories to help prevent iron deficiency.
  Recommended levels of vitamins and minerals.
  Vegetable oils to provide recommended levels of essential fatty acids.
  Milk-white color, milk-like consistency and pleasant aroma.

Ingredients: (Pareve) 85% water, 4.9% corn syrup, 2.6% sugar (sucrose), 2.1% soy oil, 1.9% soy protein isolate, 1.4% coconut oil, 0.15% calcium citrate, 0. 11% calcium phosphate tribasic, potassium citrate, potassium phosphate monobasic, potassium chloride, mono- and disglycerides, soy lecithin, carrageenan, ascorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

B. Isomil® DF Soy Formula for Diarrhea:

Usage: As a short-term feeding for the dietary management of diarrhea in infants and toddlers.

Features:
  First infant formula to contain added dietary fiber from soy fiber specifically for diarrhea management.
  Clinically shown to reduce the duration of loose, watery stools during mild to severe diarrhea in infants.
  Nutritionally complete to meet the nutritional needs of the infant.
  Soy protein isolate with added L-methionine meets or exceeds an infant's requirement for all essential amino acids.
  Lactose-free formulation to avoid lactose-associated diarrhea.
  Low osmolality (240 mOsm/kg water) to reduce the risk of osmotic diarrhea.
  Dual carbohydrates (corn syrup and sucrose) designed to enhance carbohydrate absorption and reduce the risk of exceeding the absorptive capacity of the damaged gut.
  Meets or exceeds the vitamin and mineral levels recommended by the Committee on Nutrition of the American Academy of Pediatrics and required by the Infant Formula Act.
  1.8 mg of iron (as ferrous sulfate) per 100 Calories to help prevent iron deficiency.
  Vegetable oils to provide recommended levels of essential fatty acids.

Ingredients: (Pareve) 86% water, 4.8% corn syrup, 2.5% sugar (sucrose), 2.1% soy oil, 2.0% soy protein isolate, 1.4% coconut oil, 0.77% soy fiber, 0.12% calcium citrate, 0.11% calcium phosphate tribasic, 0.10% potassium citrate, potassium chloride, potassium phosphate monobasic, mono and diglycerides, soy lecithin, carrageenan, magnesium chloride, ascorbic acid, L-methionine, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

C. Isomil® SF Sucrose-Free Soy Formula with Iron:

Usage: As a beverage for infants, children and adults with an allergy or sensitivity to cow's-milk protein or an intolerance to sucrose. A feeding for patients with disorders for which lactose and sucrose should be avoided.

Features:
  Soy protein isolate to avoid symptoms of cow's-milk-protein allergy or sensitivity.
  Lactose-free formulation to avoid lactose-associated diarrhea (carbohydrate source is Polycose® Glucose Polymers).
  Sucrose free for the patient who cannot tolerate sucrose.
  Low osmolality (180 mOsm/kg water) to reduce risk of osmotic diarrhea.
  1.8 mg of iron (as ferrous sulfate) per 100 Calories to help prevent iron deficiency.
  Recommended levels of vitamins and minerals.
  Vegetable oils to provide recommended levels of essential fatty acids.
  Milk-white color, milk-like consistency and pleasant aroma.

Ingredients: (Pareve) 75% water, 11.8% hydrolized cornstarch, 4.1% soy oil, 4.1% soy protein isolate, 2.8% coconut oil, 1.0% modified cornstarch, 0.38% calcium phosphate tribasic, 0. 17% potassium citrate, 0.13% potassium chloride, mono- and diglycerides, soy lecithin, magnesium chloride, abscorbic acid, L-methionine, calcium carbonate, sodium chloride, choline chloride, carrageenan, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

D. Isomil® 20 Soy Formula with Iron Ready to Feed, 20 Cal/fl oz.:

Usage: When a soy feeding is desired.

Ingredients: (Pareve) 85% water, 4.9% corn syrup, 2.6% sugar (sucrose), 2.1% soy oil, 1.9% soy protein isolate, 1.4% coconut oil, 0.15% calcium citrate, 0. 11% calcium phosphate tribasic, potassium citrate, potassium phosphate monobasic, potassium chloride, mono- and diglycerides, soy lecithin, carrageenan, abscorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

E. Similac® Infant Formula:

Usage: When an infant formula is needed: if the decision is made to discontinue breastfeeding before age 1 year, if a supplement to breastfeeding is needed or as a routine feeding if breastfeeding is not adopted.

Features:
  Protein of appropriate quality and quantity for good growth; heat-denatured, which reduces the risk of milk-associated enteric blood loss.
  Fat from a blend of vegetable oils (doubly homogenized), providing essential linoleic acid that is easily absorbed.
  Carbohydrate as lactose in proportion similar to that of human milk.
  Low renal solute load to minimize stress on developing organs.
  Powder, Concentrated Liquid and Ready To Feed forms.

Ingredients: (-D) Water, nonfat milk, lactose, soy oil, coconut oil, mono- and diglycerides, soy lecithin, abscorbic acid, carrageenan, choline chloride, taurine, m-inositol, alpha-tocopheryl acetate, zinc sulfate, niacinamide, ferrous sulfate, calcium pantothenate, cupric sulfate, vitamin A palmitate, thiamine chloride hydrochloride, riboflavin, pyridoxine hydrochloride, folic acid, manganese sulfate, phylloquinone, biotin, sodium selenite, vitamin D3 and cyanocobalamin.

F. Similac® NeoCare Premature Infant Formula with Iron:

Usage: For premature infants' special nutritional needs after hospital discharge. Similac NeoCare is a nutritionally complete formula developed to provide premature infants with extra calories, protein, vitamins and minerals needed to promote catch-up growth and support development.

Features:
  Reduces the need for caloric and vitamin supplementation. More calories (22 Cal/fl oz) than standard term formulas (20 Cal/fl oz).
  Highly absorbed fat blend, with medium-chain triglycerides (MCToil) to help meet the special digestive needs of premature infants.
  Higher levels of protein, vitamins and minerals per 100 calories to extend the nutritional support initiated in-hospital.
  More calcium and phosphorus for improved bone mineralization.

Ingredients: -D Corn syrup solids, nonfat milk, lactose, whey protein concentrate, soy oil, high-oleic safflower oil, fractionated coconut oil (medium chain triglycerides), coconut oil, potassium citrate, calcium phosphate tribasic, calcium carbonate, ascorbic acid, magnesium chloride, potassium chloride, sodium chloride, taurine, ferrous sulfate, m-inositol, choline chloride, ascorbyl palmitate, L-carnitine, alpha-tocopheryl acetate, zinc sulfate, niacinamide, mixed tocopherols, sodium citrate, calcium pantothenate, cupric sulfate, thiamine chloride hydrochloride, vitamin A palmitate, beta carotene, riboflavin, pyridoxine hydrochloride, folic acid, manganese sulfate, phylloquinone, biotin, sodium selenite, vitamin D3 and cyanocobalamin.

G. Similac Natural Care Low-Iron Human Milk Fortifier Ready to Use, 24 Cal/fl oz.:

Usage: Designed to be mixed with human milk or to be fed alternatively with human milk to low-birth-weight infants.

Ingredients: -D Water, nonfat milk, hydrolyzed cornstarch, lactose, fractionated coconut oil (medium-chain triglycerides), whey protein concentrate, soy oil, coconut oil, calcium phosphate tribasic, potassium citrate, magnesium chloride, sodium citrate, ascorbic acid, calcium carbonate, mono and diglycerides, soy lecithin, carrageenan, choline chloride, m-inositol, taurine, niacinamide, L-carnitine, alpha tocopheryl acetate, zinc sulfate, potassium chloride, calcium pantothenate, ferrous sulfate, cupric sulfate, riboflavin, vitamin A palmitate, thiamine chloride hydrochloride, pyridoxine hydrochloride, biotin, folic acid, manganese sulfate, phylloquinone, vitamin D3, sodium selenite and cyanocobalamin.

Various PUFAs of this invention can be substituted and/or added to the infant formulae described above and to other infant formulae known to those in the art.

II. Nutritional Formulations

A. ENSURE®

Usage: ENSURE is a low-residue liquid food designed primarily as an oral nutritional supplement to be used with or between meals or, in appropriate amounts, as a meal replacement. ENSURE is lactose- and gluten-free, and is suitable for use in modified diets, including low-cholesterol diets. Although it is primarily an oral supplement, it can be fed by tube.

Patient Conditions:
  For patients on modified diets
  For elderly patients at nutrition risk
  For patients with involuntary weight loss
  For patients recovering from illness or surgery
  For patients who need a low-residue diet Ingredients: -D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate.

B. ENSURE® BARS:

Usage: ENSURE BARS are complete, balanced nutrition for supplemental use between or with meals. They provide a delicious, nutrient-rich alternative to other snacks. ENSURE BARS contain <1 g lactose/bar, and Chocolate Fudge Brownie flavor is gluten-free. (Honey Graham Crunch flavor contains gluten.)

Patient Conditions:
  For patients who need extra calories, protein, vitamins and minerals.
  Especially useful for people who do not take in enough calories and nutrients.
  For people who have the ability to chew and swallow
  Not to be used by anyone with a peanut allergy or any type of allergy to nuts.
  Ingredients: Honey Graham Crunch—High-Fructose Corn Syrup, Soy Protein Isolate, Brown Sugar, Honey, Maltodextrin (Corn), Crisp Rice (Milled Rice, Sugar [Sucrose], Salt [Sodium Chloride] and Malt), Oat Bran, Partially Hydrogenated Cottonseed and Soy Oils, Soy Polysaccharide, Glycerine, Whey Protein Concentrate, Polydextrose, Fructose, Calcium Caseinate, Cocoa Powder, Artificial Flavors, Canola Oil, High-Oleic Safflower Oil, Nonfat Dry Milk, Whey Powder, Soy Lecithin and Corn Oil. Manufactured in a facility that processes nuts.

Vitamins and Minerals: Calcium Phosphate Tribasic, Potassium Phosphate Dibasic, Magnesium Oxide, Salt (Sodium Chloride), Potassium Chloride, Ascorbic Acid, Ferric Orthophosphate, Alpha-Tocopheryl Acetate, Niacinamide, Zinc Oxide, Calcium Pantothenate, Copper Gluconate, Manganese Sulfate, Riboflavin, Beta Carotene, Pyridoxine Hydrochloride, Thiamine Mononitrate, Folic Acid, Biotin, Chromium Chloride, Potassium Iodide, Sodium Selenate, Sodium Molybdate, Phylloquinone, Vitamin D3 and Cyanocobalamin.

Protein: Honey Graham Crunch—The protein source is a blend of soy protein isolate and milk proteins.

| Soy protein isolate | 74% |
|---|---|
| Milk proteins | 26% |

Fat: Honey Graham Crunch—The fat source is a blend of partially hydrogenated cottonseed and soybean, canola, high oleic safflower, oils, and soy lecithin.

| Partially hydrogenated cottonseed and soybean oil | 76% |
|---|---|
| Canola oil | 8% |
| High-oleic safflower oil | 8% |
| Corn oil | 4% |
| Soy lecithin | 4% |

Carbohydrate: Honey Graham Crunch—The carbohydrate source is a combination of high-fructose corn syrup, brown sugar, maltodextrin, honey, crisp rice, glycerine, soy polysaccharide, and oat bran.

| High-fructose corn syrup | 24% |
|---|---|
| Brown sugar | 21% |
| Maltodextrin | 12% |
| Honey | 11% |
| Crisp rice | 9% |
| Glycerine | 9% |
| Soy Polysaccharide | 7% |
| Oat bran | 7% |

C. ENSURE® HIGH PROTEIN:

Usage: ENSURE HIGH PROTEIN is a concentrated, high-protein liquid food designed for people who require additional calories, protein, vitamins, and minerals in their diets. It can be used as an oral nutritional supplement with or between meals or, in appropriate amounts, as a meal replacement. ENSURE HIGH PROTEIN is lactose- and gluten-free, and is suitable for use by people recovering from general surgery or hip fractures and by patients at risk for pressure ulcers.

Patient Conditions:
  For patients who require additional calories, protein, vitamins, and minerals, such as patients recovering from general surgery or hip fractures, patients at risk for pressure ulcers, and patients on low-cholesterol diets.

Features:
  Low in saturated fat
  Contains 6 g of total fat and <5 mg of cholesterol per serving
  Rich, creamy taste
  Excellent source of protein, calcium, and other essential vitamins and minerals
  For low-cholesterol diets
  Lactose-free, easily digested Ingredients:

Vanilla Supreme: -D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate, Phylloquinone, Vitamin D3 and Cyanocobalamin.

Protein:

The protein source is a blend of two high-biologic-value proteins: casein and soy.

| | |
|---|---|
| Sodium and calcium caseinates | 85% |
| Soy protein isolate | 15% |

Fat:

The fat source is a blend of three oils: high-oleic safflower, canola, and soy.

| | |
|---|---|
| High-oleic safflower oil | 40% |
| Canola oil | 30% |
| Soy oil | 30% |

The level of fat in ENSURE HIGH PROTEIN meets American Heart Association (AHA) guidelines. The 6 grams of fat in ENSURE HIGH PROTEIN represent 24% of the total calories, with 2.6% of the fat being from saturated fatty acids and 7.9% from polyunsaturated fatty acids. These values are within the AHA guidelines of <30% of total calories from fat, <10% of the calories from saturated fatty acids, and <10% of total calories from polyunsaturated fatty acids.

Carbohydrate:

ENSURE HIGH PROTEIN contains a combination of maltodextrin and sucrose. The mild sweetness and flavor variety (vanilla supreme, chocolate royal, wild berry, and banana), plus VARI-FLAVORS® Flavor Pacs in pecan, cherry, strawberry, lemon, and orange, help to prevent flavor fatigue and aid in patient compliance.

Vanilla and other Nonchocolate Flavors:

| | |
|---|---|
| Sucrose | 60% |
| Maltodextrin | 40% |
| Chocolate: | |
| Sucrose | 70% |
| Maltodextrin | 30% |

D. ENSURE® LIGHT

Usage: ENSURE LIGHT is a low-fat liquid food designed for use as an oral nutritional supplement with or between meals. ENSURE LIGHT is lactose- and gluten-free, and is suitable for use in modified diets, including low-cholesterol diets.

Patient Conditions:

For normal-weight or overweight patients who need extra nutrition in a supplement that contains 50% less fat and 20% fewer calories than ENSURE.

For healthy adults who do not eat right and need extra nutrition.

Features:

Low in fat and saturated fat

Contains 3 g of total fat per serving and <5 mg cholesterol

Rich, creamy taste

Excellent source of calcium and other essential vitamins and minerals

For low-cholesterol diets

Lactose-free, easily digested

Ingredients:

French Vanilla: -D Water, Maltodextrin (Corn), Sugar (Sucrose), Calcium Caseinate, High-Oleic Safflower Oil, Canola Oil, Magnesium Chloride, Sodium Citrate, Potassium Citrate, Potassium Phosphate Dibasic, Magnesium Phosphate Dibasic, Natural and Artificial Flavor, Calcium Phosphate Tribasic, Cellulose Gel, Choline Chloride, Soy Lecithin, Carrageenan, Salt (Sodium Chloride), Ascorbic Acid, Cellulose Gum, Ferrous Sulfate, Alpha-Tocopheryl Acetate, Zinc Sulfate, Niacinamide, Manganese Sulfate, Calcium Pantothenate, Cupric Sulfate, Thiamine Chloride Hydrochloride, Vitamin A Palmitate, Pyridoxine Hydrochloride, Riboflavin, Chromium Chloride, Folic Acid, Sodium Molybdate, Biotin, Potassium Iodide, Sodium Selenate, Phylloquinone, Vitamin D3 and Cyanocobalamin.

Protein:

The protein source is calcium caseinate.

| | |
|---|---|
| Calcium caseinate | 100% |

Fat:

The fat source is a blend of two oils: high-oleic safflower and canola.

| | |
|---|---|
| High-oleic safflower oil | 70% |
| Canola oil | 30% |

The level of fat in ENSURE LIGHT meets American Heart Association (AHA) guidelines. The 3 grams of fat in ENSURE LIGHT represent 13.5% of the total calories, with 1.4% of the fat being from saturated fatty acids and 2.6% from polyunsaturated fatty acids. These values are within the AHA guidelines of <30% of total calories from fat, <10% of the, calories from saturated fatty acids, and <10% of total calories from polyunsaturated fatty acids.

Carbohydrate:

ENSURE LIGHT contains a combination of maltodextrin and sucrose. The chocolate flavor contains corn syrup as well. The mild sweetness and flavor variety (French vanilla, chocolate supreme, strawberry swirl), plus VARI-FLAVORS® Flavor Pacs in pecan, cherry, strawberry, lemon, and orange, help to prevent flavor fatigue and aid in patient compliance.

Vanilla and other Nonchocolate Flavors:

| | |
|---|---|
| Sucrose | 51% |
| Maltodextrin | 49% |

Chocolate:

| | |
|---|---|
| Sucrose | 47.0% |
| Corn Syrup | 26.5% |
| Maltodextrin | 26.5% |

Vitamins and Minerals:

An 8-fl-oz serving of ENSURE LIGHT provides at least 25% of the RDIs for 24 key vitamins and minerals.

Caffeine:

Chocolate flavor contains 2.1 mg caffeine/8 fl oz.

E. ENSURE PLUS®

Usage: ENSURE PLUS is a high-calorie, low-residue liquid food for use when extra calories and nutrients, but a normal concentration of protein, are needed. It is designed primarily as an oral nutritional supplement to be used with or between meals or, in appropriate amounts, as a meal replacement. ENSURE PLUS is lactose- and gluten-free. Although it is primarily an oral nutritional supplement, it can be fed by tube.

Patient Conditions:

For patients who require extra calories and nutrients, but a normal concentration of protein, in a limited volume.

For patients who need to gain or maintain healthy weight.

Features:

Rich, creamy taste

Good source of essential vitamins and minerals

Ingredients:

Vanilla: -D Water, Corn Syrup, Maltodextrin (Corn), Corn Oil, Sodium and Calcium Caseinates, Sugar (Sucrose), Soy Protein Isolate, Magnesium Chloride, Potassium Citrate, Calcium Phosphate Tribasic, Soy Lecithin, Natural and Artificial Flavor, Sodium Citrate, Potassium Chloride, Choline Chloride, Ascorbic Acid, Carrageenan, Zinc Sulfate, Ferrous Sulfate, Alpha-Tocopheryl Acetate, Niacinamide, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

Protein:

The protein source is a blend of two high-biologic-value proteins: casein and soy.

| | |
|---|---|
| Sodium and calcium caseinates | 84% |
| Soy protein isolate | 16% |

Fat:

The fat source is corn oil.

| | |
|---|---|
| Corn oil | 100% |

Carbohydrate:

ENSURE PLUS contains a combination of maltodextrin and sucrose. The mild sweetness and flavor variety (vanilla, chocolate, strawberry, coffee, buffer pecan, and eggnog), plus VARI-FLAVORS® Flavor Pacs in pecan, cherry, strawberry, lemon, and orange, help to prevent flavor fatigue and aid in patient compliance.

Vanilla, Strawberry, Butter Pecan, and Coffee Flavors:

| | |
|---|---|
| Corn Syrup | 39% |
| Maltodextrin | 38% |
| Sucrose | 23% |

Chocolate and Eggnog Flavors:

| | |
|---|---|
| Corn Syrup | 36% |
| Maltodextrin | 34% |
| Sucrose | 30% |

Vitamins and Minerals:

An 8-fl-oz serving of ENSURE PLUS provides at least 15% of the RDIs for 25 key Vitamins and minerals.

Caffeine:

Chocolate flavor contains 3.1 mg Caffeine/8 fl oz. Coffee flavor contains a trace amount of caffeine.

F. ENSURE PLUS® HN

Usage: ENSURE PLUS HN is a nutritionally complete high-calorie, high-nitrogen liquid food designed for people with higher calorie and protein needs or limited volume tolerance. It may be used for oral supplementation or for total nutritional support by tube. ENSURE PLUS HN is lactose- and gluten-free.

Patient Conditions:

For patients with increased calorie and protein needs, such as following surgery or injury.

For patients with limited volume tolerance and early satiety.

Features:

For supplemental or total nutrition

For oral or tube feeding 1.5 CaVmL,

High nitrogen

Calorically dense

Ingredients:

Vanilla: -D Water, Maltodextrin (Corn), Sodium and Calcium Caseinates, Corn Oil, Sugar (Sucrose), Soy Protein Isolate, Magnesium Chloride, Potassium Citrate, Calcium Phosphate Tribasic, Soy Lecithin, Natural and Artificial Flavor, Sodium Citrate, Choline Chloride, Ascorbic Acid, Taurine, L-Carnitine, Zinc Sulfate, Ferrous Sulfate, Alpha- Tocopheryl Acetate, Niacinamide, Carrageenan, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

G. ENSURE® POWDER:

Usage: ENSURE POWDER (reconstituted with water) is a low-residue liquid food designed primarily as an oral nutritional supplement to be used with or between meals. ENSURE POWDER is lactose- and gluten-free, and is suitable for use in modified diets, including low-cholesterol diets.

Patient Conditions:
  For patients on modified diets
  For elderly patients at nutrition risk
  For patients recovering from illness/surgery
  For patients who need a low-residue diet Features:
  Convenient, easy to mix
  Low in saturated fat
  Contains 9 g of total fat and <5 mg of cholesterol per serving
  High in vitamins and minerals
  For low-cholesterol diets
  Lactose-free, easily digested Ingredients: -D Corn Syrup, Maltodextrin (Corn), Sugar (Sucrose), Corn Oil, Sodium and Calcium Caseinates, Soy Protein Isolate, Artificial Flavor, Potassium Citrate, Magnesium Chloride, Sodium Citrate, Calcium Phosphate Tribasic, Potassium Chloride, Soy Lecithin, Ascorbic Acid, Choline Chloride, Zinc Sulfate, Ferrous Sulfate, Alpha-Tocopheryl Acetate, Niacinamide, Calcium Pantothenate, Manganese Sulfate, Thiamine Chloride Hydrochloride, Cupric Sulfate, Pyridoxine Hydrochloride, Riboflavin, Vitamin A Palmitate, Folic Acid, Biotin, Sodium Molybdate, Chromium Chloride, Potassium Iodide, Sodium Selenate, Phylloquinone, Vitamin D3 and Cyanocobalamin.

Protein:

The protein source is a blend of two high-biologic-value proteins: casein and soy.

| | |
|---|---|
| Sodium and calcium caseinates | 84% |
| Soy protein isolate | 16% |

Fat:
  The fat source is corn oil.

| | |
|---|---|
| Corn oil | 100% |

Carbohydrate:

ENSURE POWDER contains a combination of corn syrup, maltodextrin, and sucrose. The mild sweetness of ENSURE POWDER, plus VARI-FLAVORS® Flavor Pacs in pecan, cherry, strawberry, lemon, and orange, helps to prevent flavor fatigue and aid in patient compliance.

Vanilla:

| | |
|---|---|
| Corn Syrup | 35% |
| Maltodextrin | 35% |
| Sucrose | 30% |

H. ENSURE® PUDDING

Usage: ENSURE PUDDING is a nutrient-dense supplement providing balanced nutrition in a nonliquid form to be used with or between meals. It is appropriate for consistency-modified diets (e.g., soft, pureed, or full liquid) or for people with swallowing impairments. ENSURE PUDDING is gluten-free.

Patient Conditions:
  For patients on consistency-modified diets (e.g., soft, pureed, or full liquid)
  For patients with swallowing impairments Features:
  Rich and creamy, good taste
  Good source of essential vitamins and minerals
  Convenient-needs no refrigeration
  Gluten-free Nutrient Profile per 5 oz: Calories 250, Protein 10.9%, Total Fat 34.9%, Carbohydrate 54.2%

Ingredients:

Vanilla: -D Nonfat Milk, Water, Sugar (Sucrose), Partially Hydrogenated Soybean Oil, Modified Food Starch, Magnesium Sulfate, Sodium Stearoyl Lactylate, Sodium Phosphate Dibasic, Artificial Flavor, Ascorbic Acid, Zinc Sulfate, Ferrous Sulfate, Alpha-Tocopheryl Acetate, Choline Chloride, Niacinamide, Manganese Sulfate, Calcium Pantothenate, FD&C Yellow #5, Potassium Citrate, Cupric Sulfate, Vitamin A Palmitate, Thiamine Chloride Hydrochloride, Pyridoxine Hydrochloride, Riboflavin, FD&C Yellow #6, Folic Acid, Biotin, Phylloquinone, Vitamin D3 and Cyanocobalamin.

Protein:
  The protein source is nonfat milk.

| | |
|---|---|
| Nonfat milk | 100% |

Fat:
  The fat source is hydrogenated soybean oil.

| | |
|---|---|
| Hydrogenated soybean oil | 100% |

Carbohydrate:

ENSURE PUDDING contains a combination of sucrose and modified food starch. The mild sweetness and flavor variety (vanilla, chocolate, butterscotch, and tapioca) help prevent flavor fatigue. The product contains 9.2 grams of lactose per serving.

Vanilla and other Nonchocolate Flavors:

| Sucrose | 56% |
|---|---|
| Lactose | 27% |
| Modified food starch | 17% |

Chocolate:

| Sucrose | 58% |
|---|---|
| Lactose | 26% |
| Modified food starch | 16% |

I. ENSURE® WITH FIBER:

Usage: ENSURE WITH FIBER is a fiber-containing, nutritionally complete liquid food designed for people who can benefit from increased dietary fiber and nutrients. ENSURE WITH FIBER is suitable for people who do not require a low-residue diet. It can be fed orally or by tube, and can be used as a nutritional supplement to a regular diet or, in appropriate amounts, as a meal replacement. ENSURE WITH FIBER is lactose- and gluten-free, and is suitable for use in modified diets, including low-cholesterol diets.

Patient Conditions:
  For patients who can benefit from increased dietary fiber and nutrients Features:
  New advanced formula-low in saturated fat, higher in vitamins and minerals
  Contains 6 g of total fat and <5 mg of cholesterol per serving
  Rich, creamy taste
  Good source of fiber
  Excellent source of essential vitamins and minerals
  For low-cholesterol diets
  Lactose- and gluten-free Ingredients:

Vanilla: -D Water; Maltodextrin (Corn), Sugar (Sucrose), Sodium and Calcium Caseinates, Oat Fiber, High-Oleic Safflower Oil, Canola Oil, Soy Protein Isolate, Corn Oil, Soy Fiber, Calcium Phosphate Tribasic, Magnesium Chloride, Potassium Citrate, Cellulose Gel, Soy Lecithin, Potassium Phosphate Dibasic, Sodium Citrate, Natural and Artificial Flavors, Choline Chloride, Magnesium Phosphate, Ascorbic Acid, Cellulose Gum, Potassium Chloride, Carrageenan, Ferrous Sulfate, Alpha-Tocopheryl Acetate, Zinc Sulfate, Niacinamide, Manganese Sulfate, Calcium Pantothenate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Potassium Iodide, Sodium Selenate, Phylloquinone, Vitamin D3 and Cyanocobalamin.

Protein:

The protein source is a blend of two high-biologic-value proteins-casein and soy.

| Sodium and calcium caseinates | 80% |
|---|---|
| Soy protein isolate | 20% |

Fat:

The fat source is a blend of three oils: high-oleic safflower, canola, and corn.

| High-oleic safflower oil | 40% |
|---|---|
| Canola oil | 40% |
| Corn oil | 20% |

The level of fat in ENSURE WITH FIBER meets American Heart Association (AHA) guidelines. The 6 grams of fat in ENSURE WITH FIBER represent 22% of the total calories, with 2.01% of the fat being from saturated fatty acids and 6.7% from polyunsaturated fatty acids. These values are within the AHA guidelines of $\leq 30\%$ of total calories from fat, <10% of the calories from saturated fatty acids, and $\leq 10\%$ of total calories from polyunsaturated fatty acids.

Carbohydrate:

ENSURE WITH FIBER contains a combination of maltodextrin and sucrose. The mild sweetness and flavor variety (vanilla, chocolate, and butter pecan), plus VARI-FLAVORSO Flavor Pacs in pecan, cherry, strawberry, lemon, and orange, help to prevent flavor fatigue and aid in patient compliance.

Vanilla and other Nonchocolate Flavors:

| Maltodextrin | 66% |
|---|---|
| Sucrose | 25% |
| Oat Fiber | 7% |
| Soy Fiber | 2% |

Chocolate:

| Maltodextrin | 55% |
|---|---|
| Sucrose | 36% |
| Oat Fiber | 7% |
| Soy Fiber | 2% |

Fiber:

The fiber blend used in ENSURE WITH FIBER consists of oat fiber and soy polysaccharide. This blend results in approximately 4 grams of total dietary fiber per 8-fl. oz can. The ratio of insoluble to soluble fiber is 95:5.

The various nutritional supplements described above and known to others of skill in the art can be substituted and/or supplemented with the PUFAs produced in accordance with the present invention.

J. Oxepa™ Nutritional Product

Oxepa is a low-carbohydrate, calorically dense, enteral nutritional product designed for the dietary management of patients with or at risk for ARDS. It has a unique combination of ingredients, including a patented oil blend containing eicosapentaenoic acid (EPA from fish oil), γ-linolenic acid (GLA from borage oil), and elevated antioxidant levels.

Caloric Distribution:

Caloric density is high at 1.5 Cal/mL (355 Cal/8 fl oz), to minimize the volume required to meet energy needs.

The distribution of Calories in Oxepa is shown in Table A.

TABLE A

Caloric Distribution of Oxepa

|  | per 8 fl oz. | per liter | % of Cal |
|---|---|---|---|
| Calories | 355 | 1,500 | — |
| Fat (g) | 22.2 | 93.7 | 55.2 |
| Carbohydrate (g) | 25 | 105.5 | 28.1 |
| Protein (g) | 14.8 | 62.5 | 16.7 |
| Water (g) | 186 | 785 | — |

Fat:

Oxepa contains 22.2 g of fat per 8-fl oz serving (93.7 g/L). The fat source is an oil blend of 31.8% canola oil, 25% medium-chain triglycerides (MCTs), 20% borage oil, 20% fish oil, and 3.2% soy lecithin. The typical fatty acid profile of Oxepa is shown in Table B.

Oxepa provides a balanced amount of polyunsaturated, monounsaturated, and saturated fatty acids, as shown in Table VI.

Medium-chain triglcerides (MCTs)—25% of the fat blend—aid gastric emptying because they are absorbed by the intestinal tract without emulsification by bile acids.

The various fatty acid components of Oxepa™ nutritional product can be substituted and/or supplemented with the PUFAs produced in accordance with this invention.

TABLE B

Typical Fatty Acid Profile

| Fatty Acids | % Total | g/8 fl oz* | 9/L* |
|---|---|---|---|
| Caproic (6:0) | 0.2 | 0.04 | 0.18 |
| Caprylic (8:0) | 14.69 | 3.1 | 13.07 |
| Capric (10:0) | 11.06 | 2.33 | 9.87 |
| Palmitic (16:0) | 5.59 | 1.18 | 4.98 |
| Palmitoleic | 1.82 | 0.38 | 1.62 |
| Stearic | 1.94 | 0.39 | 1.64 |
| Oleic | 24.44 | 5.16 | 21.75 |
| Linoleic | 16.28 | 3.44 | 14.49 |
| α-Linolenic | 3.47 | 0.73 | 3.09 |
| γ-Linolenic | 4.82 | 1.02 | 4.29 |
| Eicosapentaenoic | 5.11 | 1.08 | 4.55 |
| n-3-Docosapent-aenoic | 0.55 | 0.12 | 0.49 |
| Docosahexaenoic | 2.27 | 0.48 | 2.02 |
| Others | 7.55 | 1.52 | 6.72 |

Fatty acids equal approximately 95% of total fat.

TABLE C

Fat Profile of Oxepa.

| % of total calories from fat | 55.2 |
|---|---|
| Polyunsaturated fatty acids | 31.44 g/L |
| Monounsaturated fatty acids | 25.53 g/L |
| Saturated fatty acids | 32.38 g/L |
| n − 6 to n − 3 ratio | 1.75:1 |
| Cholesterol | 9.49 mg/8 fl oz |
|  | 40.1 mg/L |

Carbohydrate:

The carbohydrate content is 25.0 g per 8-fl-oz serving (105.5 g/L).

The carbohydrate sources are 45% maltodextrin (a complex carbohydrate) and 55% sucrose (a simple sugar), both of which are readily digested and absorbed.

The high-fat and low-carbohydrate content of Oxepa is designed to minimize carbon dioxide ($CO_2$) production. High $CO_2$ levels can complicate weaning in ventilator-dependent patients. The low level of carbohydrate also may be useful for those patients who have developed stress-induced hyperglycemia.

Oxepa is lactose-free.

Dietary carbohydrate, the amino acids from protein, and the glycerol moiety of fats can be converted to glucose within the body. Throughout this process, the carbohydrate requirements of glucose-dependent tissues (such as the central nervous system and red blood cells) are met. However, a diet free of carbohydrates can lead to ketosis, excessive catabolism of tissue protein, and loss of fluid and electrolytes. These effects can be prevented by daily ingestion of 50 to 100 g of digestible carbohydrate, if caloric intake is adequate. The carbohydrate level in Oxepa is also sufficient to minimize gluconeogenesis, if energy needs are being met.

Protein:

Oxepa contains 14.8 g of protein per 8-fl-oz serving (62.5 g/L).

The total calorie/nitrogen ratio (150:1) meets the need of stressed patients.

Oxepa provides enough protein to promote anabolism and the maintenance of lean body mass without precipitating respiratory problems. High protein intakes are a concern in patients with respiratory insufficiency. Although protein has little effect on $CO_2$ production, a high protein diet will increase ventilatory drive.

The protein sources of Oxepa are 86.8% sodium caseinate and 13.2% calcium caseinate.

The amino acid profile of the protein system in Oxepa meets or surpasses the standard for high quality protein set by the National Academy of Sciences.

TABLE 1

*Saprolegnia diclina* (ATCC 56851) Desaturase Expression in Baker's Yeast

| CLONE | TYPE OF ENZYME ACTIVITY | % CONVERSION OF SUBSTRATE |
|---|---|---|
| pRSP1 | Δ9 | 0 (18:0 to 18:1n − 9)* |
| (*S. diclina* Δ6 desaturase) | Δ12 | 0 (18:1 to 18:2n − 6) |
|  | Δ15 | 0 (18:2n − 6 to 18:3n − 3) |
|  | Δ6 | 28 (18:2n − 6 to 18:3n − 6) |
|  | Δ6 | 37 (18:3n − 3 to 18:4n − 3) |
|  | Δ5 | 0 (20:3n − 6 to 20:4n − 6) |
| pRSP3 | Δ9 | 0 (18:0 to 18:1n − 9) |
| (*S. diclina* Δ5 desaturase) | Δ12 | 0 (18:1 to 18:2n − 6) |
|  | Δ15 | 0 (18:2n − 6 to 18:3n − 3) |
|  | Δ6 | 0 (18:2n − 6 to 18:3n − 6) |
|  | Δ6 | 0 (18:3n − 3 to 18:4n − 3) |
|  | Δ5 | 27 (20:3n − 6 to 20:4n − 6) |

*above endogenous Δ9 activity

TABLE 2

Fatty Acid as a Percentage of Total Lipid Extracted from Yeast

| Clone | 18:1* Present | 18:2 (n − 3) Produced | 18:2 (n − 6) Incorporated | 18:3 (n − 3) Produced | 18:3 (n − 6) Produced | 18:3 (n − 3) Incorporated | 18:4 (n − 3) Produced | 20:3 (n − 6) Incorporated | 20:4 (n − 6) Produced |
|---|---|---|---|---|---|---|---|---|---|
| pYX242 (control) | 15.07 | 0 | 11.14 | 0 | 0 | 11.35 | 0 | 11.55 | 0 |
| pRSP1 (Δ6) | 14.41 | 0 | 6.31 | 0 | 2.44 | 7.95 | 4.63 | 13.70 | 0 |
| pRSP3 (Δ5) | 15.34 | 0.08 | 10.72 | 0 | 0 | 10.43 | 0 | 20.69 | 7.74 |

50 μM substrate added
*18:1 is an endogenous fatty acid in yeast
Key:
18:1 = Oleic acid
18:2 (n − 6) = Linoleic acid
18:3 (n − 3) = α-Linolenic acid
18:3 (n − 6) = γ-Linolenic acid
18:4 (n − 3) = Stearidonic acid
20:3 (n − 6) = Dihomo-γ-linolenic acid
20:4 (n − 6) = Arachidonic acid

TABLE 3

Fatty Acid as a Percentage of Total Lipid Extracted from Yeast

| Clone | Plasmid in yeast (enzyme) | 18:2 (n − 6) Incorporated | 18:3 (n − 6) Produced | 20:3 (n − 6) Produced | % Conversion | 18:3 (n − 3) Incorporated | 18:4 (n − 3) Produced | 20:4 (n − 3) Produced | % Conversion |
|---|---|---|---|---|---|---|---|---|---|
| Control | pYX242 + pYES2 | 6.46 | 0 | 0 | 0 | 13.26 | 0 | 0 | 0 |
| pRSP5 | pRSP1 (Δ6) + pRAE73-A3 (human elongase) | 4.62 | 1.95 | 0.8 | 37.3 | 7.00 | 2.47 | 1.20 | 34.39 |
| pRSP8 | pRSP1 (Δ6) + pRPB2 (M. alpina elongase) | 4.08 | 2.31 | 0.63 | 41 | 5.93 | 2.01 | 0.85 | 32.53 |

50 μM substrate added
Key:
18:2 (n − 6) = Linoleic acid
18:3 (n − 3) = α-Linolenic acid
18:3 (n − 6) = γ-Linolenic acid
18:4 (n − 3) = Stearidonic acid
20:3 (n − 6) = Dihomo-γ-linolenic acid
20:4 (n − 3) = Eicosatetraenoic acid
% Conversion = [% Product 1 + % Product 2]/[% substarte + Product 1 + % Product 2]

TABLE 4

Fatty Acid as a Percentage of Total Lipid Extracted from Yeast

| Clone | Plasmid in yeast (enzyme) | 18:3 (n − 6) Incorporated | 20:3 (n − 6) Produced | 20:4 (n − 6) Produced | % Conversion | 18:4 (n − 3) Incorporated | 20:4 (n − 3) Produced | 20:5 (n − 3) Produced | % Conversion |
|---|---|---|---|---|---|---|---|---|---|
| Control | pYX242 + pYES2 | 8.17 | 0 | 0 | 0 | 5.61 | 0 | 0 | 0 |
| pRSP7 | pRSP3 (Δ5) + pRAE73-A3 (human elongase) | 6.25 | 2.30 | 1.63 | 38.6 | 4.12 | 1.98 | 1.56 | 46.2 |
| pRSP10 | pRSP3 (Δ5) + pRPB2 (M. alpina elongase) | 7.00 | 2.07 | 1.35 | 32.82 | 4.66 | 1.50 | 1.61 | 40.02 |

50 μM substrate added
Key:
18:3 (n − 6) = γ-Linolenic acid
18:4 (n − 3) = Stearidonic Acid
20:3 (n − 6) = Dihomo-γ-linolenic acid TABLE 4-continued Fatty Acid as a Percentage of Total Lipid Extracted from Yeast

| Clone | Plasmid in yeast (enzyme) | 18:3 (n − 6) Incorporated | 20:3 (n − 6) Produced | 20:4 (n − 6) Produced | % Conversion | 18:4 (n − 3) Incorporated | 20:4 (n − 3) Produced | 20:5 (n − 3) Produced | % Conversion |
|---|---|---|---|---|---|---|---|---|---|

20:4 (n − 6) = Arachidonic Acid
20:4 (n − 3) = Eicosatetraenoic acid
20:5 (n − 3) = Eicosapentanoic Acid
% Conversion = [% Product 1 + % Product 2]/[% substarte + Product 1 + % Product 2]

TABLE 5

*Thraustochytrium aureum* (ATCC 34304) Desaturase Expression in Baker's Yeast

| CLONE | TYPE OF ENZYME ACTIVITY | % CONVERSION OF SUBSTRATE |
|---|---|---|
| PRTA4 (*T. aureum* Δ5 desaturase) | Δ9 | 0 (18:0 to 18:1n − 9)* |
| | Δ12 | 0 (18:1 to 18:2n − 6) |
| | Δ15 | 0 (18:2n − 6 to 18:3n − 3) |
| | Δ6 | 0 (18:2n − 6 to 18:3n − 6) |
| | Δ6 | 0 (18:3n − 3 to 18:4n − 3) |
| | Δ5 | 23.7 (20:3n − 6 to 20:4n − 6) |
| | Δ17 | 0 (20:4n − 6 to 20:5n − 3) |
| | Δ19 | 0 (22:4n − 6 to 22:5n − 3) |
| | Δ4 | 0 (22:4n − 6 to 22:5n − 6) |
| | Δ4 | 0 (22:5n − 3 to 22:6n − 3) |

*above endogenous Δ9 activity

TABLE 6

Fatty Acid as a Percentage of Total Lipid Extracted from Yeast

| Clone | 18:1* Present | 18:2 Produced | 18:2(n − 6) Incorporated | 18:3(n − 6) Produced | 18:3(n − 6) Produced | 18:3(n − 3) Incorporated | 18:4(n − 3) Produced | 20:3(n − 6) Incorporated | 20:4(n − 6) Produced |
|---|---|---|---|---|---|---|---|---|---|
| PYX242 (control) | 32.13 | 0 | 8.68 | 0 | 0 | 54.42 | 0 | 4.3 | 0 |
| PRTA4 (Δ5) | 29.67 | 0 | 11.18 | 0 | 0 | 9.93 | 0 | 21.94 | 6.84 |

50 μM substrate added
*18:1 is an endogenous fatty acid in yeast
Key:
18:1 = Oleic acid
18:2(n − 6) = Linoleic acid
18:3(n − 3) = α-Linolenic acid
18:3(n − 6) = γ-Linolenic acid
18:4(n − 3) = Stearidonic acid
20:3(n − 6) = Dihomo-γ-linolenic acid
20:4(n − 6) = Arachidonic acid

TABLE 7

Fatty Acid as a Percentage of Total Lipid Extracted from Yeast

| Clone | 20:3 Incorporated | 20:4 Produced | 22:4 Produced | Conversion to products |
|---|---|---|---|---|
| PYX242/ PYES2 (control) | 41.98 | 0 | 0 | 0 |
| PRTA4(Δ5)/ PRAE73-A3 (human elongase) | 15.59 | 4.2 | 6.28 | 16.7 |

100 μM substrate added
*18:1 is an endogenous fatty acid in yeast
Key:
γ-18:3 = γ-Linolenic acid
20:3 = Dihomo-γ-linolenic acid
20:4 = Arachidonic acid
22:4 = Adrenic acid

TABLE 8

Fatty acid profiles of yeast containing pRAT-2c, pYX242, pRAT-2c/pRAE-73-A3, or pYX242/pYES2, grown in the presence of various fatty acids.

| plasmid | pRAT-2c | pYX242 | pRAT-2c pRAE-73 | pYX242 pYES2 | pRAT-2c pRAE-73 | pYX242 pYES2 | pRAT-2c pRAE-73 | pYX242 pYES2 |
|---|---|---|---|---|---|---|---|---|
| 100 μM | DGLA | DGLA | LA | LA | ALA | ALA | GLA | GLA |
| | | | g/100 g Fatty Acid | | | | | |
| C18:2n − 6 | | | 13.98 | 18.49 | | | | |
| C18:3n − 6 | | | | | | | 15.97 | 15.1 |
| C18:3n − 3 | | | | | 10.27 | 14.14 | | |
| C18:4n − 3 | | | | | | | | |
| C20:2n − 6 | | | 0.59 | 0.27 | | | | |
| C20:3n − 6 | 33.37 | 32.4 | | | | | 1.25 | |
| C20:4n − 6 | 22.98 | | | | | | 0.83 | |
| C20:3n − 3 | | | | | 1.58 | 0.25 | | |
| C20:4n − 3 | | | | | | | | |
| | | | % conversion = [product/(substrate + product)] × 100 | | | | | |
| elongase | | | 4.0% | 1.4% | 13.3% | 1.7% | 11.5% | |
| Δ5 | 40.8% | | | | | | 39.9% | |

TABLE 9

Fatty acid profiles of yeast containing pRAT-1a, pYX242, pRAT-1a/pRAE-73-A3, or pYX242/pYES2, grown in the presence of various fatty acids.

| Plasmid | pRAT-1a | pYX242 | pRAT-1a | pYX242 | pRAT-1a | pYX242 | pRAT-1a | pYX242 | pRAT-1a pRAE-73 | pYX242 pYES2 | pRAT-1a pRAE-73 | pYX242 pYES2 |
|---|---|---|---|---|---|---|---|---|---|---|---|---|
| 100 μM | LA | LA | ALA | ALA | EDA | EDA | DGLA | DGLA | LA | LA | ALA | ALA |
| | | | | | g/100 g Fatty Acid | | | | | | | |
| C18:2n − 6 | 18.44 | 20.91 | | | | | | | 11.35 | 18.49 | | |
| C18:3n − 6 | 2.62 | | | | | | | | 3.49 | | | |
| C18:3n − 3 | | | 11.59 | 12.38 | | | | | | | 4.61 | 14.14 |
| C18:4n − 3 | | | 3.37 | | | | | | | | 3.69 | |
| C20:2n − 6 | | | | | 55.6 | 55.55 | | | 0.21 | 0.27 | | |
| C20:3n − 6 | | | | | 2.35 | | 66.37 | 32.4 | 1.1 | | | |
| C20:4n − 6 | | | | | | | 0.78 | | | | | |
| C20:3n − 3 | | | | | | | | | | | 0.65 | 0.25 |
| C20:4n − 3 | | | | | | | | | | | 4.32 | |

TABLE 9-continued

Fatty acid profiles of yeast containing pRAT-1a, pYX242, pRAT-1a/pRAE-73-A3, or pYX242/pYES2, grown in the presence of various fatty acids.

| Plasmid 100 μM | pRAT-1a LA | pYX242 LA | pRAT-1a ALA | pYX242 ALA | pRAT-1a EDA | pYX242 EDA | pRAT-1a DGLA | pYX242 DGLA | pRAT-1a pRAE-73 LA | pYX242 pYES2 LA | pRAT-1a pRAE-73 ALA | pYX242 pYES2 ALA |
|---|---|---|---|---|---|---|---|---|---|---|---|---|
| | | | % conversion = [product/(substrate + product)] × 100 | | | | | | | | | |
| Δ6 | 12.4% | | 22.5% | | | | | | | | | |
| Δ5 | | | | | | | | | | 1.2% | | |
| Δ8 | | | | | 4.0% | | | | | | | |

What is claimed is:

1. An isolated nucleic acid sequence encoding a polypeptide having at least 70% sequence identity to SEQ ID NO:14, wherein said nucleic acid sequence encodes a functionally active Δ6-desaturase.

2. The isolated nucleic acid sequence of claim 1 wherein said Δ6-desaturase utilizes a polyunsaturated fatty acid as a substrate.

3. The isolated nucleic acid sequence of claim 1 wherein said sequence is isolated from *Saprolegnia diclina*.

4. A method of producing a desaturase in a host cell in vitro comprising the steps of:
   a) isolating a nucleotide sequence comprising SEQ ID NO:13;
   b) constructing a vector comprising: i) said isolated nucleotide sequence operably linked to ii) a regulatory sequence;
   c) introducing said vector into a host cell in vitro for a time and under conditions sufficient for expression of said desaturase.

5. A vector comprising:
   a) a nucleotide sequence comprising SEQ ID NO:13, operably linked to b) a regulatory sequence.

6. An isolated host cell comprising said vector of claim 5.

7. An isolated mammalian cell comprising said vector of claim 5, wherein expression of said nucleotide sequence of said vector results in production of altered levels of arachidonic acid (AA), eicosapentaenoic acid (EPA), gamma-linolenic acid (GLA) or stearidonic acid (STA), when said cell is grown in a culture media comprising at least one fatty acid selected from the group consisting of linoleic acid (LA), alpha-linolenic acid (ALA), dihomo-gamma-linolenic acid (DGLA) and eicosapentaenoic acid (EPA).

8. An isolated plant cell or plant tissue comprising said vector of claim 5, wherein expression of said nucleotide sequence of said vector results in production of a polyunsaturated fatty acid by said plant cell, plant or plant tissue.

9. The isolated plant cell or plant tissue of claim 5 wherein said polyunsaturated fatty acid is selected from the group consisting of AA, EPA, GLA and STA.

10. A method for producing a polyunsaturated fatty acid comprising the steps of:

a) isolating a nucleotide sequence comprising SEQ ID NO:13;
b) constructing a vector comprising said isolated nucleotide sequence;
c) introducing said vector into a host cell in vitro for a time and under conditions sufficient for expression of Δ6-desaturase enzyme; and
d) exposing said expressed Δ6-desaturase enzyme to a substrate polyunsaturated fatty acid in order to convert said substrate to a product polyunsaturated fatty acid.

11. The method according to claim 10, wherein said substrate polyunsaturated fatty acid is LA or ALA and said product polyunsaturated fatty acid is GLA or STA, respectively.

12. The method according to claim 10 further comprising the step of exposing said product polyunsaturated fatty acid to an elongase in order to convert said product polyunsaturated fatty acid to another polyunsaturated fatty acid.

13. The method according to claim 12 wherein said product polyunsaturated fatty acid is GLA or STA and said another polyunsaturated fatty acid is DGLA or ETA, respectively.

14. The method of claim 12 further comprising the step of exposing said another polyunsaturated fatty acid to an additional desaturase in order to convert said another polyunsaturated fatty acid to a final polyunsaturated fatty acid.

15. The method of claim 14 wherein said final polyunsaturated fatty acid is AA or EPA.

16. An isolated nucleic acid sequence encoding a polypeptide wherein said polypeptide: 1) has at least 70% sequence identity to SEQ ID NO:14; 2) has a third histidine box motif consisting essentially of QXXHH; and 3) encodes a functionally active Δ6-desaturase.

* * * * *

SEQUENCE LISTING

<160> NUMBER OF SEQ ID NOS: 55

<210> SEQ ID NO 1
<211> LENGTH: 42
<212> TYPE: DNA
<213> ORGANISM: Artificial Sequence
<220> FEATURE:
<223> OTHER INFORMATION: Primer RO834
<220> FEATURE:
<221> NAME/KEY: misc_feature
<222> LOCATION: (3)...(3)
<223> OTHER INFORMATION: b = g or c or t/u at position 3
<220> FEATURE:
<221> NAME/KEY: misc_feature
<222> LOCATION: (6)...(6)
<223> OTHER INFORMATION: y = t/u or c at position 6
<220> FEATURE:
<221> NAME/KEY: misc_feature
<222> LOCATION: (9)...(9)
<223> OTHER INFORMATION: y = t/u or c at position 9
<220> FEATURE:
<221> NAME/KEY: misc_feature
<222> LOCATION: (12)...(12)
<223> OTHER INFORMATION: b = g or c or t/u at position 12
<220> FEATURE:
<221> NAME/KEY: misc_difference
<222> LOCATION: (18)...(18)
<223> OTHER INFORMATION: r = g or a at position 18
<220> FEATURE:
<221> NAME/KEY: misc_feature
<222> LOCATION: (24)...(24)
<223> OTHER INFORMATION: b = g or c or t/u at position 24
<220> FEATURE:
<221> NAME/KEY: misc_feature
<222> LOCATION: (30)...(30)
<223> OTHER INFORMATION: y = t/u or c at position 30
<220> FEATURE:
<221> NAME/KEY: misc_feature
<222> LOCATION: (33)...(33)
<223> OTHER INFORMATION: y = t/u or c at position 33
<220> FEATURE:
<221> NAME/KEY: misc_feature
<222> LOCATION: (36)...(36)
<223> OTHER INFORMATION: b = g or c or t/u at position 36
<220> FEATURE:
<221> NAME/KEY: misc_feature
<222> LOCATION: (39)...(39)
<223> OTHER INFORMATION: h = a or c or t/u at position 39
<220> FEATURE:
<221> NAME/KEY: misc_feature
<222> LOCATION: (42)...(42)
<223> OTHER INFORMATION: h = a or c or t/u at position 42

<400> SEQUENCE: 1
gtbtaygayg tbaccgartg ggtbaagcgy cayccbgghg gh          42

<210> SEQ ID NO 2
<211> LENGTH: 45
<212> TYPE: DNA
<213> ORGANISM: Artificial Sequence
<220> FEATURE:
<223> OTHER INFORMATION: Forward Primer RO835
<220> FEATURE:
<221> NAME/KEY: misc_feature
<222> LOCATION: (3)...(3)
<223> OTHER INFORMATION: h = a or c or t/u at position 3
<220> FEATURE:
<221> NAME/KEY: misc_feature
<222> LOCATION: (6)...(6)
<223> OTHER INFORMATION: y = t/u or c at position 6
<220> FEATURE:
<221> NAME/KEY: misc_feature
<222> LOCATION: (12)...(12)
<223> OTHER INFORMATION: y = t/u or c at position 12
<220> FEATURE:
<221> NAME/KEY: misc_feature
<222> LOCATION: (27)...(27)
<223> OTHER INFORMATION: y = t/u or c at position 27
<220> FEATURE:
<221> NAME/KEY: misc_feature
<222> LOCATION: (33)...(33)
<223> OTHER INFORMATION: y = tu or c at position 33
<220> FEATURE:
<221> NAME/KEY: misc_feature
<222> LOCATION: (39)...(39)
<223> OTHER INFORMATION: b = g or c or t/u at position 39
<220> FEATURE:
<221> NAME/KEY: misc_feature
<222> LOCATION: (42)...(42)
<223> OTHER INFORMATION: y = t/u or c at position 42
<220> FEATURE:
<221> NAME/KEY: misc_feature
<222> LOCATION: (45)...(45)
<223> OTHER INFORMATION: y = t/u or c at position 45

<400> SEQUENCE: 2
gghgcytccg cyaactggtg gaagcaycag cayaacgtbc aycay                45

<210> SEQ ID NO 3
<211> LENGTH: 45
<212> TYPE: DNA
<213> ORGANISM: Artificial Sequence
<220> FEATURE:
<223> OTHER INFORMATION: Reverse Primer RO836
<220> FEATURE:
<221> NAME/KEY: misc_feature
<222> LOCATION: (1)...(1)
<223> OTHER INFORMATION: r = g or a at position 1
<220> FEATURE:
<221> NAME/KEY: misc_feature
<222> LOCATION: (4)...(4)
<223> OTHER INFORMATION: r = g or a at position 4
<220> FEATURE:
<221> NAME/KEY: misc_feature
<222> LOCATION: (7)...(7)
<223> OTHER INFORMATION: v = a or g or c at position 7
<220> FEATURE:
<221> NAME/KEY: misc_feature
<222> LOCATION: (13)...(13)
<223> OTHER INFORMATION: r = g or a at position 13
<220> FEATURE:
<221> NAME/KEY: misc_feature
<222> LOCATION: (19)...(19)
<223> OTHER INFORMATION: r = g or a at position 19
<220> FEATURE:
<221> NAME/KEY: misc_feature
<222> LOCATION: (34)...(34)
<223> OTHER INFORMATION: r = g or a at position 34
<220> FEATURE:
<221> NAME/KEY: misc_feature
<222> LOCATION: (40)...(40)

```
<223> OTHER INFORMATION: r = g or a at position 40
<220> FEATURE:
<221> NAME/KEY: misc_feature
<222> LOCATION: (43)...(43)
<223> OTHER INFORMATION: d = a or g or t/u at position 43

<400> SEQUENCE: 3
rtgrtgvacg ttrtgctgrt gcttccacca gttrgcggar gcdcc                45

<210> SEQ ID NO 4
<211> LENGTH: 36
<212> TYPE: DNA
<213> ORGANISM: Artificial Sequence
<220> FEATURE:
<223> OTHER INFORMATION: Reverse Primer RO838
<220> FEATURE:
<221> NAME/KEY: misc_feature
<222> LOCATION: (6)...(6)
<223> OTHER INFORMATION: r = g or a at position 6
<220> FEATURE:
<221> NAME/KEY: misc_feature
<222> LOCATION: (12)...(12)
<223> OTHER INFORMATION: r = g or a at position 12
<220> FEATURE:
<221> NAME/KEY: misc_feature
<222> LOCATION: (15)...(15)
<223> OTHER INFORMATION: y = t/u or c at position 15
<220> FEATURE:
<221> NAME/KEY: misc_feature
<222> LOCATION: (18)...(18)
<223> OTHER INFORMATION: r = g or a at position 18
<220> FEATURE:
<221> NAME/KEY: misc_feature
<222> LOCATION: (21)...(21)
<223> OTHER INFORMATION: r = g or a at position 21
<220> FEATURE:
<221> NAME/KEY: misc_feature
<222> LOCATION: (24)...(24)
<223> OTHER INFORMATION: s = g or c at position 24
<220> FEATURE:
<221> NAME/KEY: misc_feature
<222> LOCATION: (27)...(27)
<223> OTHER INFORMATION: r = g or a at position 27
<220> FEATURE:
<221> NAME/KEY: misc_feature
<222> LOCATION: (30)...(30)
<223> OTHER INFORMATION: v = a or g or c at position 30

<400> SEQUENCE: 4
ttgatrgtct arctygtrgt rgasaarggv tggtac                          36

<210> SEQ ID NO 5
<211> LENGTH: 24
<212> TYPE: DNA
<213> ORGANISM: Artificial Sequence
<220> FEATURE:
<223> OTHER INFORMATION: Primer RO753
<220> FEATURE:
<221> NAME/KEY: misc_feature
<222> LOCATION: (10)...(10)
<223> OTHER INFORMATION: n = a or g or c or t/u, unknown, or other at
      position 10
<220> FEATURE:
<221> NAME/KEY: misc_feature
<222> LOCATION: (13)...(13)
<223> OTHER INFORMATION: r = g or a at position 13
<220> FEATURE:
<221> NAME/KEY: misc_feature
<222> LOCATION: (16)...(16)
<223> OTHER INFORMATION: n = a or g or c or t/u, unknown, or other at
      position 16
<220> FEATURE:
<221> NAME/KEY: misc_feature
<222> LOCATION: (18)...(19)
<223> OTHER INFORMATION: r = g or a at positions 18-19
```

```
<220> FEATURE:
<221> NAME/KEY: misc_feature
<222> LOCATION: (22)...(22)
<223> OTHER INFORMATION: r = g or a at position 22

<400> SEQUENCE: 5
catcatcatn ggraanarrt grtg                                          24

<210> SEQ ID NO 6
<211> LENGTH: 30
<212> TYPE: DNA
<213> ORGANISM: Artificial Sequence
<220> FEATURE:
<223> OTHER INFORMATION: Primer RO754
<220> FEATURE:
<221> NAME/KEY: misc_feature
<222> LOCATION: (15)...(15)
<223> OTHER INFORMATION: y = t/u or c at position 15
<220> FEATURE:
<221> NAME/KEY: misc_feature
<222> LOCATION: (18)...(18)
<223> OTHER INFORMATION: y = t/u or c at position 18
<220> FEATURE:
<221> NAME/KEY: misc_feature
<222> LOCATION: (21)...(21)
<223> OTHER INFORMATION: n = a or g or c or t/u, unknown, or other at
      position 21
<220> FEATURE:
<221> NAME/KEY: misc_feature
<222> LOCATION: (24)...(24)
<223> OTHER INFORMATION: y = t/u or c at position 24
<220> FEATURE:
<221> NAME/KEY: misc_feature
<222> LOCATION: (27)...(27)
<223> OTHER INFORMATION: n = a or g or c or t/u, unknown, or other at
      position 27
<220> FEATURE:
<221> NAME/KEY: misc_feature
<222> LOCATION: (30)...(30)
<223> OTHER INFORMATION: y = t/u or c at position 30

<400> SEQUENCE: 6
ctactactac tacaycayac ntayacnaay                                    30

<210> SEQ ID NO 7
<211> LENGTH: 29
<212> TYPE: DNA
<213> ORGANISM: Artificial Sequence
<220> FEATURE:
<223> OTHER INFORMATION: Primer RO923

<400> SEQUENCE: 7
cggtgcagtg gtggaagaac aagcacaac                                     29

<210> SEQ ID NO 8
<211> LENGTH: 30
<212> TYPE: DNA
<213> ORGANISM: Artificial Sequence
<220> FEATURE:
<223> OTHER INFORMATION: Primer RO899

<400> SEQUENCE: 8
agcggataac aatttcacac aggaaacagc                                    30

<210> SEQ ID NO 9
<211> LENGTH: 30
<212> TYPE: DNA
<213> ORGANISM: Artificial Sequence
<220> FEATURE:
<223> OTHER INFORMATION: Primer RO939
```

```
<400> SEQUENCE: 9
cgtagtactg ctcgaggagc ttgagcgccg                                    30

<210> SEQ ID NO 10
<211> LENGTH: 31
<212> TYPE: DNA
<213> ORGANISM: Artificial Sequence
<220> FEATURE:
<223> OTHER INFORMATION: Primer RO898

<400> SEQUENCE: 10
cccagtcacg acgttgtaaa acgacggcca g                                  31

<210> SEQ ID NO 11
<211> LENGTH: 45
<212> TYPE: DNA
<213> ORGANISM: Artificial Sequence
<220> FEATURE:
<223> OTHER INFORMATION: Primer RO951

<400> SEQUENCE: 11
tcaacagaat tcatggtcca ggggcaaaag gccgagaaga tctcg                   45

<210> SEQ ID NO 12
<211> LENGTH: 47
<212> TYPE: DNA
<213> ORGANISM: Artificial Sequence
<220> FEATURE:
<223> OTHER INFORMATION: Primer RO960

<400> SEQUENCE: 12
atacgtaagc ttttacatgg cgggaaactc cttgaagaac tcgatcg                 47

<210> SEQ ID NO 13
<211> LENGTH: 1362
<212> TYPE: DNA
<213> ORGANISM: Saprolegnia diclina

<400> SEQUENCE: 13
atggtccagg ggcaaaaggc cgagaagatc tcgtgggcga ccatccgtga gcacaaccgc    60
caagacaacg cgtggatcgt gatccaccac aaggtgtacg acatctcggc ctttgaggac   120
cacccgggcg gcgtcgtcat gttcacgcag gccggcgaag acgcgaccga tgcgttcgct   180
gtcttccacc cgagctcggc gctcaagctc ctcgagcagt actacgtcgg cgacgtcgac   240
cagtcgacgg cggccgtcga cacgtcgatc tcggacgagg tcaagaagag ccagtcggac   300
ttcattgcgt cgtaccgcaa gctgcgcctt gaagtcaagc gcctcggctt gtacgactcg   360
agcaagctct actacctcta caagtgcgcc tcgacgctga gcattgcgct tgtgtcggcg   420
gccatttgcc tccactttga ctcgacggcc atgtacatgg tcgcggctgt catccttggc   480 ctctttttacc agcagtgcgg ctggctcgcc catgactttc tgcaccacca agtgtttgag   540
aaccacttgt tggcgacct cgtcggcgtc atggtcggca acctctggca gggcttctcg   600
gtgcagtggt ggaagaacaa gcacaacacg caccatgcga tccccaacct ccacgcgacg   660
cccgagatcg ccttccacgg cgacccggac attgacacga tgccgattct cgcgtggtcg   720
ctcaagatgg cgcagcacgc ggtcgactcg ccgtcgggc tcttcttcat gcgctaccaa   780
gcgtacctgt actttcccat cttgctcttt gcgcgtatct cgtgggtgat ccagtcggcc   840
atgtacgcct tctacaacgt tgggcccggc ggcacctttg acaaggtcca gtacccgctg   900
ctcgagcgcg ccggcctcct cctctactac ggctggaacc tcggccttgt gtacgcagcc   960
```

-continued

```
aacatgtcgc tgctccaagc ggctgcgttc ctctttgtga gccaggcgtc gtgcggcctc    1020
ttcctcgcga tggtctttag cgtcggccac aacggcatgg aggtctttga caaggacagc    1080
aagcccgatt tttggaagct gcaagtgctc tcgacgcgca acgtgacgtc gtcgctctgg    1140
atcgactggt tcatgggcgg cctcaactac cagatcgacc accacttgtt cccgatggtg    1200
ccccggcaca acctcccggc gctcaacgtg ctcgtcaagt cgctctgcaa gcagtacgac    1260
atcccatacc acgagacggg cttcatcgcg ggcatggccg aggtcgtcgt gcacctcgag    1320
cgcatctcga tcgagttctt caaggagttt cccgccatgt aa                      1362
```

<210> SEQ ID NO 14
<211> LENGTH: 453
<212> TYPE: PRT
<213> ORGANISM: Saprolegnia diclina

<400> SEQUENCE: 14

```
Met Val Gln Gly Gln Lys Ala Glu Lys Ile Ser Trp Ala Thr Ile Arg
 1               5                  10                  15

Glu His Asn Arg Gln Asp Asn Ala Trp Ile Val Ile His His Lys Val
            20                  25                  30

Tyr Asp Ile Ser Ala Phe Glu Asp His Pro Gly Gly Val Val Met Phe
        35                  40                  45

Thr Gln Ala Gly Glu Asp Ala Thr Asp Ala Phe Ala Val Phe His Pro
    50                  55                  60

Ser Ser Ala Leu Lys Leu Leu Glu Gln Tyr Tyr Val Gly Asp Val Asp
65                  70                  75                  80

Gln Ser Thr Ala Ala Val Asp Thr Ser Ile Ser Asp Glu Val Lys Lys
                85                  90                  95

Ser Gln Ser Asp Phe Ile Ala Ser Tyr Arg Lys Leu Arg Leu Glu Val
            100                 105                 110

Lys Arg Leu Gly Leu Tyr Asp Ser Ser Lys Leu Tyr Tyr Leu Tyr Lys
        115                 120                 125

Cys Ala Ser Thr Leu Ser Ile Ala Leu Val Ser Ala Ala Ile Cys Leu
    130                 135                 140

His Phe Asp Ser Thr Ala Met Tyr Met Val Ala Ala Val Ile Leu Gly
145                 150                 155                 160

Leu Phe Tyr Gln Gln Cys Gly Trp Leu Ala His Asp Phe Leu His His
                165                 170                 175

Gln Val Phe Glu Asn His Leu Phe Gly Asp Leu Val Gly Val Met Val
            180                 185                 190

Gly Asn Leu Trp Gln Gly Phe Ser Val Gln Trp Lys Asn Lys His
        195                 200                 205

Asn Thr His His Ala Ile Pro Asn Leu His Ala Thr Pro Glu Ile Ala
    210                 215                 220

Phe His Gly Asp Pro Asp Ile Asp Thr Met Pro Ile Leu Ala Trp Ser
225                 230                 235                 240

Leu Lys Met Ala Gln His Ala Val Asp Ser Pro Val Gly Leu Phe Phe
                245                 250                 255

Met Arg Tyr Gln Ala Tyr Leu Tyr Phe Pro Ile Leu Leu Phe Ala Arg
            260                 265                 270

Ile Ser Trp Val Ile Gln Ser Ala Met Tyr Ala Phe Tyr Asn Val Gly
        275                 280                 285

Pro Gly Gly Thr Phe Asp Lys Val Gln Tyr Pro Leu Leu Glu Arg Ala
    290                 295                 300
```

```
Gly Leu Leu Leu Tyr Tyr Gly Trp Asn Leu Gly Leu Val Tyr Ala Ala
305                 310                 315                 320

Asn Met Ser Leu Leu Gln Ala Ala Phe Leu Phe Val Ser Gln Ala
            325                 330                 335

Ser Cys Gly Leu Phe Leu Ala Met Val Phe Ser Val Gly His Asn Gly
            340                 345                 350

Met Glu Val Phe Asp Lys Asp Ser Lys Pro Asp Phe Trp Lys Leu Gln
            355                 360                 365

Val Leu Ser Thr Arg Asn Val Thr Ser Ser Leu Trp Ile Asp Trp Phe
370                 375                 380

Met Gly Gly Leu Asn Tyr Gln Ile Asp His His Leu Phe Pro Met Val
385                 390                 395                 400

Pro Arg His Asn Leu Pro Ala Leu Asn Val Leu Val Lys Ser Leu Cys
                405                 410                 415

Lys Gln Tyr Asp Ile Pro Tyr His Glu Thr Gly Phe Ile Ala Gly Met
            420                 425                 430

Ala Glu Val Val Val His Leu Glu Arg Ile Ser Ile Glu Phe Phe Lys
            435                 440                 445

Glu Phe Pro Ala Met
    450
```

```
<210> SEQ ID NO 15
<211> LENGTH: 23
<212> TYPE: DNA
<213> ORGANISM: Artificial Sequence
<220> FEATURE:
<223> OTHER INFORMATION: Primer RO851

<400> SEQUENCE: 15
ccatcaagac gtaccttgcg atc                                              23

<210> SEQ ID NO 16
<211> LENGTH: 28
<212> TYPE: DNA
<213> ORGANISM: Artificial Sequence
<220> FEATURE:
<223> OTHER INFORMATION: Primer RO941

<400> SEQUENCE: 16
gctgaacggg tggtacgagt cgaacgtg                                         28

<210> SEQ ID NO 17
<211> LENGTH: 42
<212> TYPE: DNA
<213> ORGANISM: Artificial Sequence
<220> FEATURE:
<223> OTHER INFORMATION: Primer RO953

<400> SEQUENCE: 17
acgagagaat tcatggcccc gcagacggag ctccgccagc gc                         42

<210> SEQ ID NO 18
<211> LENGTH: 46
<212> TYPE: DNA
<213> ORGANISM: Artificial Sequence
<220> FEATURE:
<223> OTHER INFORMATION: Primer RO956

<400> SEQUENCE: 18
aaaagactcg agttagccca tgtggatcgt ggcggcgatg ccctgc                     46
```

<210> SEQ ID NO 19
<211> LENGTH: 1413
<212> TYPE: DNA
<213> ORGANISM: Saprolegnia diclina

<400> SEQUENCE: 19

| | | | | | |
|---|---|---|---|---|---|
| atggccccgc | agacggagct | ccgccagcgc | acgccgccg | tcgccgagac | gccggtggcc | 60 |
| ggcaagaagg | cctttacatg | gcaggaggtc | gcgcagcaca | cacggcggc | ctcggcctgg | 120 |
| atcattatcc | gcggcaaggt | ctacgacgtg | accgagtggg | ccaacaagca | ccccggcggc | 180 |
| cgcgagatgg | tgctgctgca | cgccggtcgc | gaggccaccg | acacgttcga | ctcgtaccac | 240 |
| ccgttcagcg | acaaggccga | gtcgatcttg | aacaagtatg | agattggcac | gttcacgggc | 300 |
| ccgtccgagt | ttccgacctt | caagccggac | acgggcttct | acaaggagtg | ccgcaagcgc | 360 |
| gttggcgagt | acttcaagaa | gaacaacctc | catccgcagg | acggcttccc | gggcctctgg | 420 |
| cgcatgatgg | tcgtgtttgc | ggtcgccggc | ctcgccttgt | acggcatgca | cttttcgact | 480 |
| atctttgcgc | tgcagctcgc | ggccgcggcg | ctctttggcg | tctgccaggc | gctgccgctg | 540 |
| ctccacgtca | tgcacgactc | gtcgcacgcg | tcgtacacca | acatgccgtt | cttccattac | 600 |
| gtcgtcggcc | gctttgccat | ggactggttt | gccggcggct | cgatggtgtc | atggctcaac | 660 |
| cagcacgtcg | tgggccacca | catctacacg | aacgtcgcgg | gctcggaccc | ggatcttccg | 720 |
| gtcaacatgg | acggcgacat | ccgccgcatc | gtgaaccgcc | aggtgttcca | gcccatgtac | 780 |
| gcattccagc | acatctacct | tccgccgctc | tatggcgtgc | ttggcctcaa | gttccgcatc | 840 |
| caggacttca | ccgacacgtt | cggctcgcac | acgaacggcc | cgatccgcgt | caacccgcac | 900 |
| gcgctctcga | cgtggatggc | catgatcagc | tccaagtcgt | tctgggcctt | ctaccgcgtg | 960 |
| taccttccgc | ttgccgtgct | ccagatgccc | atcaagacgt | accttgcgat | cttcttcctc | 1020 |
| gccgagtttg | tcacgggctg | gtacctcgcg | ttcaacttcc | aagtaagcca | tgtctcgacc | 1080 |
| gagtgcggct | acccatgcgg | cgacgaggcc | aagatggcgc | tccaggacga | gtgggcagtc | 1140 |
| tcgcaggtca | agacgtcggt | cgactacgcc | atggctcgt | ggatgacgac | gttccttgcc | 1200 |
| ggcgcgctca | actaccaggt | cgtgcaccac | ttgttcccca | gcgtgtcgca | gtaccactac | 1260 |
| ccggcgatcg | cgcccatcat | cgtcgacgtc | tgcaaggagt | acaacatcaa | gtacgccatc | 1320 |
| ttgccggact | ttacggcggc | gttcgttgcc | cacttgaagc | cctccgcaa | catgggccag | 1380 |
| cagggcatcg | ccgccacgat | ccacatgggc | taa | | | 1413 |

<210> SEQ ID NO 20
<211> LENGTH: 470
<212> TYPE: PRT
<213> ORGANISM: Saprolegnia diclina

<400> SEQUENCE: 20

Met Ala Pro Gln Thr Glu Leu Arg Gln Arg His Ala Ala Val Ala Glu
1               5                   10                  15

Thr Pro Val Ala Gly Lys Lys Ala Phe Thr Trp Gln Glu Val Ala Gln
            20                  25                  30

His Asn Thr Ala Ala Ser Ala Trp Ile Ile Ile Arg Gly Lys Val Tyr
        35                  40                  45

Asp Val Thr Glu Trp Ala Asn Lys His Pro Gly Gly Arg Glu Met Val
    50                  55                  60

Leu Leu His Ala Gly Arg Glu Ala Thr Asp Thr Phe Asp Ser Tyr His
65                  70                  75                  80

```
-continued

Pro Phe Ser Asp Lys Ala Glu Ser Ile Leu Asn Lys Tyr Glu Ile Gly
            85                  90                  95

Thr Phe Thr Gly Pro Ser Glu Phe Pro Thr Phe Lys Pro Asp Thr Gly
            100                 105                 110

Phe Tyr Lys Glu Cys Arg Lys Arg Val Gly Tyr Phe Lys Lys Asn
        115                 120                 125

Asn Leu His Pro Gln Asp Gly Phe Pro Gly Leu Trp Arg Met Met Val
    130                 135                 140

Val Phe Ala Val Ala Gly Leu Ala Leu Tyr Gly Met His Phe Ser Thr
145                 150                 155                 160

Ile Phe Ala Leu Gln Leu Ala Ala Ala Leu Phe Gly Val Cys Gln
                165                 170                 175

Ala Leu Pro Leu Leu His Val Met His Asp Ser Ser His Ala Ser Tyr
            180                 185                 190

Thr Asn Met Pro Phe Phe His Tyr Val Val Gly Arg Phe Ala Met Asp
            195                 200                 205

Trp Phe Ala Gly Gly Ser Met Val Ser Trp Leu Asn Gln His Val Val
    210                 215                 220

Gly His His Ile Tyr Thr Asn Val Ala Gly Ser Asp Pro Asp Leu Pro
225                 230                 235                 240

Val Asn Met Asp Gly Asp Ile Arg Arg Ile Val Asn Arg Gln Val Phe
                245                 250                 255

Gln Pro Met Tyr Ala Phe Gln His Ile Tyr Leu Pro Pro Leu Tyr Gly
            260                 265                 270

Val Leu Gly Leu Lys Phe Arg Ile Gln Asp Phe Thr Asp Thr Phe Gly
        275                 280                 285

Ser His Thr Asn Gly Pro Ile Arg Val Asn Pro His Ala Leu Ser Thr
    290                 295                 300

Trp Met Ala Met Ile Ser Ser Lys Ser Phe Trp Ala Phe Tyr Arg Val
305                 310                 315                 320

Tyr Leu Pro Leu Ala Val Leu Gln Met Pro Ile Lys Thr Tyr Leu Ala
                325                 330                 335

Ile Phe Phe Leu Ala Glu Phe Val Thr Gly Trp Tyr Leu Ala Phe Asn
            340                 345                 350

Phe Gln Val Ser His Val Ser Thr Glu Cys Gly Tyr Pro Cys Gly Asp
        355                 360                 365

Glu Ala Lys Met Ala Leu Gln Asp Glu Trp Ala Val Ser Gln Val Lys
370                 375                 380

Thr Ser Val Asp Tyr Ala His Gly Ser Trp Met Thr Thr Phe Leu Ala
385                 390                 395                 400

Gly Ala Leu Asn Tyr Gln Val Val His His Leu Phe Pro Ser Val Ser
                405                 410                 415

Gln Tyr His Tyr Pro Ala Ile Ala Pro Ile Ile Val Asp Val Cys Lys
            420                 425                 430

Glu Tyr Asn Ile Lys Tyr Ala Ile Leu Pro Asp Phe Thr Ala Ala Phe
        435                 440                 445

Val Ala His Leu Lys His Leu Arg Asn Met Gly Gln Gln Gly Ile Ala
450                 455                 460

Ala Thr Ile His Met Gly
465             470

<210> SEQ ID NO 21
<211> LENGTH: 914
<212> TYPE: DNA
```

<213> ORGANISM: Homo sapiens

<400> SEQUENCE: 21

| | | | | | |
|---|---|---|---|---|---|
| atggaacatt | ttgatgcatc | acttagtacc | tatttcaagg | cattgctagg | ccctcgagat | 60 |
| actagagtaa | aaggatggtt | tcttctggac | aattatatac | ccacatttat | ctgctctgtc | 120 |
| atatatttac | taattgtatg | ctgggacca | aaatacatga | ggaataaaca | gccattctct | 180 |
| tgccggggga | ttttagtggt | gtataacctt | ggactcacac | tgctgtctct | gtatatgttc | 240 |
| tgtgagttag | taacaggagt | atgggaaggc | aaatacaact | tcttctgtca | gggcacacgc | 300 |
| accgcaggag | aatcagatat | gaagattatc | cgtgtcctct | ggtggtacta | cttctccaaa | 360 |
| ctcatagaat | ttatggacac | tttcttcttc | atcctgcgca | agaacaacca | ccagatcacg | 420 |
| gtcctgcacg | tctaccacca | tgcctcgatg | ctgaacatct | ggtggtttgt | gatgaactgg | 480 |
| gtcccctgcg | gccactctta | ttttggtgcc | acacttaata | gcttcatcca | cgtcctcatg | 540 |
| tactcttact | atggtttgtc | gtcagtccct | tccatgcgtc | catacctctg | gtggaagaag | 600 |
| tacatcactc | aggggcagct | gcttcagttt | gtgctgacaa | tcatccagac | cagctgcggg | 660 |
| gtcatctggc | cgtgcacatt | ccctcttggt | tggttgtatt | tccagattgg | atacattatt | 720 |
| tccctgattg | ctctcttcac | aaacttctac | attcagacct | acaacaagaa | aggggcctcc | 780 |
| cgaaggaaag | accacctgaa | ggaccaccag | aatgggtccg | tggctgctgt | gaatggacac | 840 |
| accaacagct | tttcacccct | ggaaaacaat | gtgaagccaa | ggaagctgcg | gaaggattga | 900 |
| agtcaaagaa | ttga | | | | | 914 |

<210> SEQ ID NO 22
<211> LENGTH: 957
<212> TYPE: DNA
<213> ORGANISM: Mortierella alpina

<400> SEQUENCE: 22

| | | | | | |
|---|---|---|---|---|---|
| atggagtcga | ttgcgccatt | cctcccatca | aagatgccgc | aagatctgtt | tatggacctt | 60 |
| gccaccgcta | tcggtgtccg | ggccgcgccc | tatgtcgatc | ctctcgaggc | cgcgctggtg | 120 |
| gcccaggccg | agaagtacat | ccccacgatt | gtccatcaca | cgcgtgggtt | cctggtcgcg | 180 |
| gtggagtcgc | ctttggcccg | tgagctgccg | ttgatgaacc | cgttccacgt | gctgttgatc | 240 |
| gtgctcgctt | atttggtcac | ggtctttgtg | ggcatgcaga | tcatgaagaa | ctttgagcgg | 300 |
| ttcgaggtca | agacgttttc | gctcctgcac | aacttttgtc | tggtctcgat | cagcgcctac | 360 |
| atgtgcggtg | ggatcctgta | cgaggcttat | caggccaact | atggactgtt | tgagaacgct | 420 |
| gctgatcata | ccttcaaggg | tcttcctatg | gccaagatga | tctggctctt | ctacttctcc | 480 |
| aagatcatgg | agtttgtcga | caccatgatc | atggtcctca | agaagaacaa | ccgccagatc | 540 |
| tccttcttgc | acgtttacca | ccacagctcc | atcttcacca | tctggtggtt | ggtcaccttt | 600 |
| gttgcaccca | acggtgaagc | ctacttctct | gctgcgttga | actcgttcat | ccatgtgatc | 660 |
| atgtacggct | actacttctt | gtcggccttg | gcttcaagc | aggtgtcgtt | catcaagttc | 720 |
| tacatcacgc | gctcgcagat | gacacagttc | tgcatgatgt | cggtccagtc | ttcctgggac | 780 |
| atgtacgcca | tgaaggtcct | tggccgcccc | ggatacccct | tcttcatcac | ggctctgctt | 840 |
| tggttctaca | tgtggaccat | gctcggtctc | ttctacaact | tttacagaaa | gaacgccaag | 900 |
| ttggccaagc | aggccaaggc | cgacgctgcc | aaggagaagg | caaggaagtt | gcagtaa | 957 |

<210> SEQ ID NO 23
<211> LENGTH: 30

<212> TYPE: DNA
<213> ORGANISM: Artificial Sequence
<220> FEATURE:
<223> OTHER INFORMATION: Primer RO936

<400> SEQUENCE: 23
gtcgggcaag gcggaaaagt acctcaagag                                    30

<210> SEQ ID NO 24
<211> LENGTH: 30
<212> TYPE: DNA
<213> ORGANISM: Artificial Sequence
<220> FEATURE:
<223> OTHER INFORMATION: Primer RO937

<400> SEQUENCE: 24
aaacctgtag acaatgtgga ggggcgtggg                                    30

<210> SEQ ID NO 25
<211> LENGTH: 42
<212> TYPE: DNA
<213> ORGANISM: Artificial Sequence
<220> FEATURE:
<223> OTHER INFORMATION: Primer RO972

<400> SEQUENCE: 25
atacttgaat tcatgggacg cggcggcgaa ggtcaggtga ac                      42

<210> SEQ ID NO 26
<211> LENGTH: 39
<212> TYPE: DNA
<213> ORGANISM: Artificial Sequence
<220> FEATURE:
<223> OTHER INFORMATION: Primer RO949

<400> SEQUENCE: 26
cttatactcg agctaagcgg ccttggccgc cgcctggcc                          39

<210> SEQ ID NO 27
<211> LENGTH: 41
<212> TYPE: DNA
<213> ORGANISM: Artificial Sequence
<220> FEATURE:
<223> OTHER INFORMATION: Primer RO950

<400> SEQUENCE: 27
cttatactcg agtaaatggc tcgcgaggcg aagcgagtgg c                       41

<210> SEQ ID NO 28
<211> LENGTH: 1320
<212> TYPE: DNA
<213> ORGANISM: Thraustochytrium aureum

<400> SEQUENCE: 28
atgggacgcg gcggcgaagg tcaggtgaac agcgcgcagg tggcacaagg cggtgcggga      60
acgcgaaaga cgatcctgat cgagggcgag gtctacgatg tcaccaactt taggcacccc    120
ggcgggtcga tcatcaagtt tctcacgacc gacggcaccg aggctgtgga cgcgacgaac    180
gcgtttcgcg agtttcactg ccggtcgggc aaggcggaaa agtacctcaa gagcctgccc    240
aagctcggcg cgccgagcaa gatgaagttt gacgccaagg agcaggcccg gcgcgacgcg    300
atcacgcgag actacgtcaa gctgcgcgag gagatggtgg ccgagggcct cttcaagccc    360
gcgcccctcc acattgtcta caggtttgcg gagatcgcag ccctgttcgc ggcctcgttc    420

-continued

```
tacctgttttt cgatgcgcgg aaacgtgttc gccacgctcg cggccatcgc agtcggggc      480 atcgcgcagg gccgctgcgg ctggctcatg cacgagtgcg acacttctc gatgaccggg      540 tacatcccgc ttgacgtgcg cctgcaggag ctggtgtacg gcgtggggtg ctcgatgtcg      600
gcgagctggt ggcgcgttca gcacaacaag caccacgcga ccccgcagaa actcaagcac      660
gacgtcgacc tcgacaccct gccgtcgtt gcgttcaacg agaagatcgc cgccaaggtg      720
cgccccggct cgttccaggc caagtggctc tcggcgcagg cgtacatttt tgcgccggtg      780
tcctgcttcc tggttggtct cttctggacc ctgtttctgc acccgcgcca catgccgcgc      840
acgagccact ttgctgagat ggccgccgtc gcggtgcgcg tcgtgggctg gcggcgctc       900 atgcactcgt tcgggtacag cgggagcgac tcgttcggtc tctacatggc cacctttggc     960
tttggctgca cctacatctt caccaacttt gcggtcagcc acacgcacct cgacgtcacc    1020
gagccggacg agttcctgca ctgggtcgag tacgccgcgc tgcacgcgac caacgtgtcc    1080
aacgactcgt ggttcatcac ctggtggatg tcgtacctca actttcagat cgagcaccac    1140
ctctttccgt cgctgcccca gctcaacgcc ccgcgcgtcg cccgcgcgt ccgcgccctc     1200 ttcgagaagc acggcatggc ttacgacgag cgcccgtacc ttaccgcgct ggcgacacg     1260 tttgccaacc tgcacgccgt gggccaaaac gcgggccagg cggcggccaa ggccgcttag    1320
```

```
<210> SEQ ID NO 29
<211> LENGTH: 439
<212> TYPE: PRT
<213> ORGANISM: Thraustochytrium aureum

<400> SEQUENCE: 29
```

Met Gly Arg Gly Gly Glu Gly Gln Val Asn Ser Ala Gln Val Ala Gln
 1               5                  10                  15

Gly Gly Ala Gly Thr Arg Lys Thr Ile Leu Ile Glu Gly Glu Val Tyr
                20                  25                  30

Asp Val Thr Asn Phe Arg His Pro Gly Gly Ser Ile Ile Lys Phe Leu
            35                  40                  45

Thr Thr Asp Gly Thr Glu Ala Val Asp Ala Thr Asn Ala Phe Arg Glu
        50                  55                  60

Phe His Cys Arg Ser Gly Lys Ala Glu Lys Tyr Leu Lys Ser Leu Pro
65                  70                  75                  80

Lys Leu Gly Ala Pro Ser Lys Met Lys Phe Asp Ala Lys Glu Gln Ala
                85                  90                  95

Arg Arg Asp Ala Ile Thr Arg Asp Tyr Val Lys Leu Arg Glu Glu Met
            100                 105                 110

Val Ala Glu Gly Leu Phe Lys Pro Ala Pro Leu His Ile Val Tyr Arg
        115                 120                 125

Phe Ala Glu Ile Ala Ala Leu Phe Ala Ala Ser Phe Tyr Leu Phe Ser
    130                 135                 140

Met Arg Gly Asn Val Phe Ala Thr Leu Ala Ala Ile Ala Val Gly Gly
145                 150                 155                 160

Ile Ala Gln Gly Arg Cys Gly Trp Leu Met His Glu Cys Gly His Phe
                165                 170                 175

Ser Met Thr Gly Tyr Ile Pro Leu Asp Val Arg Leu Gln Glu Leu Val
            180                 185                 190

Tyr Gly Val Gly Cys Ser Met Ser Ala Ser Trp Trp Arg Val Gln His
        195                 200                 205

Asn Lys His His Ala Thr Pro Gln Lys Leu Lys His Asp Val Asp Leu
    210                 215                 220

```
Asp Thr Leu Pro Leu Val Ala Phe Asn Glu Lys Ile Ala Ala Lys Val
225                 230                 235                 240

Arg Pro Gly Ser Phe Gln Ala Lys Trp Leu Ser Ala Gln Ala Tyr Ile
            245                 250                 255

Phe Ala Pro Val Ser Cys Phe Leu Val Gly Leu Phe Trp Thr Leu Phe
            260                 265                 270

Leu His Pro Arg His Met Pro Arg Thr Ser His Phe Ala Glu Met Ala
        275                 280                 285

Ala Val Ala Val Arg Val Val Gly Trp Ala Ala Leu Met His Ser Phe
    290                 295                 300

Gly Tyr Ser Gly Ser Asp Ser Phe Gly Leu Tyr Met Ala Thr Phe Gly
305                 310                 315                 320

Phe Gly Cys Thr Tyr Ile Phe Thr Asn Phe Ala Val Ser His His
                325                 330                 335

Leu Asp Val Thr Glu Pro Asp Glu Phe Leu His Trp Val Glu Tyr Ala
            340                 345                 350

Ala Leu His Thr Thr Asn Val Ser Asn Asp Ser Trp Phe Ile Thr Trp
        355                 360                 365

Trp Met Ser Tyr Leu Asn Phe Gln Ile Glu His His Leu Phe Pro Ser
370                 375                 380

Leu Pro Gln Leu Asn Ala Pro Arg Val Ala Pro Arg Val Arg Ala Leu
385                 390                 395                 400

Phe Glu Lys His Gly Met Ala Tyr Asp Glu Arg Pro Tyr Leu Thr Ala
            405                 410                 415

Leu Gly Asp Thr Phe Ala Asn Leu His Ala Val Gly Gln Asn Ala Gly
            420                 425                 430

Gln Ala Ala Lys Ala Ala
        435

<210> SEQ ID NO 30
<211> LENGTH: 1338
<212> TYPE: DNA
<213> ORGANISM: Thraustochytrium aureum

<400> SEQUENCE: 30
gaattcacca tgggtcgcgg agcacaggga gagccaaggc aggccacaga gctgaagagc    60
agcccaagtg agcagcgtaa ggtgttgctc attgacgggc agctgtacga tgcaaccaac   120
ttcaggcatc ctggtggctc catcatcaaa tatttgtgca ccgatggcaa ggaggtagtt   180
gatgcaaccg aagcgtacaa ggagttccac tgcagatcct cgaaggcggt caagtacctc   240
aactccctgc caaagatcga cggcccaatc aagtacaaat acgacgcaaa ggagcaggct   300
cgccatgaca aactcacgag ggagtatgta gctctccgcg aacagctcgt caaggaggga   360
tactttgacc ccagcccgct ccacattatc tacagatgcg ccgagttggc agccatgttc   420
gctctctcgt tctaccttttt ctccttcaag ggtaacgtca tggccactat tgctgccatc   480
gtgattgggg ggtgcgtgca gggtcgttgt ggtggctca tgcatgaagc tggccactac   540
agcatgaccg aaacatccc tgttgacttg cgccttcaag agttttttgta cggaattggg   600 tgtggcatga gcggggcttg gtggagaagc cagcacaaca agcaccacgc cacccccaa    660 aagctcaagc atgacgttga tttggacact cttcctcttg tcgcctggaa cgagaaaatt   720
gcccgtcgcg tcaagccagg tagcttccag gcaaagtggc ttcatctcca gggatacatc   780
tttgccccag tctcctgcct tctcgttggt ctcttctgga ctttgtactt gcatcctcgc   840
```

-continued

```
cacatgatcc gcaccaagcg caacttcgag atattttctg tcgctctgcg ctacgtatgc    900
tggttctcgc ttcttttgag catgggctac actgtcggag agtctctggg tctctatgtg    960 cttactttg  acttggctg  tacctacatc tttacgcatt ttgctgtaag ccacacccac   1020
ttgccagtgt ccgaggagga cgagtacctg cactgggtcg agtacgctgc gctgcacacc   1080
acgaacgttg ccatcgactc gtacgttgtc acctggctga tgagctacct caactttcag   1140
atcgagcacc acttgttccc ttgctgcccg cagttccgcc accctgcaat ctcttctcgc   1200
gtcaagaaac ttttcgagga caatggtctg gtatacgacg cccgctcata cgtccaggcg   1260
ctcaaggata ccttcggcaa cctacacgaa gtgggcgtca acgctggcca agctgccaag   1320
agcgagtaag atctcgag                                                1338
```

<210> SEQ ID NO 31
<211> LENGTH: 439
<212> TYPE: PRT
<213> ORGANISM: Thraustochytrium aureum

<400> SEQUENCE: 31

| Met | Gly | Arg | Gly | Ala | Gln | Gly | Glu | Pro | Arg | Gln | Ala | Thr | Glu | Leu | Lys |
|1|||||5|||||10|||||15|

Ser Ser Pro Ser Glu Gln Arg Lys Val Leu Leu Ile Asp Gly Gln Leu
            20                  25                  30

Tyr Asp Ala Thr Asn Phe Arg His Pro Gly Gly Ser Ile Ile Lys Tyr
        35                  40                  45

Leu Cys Thr Asp Gly Lys Glu Val Val Asp Ala Thr Glu Ala Tyr Lys
    50                  55                  60

Glu Phe His Cys Arg Ser Ser Lys Ala Val Lys Tyr Leu Asn Ser Leu
65                  70                  75                  80

Pro Lys Ile Asp Gly Pro Ile Lys Tyr Lys Tyr Asp Ala Lys Glu Gln
                85                  90                  95

Ala Arg His Asp Lys Leu Thr Arg Glu Tyr Val Ala Leu Arg Glu Gln
            100                 105                 110

Leu Val Lys Glu Gly Tyr Phe Asp Pro Ser Pro Leu His Ile Ile Tyr
        115                 120                 125

Arg Cys Ala Glu Leu Ala Ala Met Phe Ala Leu Ser Phe Tyr Leu Phe
    130                 135                 140

Ser Phe Lys Gly Asn Val Met Ala Thr Ile Ala Ala Ile Val Ile Gly
145                 150                 155                 160

Gly Cys Val Gln Gly Arg Cys Gly Trp Leu Met His Glu Ala Gly His
                165                 170                 175

Tyr Ser Met Thr Gly Asn Ile Pro Val Asp Leu Arg Leu Gln Glu Phe
            180                 185                 190

Leu Tyr Gly Ile Gly Cys Gly Met Ser Gly Ala Trp Trp Arg Ser Gln
        195                 200                 205

His Asn Lys His His Ala Thr Pro Gln Lys Leu Lys His Asp Val Asp
    210                 215                 220

Leu Asp Thr Leu Pro Leu Val Ala Trp Asn Glu Lys Ile Ala Arg Arg
225                 230                 235                 240

Val Lys Pro Gly Ser Phe Gln Ala Lys Trp Leu His Leu Gln Gly Tyr
                245                 250                 255

Ile Phe Ala Pro Val Ser Cys Leu Leu Val Gly Leu Phe Trp Thr Leu
            260                 265                 270

Tyr Leu His Pro Arg His Met Ile Arg Thr Lys Arg Asn Phe Glu Ile
        275                 280                 285

```
Phe Ser Val Ala Leu Arg Tyr Val Cys Trp Phe Ser Leu Leu Leu Ser
    290                 295                 300
Met Gly Tyr Thr Val Gly Glu Ser Leu Gly Leu Tyr Val Leu Thr Phe
305                 310                 315                 320
Gly Leu Gly Cys Thr Tyr Ile Phe Thr His Phe Ala Val Ser His Thr
                325                 330                 335
His Leu Pro Val Ser Glu Glu Asp Glu Tyr Leu His Trp Val Glu Tyr
            340                 345                 350
Ala Ala Leu His Thr Thr Asn Val Ala Ile Asp Ser Tyr Val Thr
        355                 360                 365
Trp Leu Met Ser Tyr Leu Asn Phe Gln Ile Glu His His Leu Phe Pro
    370                 375                 380
Cys Cys Pro Gln Phe Arg His Pro Ala Ile Ser Ser Arg Val Lys Lys
385                 390                 395                 400
Leu Phe Glu Asp Asn Gly Leu Val Tyr Asp Ala Arg Ser Tyr Val Gln
                405                 410                 415
Ala Leu Lys Asp Thr Phe Gly Asn Leu His Glu Val Gly Val Asn Ala
            420                 425                 430
Gly Gln Ala Ala Lys Ser Glu
        435

<210> SEQ ID NO 32
<211> LENGTH: 1381
<212> TYPE: DNA
<213> ORGANISM: Thraustochytrium aureum

<400> SEQUENCE: 32
ccatgggccg cggcggcgag aaaagcgagg tggaccaggt gcagccacaa aagaccgagc        60
agctccagaa ggccaagtgg gaggatgttg ttcgcatcaa tggagtcgaa tacgacgtca       120
cggactatct cagaaaacac cctggtggca gcgtgatcaa gtacgggctt gccaacaccg       180
gcgctgatgc cacgtccctc tttgaagcgt tccacatgcg ctcaaagaag gctcagatgg       240
tgctcaagtc tctcccaaag cgtgctccgg tcctcgagat ccagccaaac cagcttccag       300
aggagcagac caaggaggcg gagatgctgc gtgatttaa aaaatttgag gatgagattc       360
gccgggatgg attgatggaa ccttccttct ggcatcgcgc ttacagatta tcagagcttg       420
taggtatgtt cacgctcggc ctctacctct tctcgttaaa cactcctctg tctattgctg       480
ctggtgtcct cgtccacggt ctctttggtg cattctgtgg atggtgccag catgaggcag       540
gccacggctc cttttttac agcctttggt ggggcaagcg tgtacaggcc atgttgatcg       600
ggtttggtct aggaacatcc ggcgacatgt ggaacatgat gcacaacaag catcatgctg       660
ccacccaaaa ggttcatcac gaccttgaca ttgacacaac tccttttgta gctttcttca       720
acactgcatt tgagaaaaac agatggaagg cttttccaa gcttgggtc cgctttcagg       780
ctttcacgtt cattcctgtc accagcggca tgatcgtcat gctgttctgg ctgttttttc       840
tccaccctcg ccgcgtcgtt caaagaaga actttgagga gggttttgg atgctgtcga       900
gccacattgt gcgcacctat ctcttccacc ttgtgaccgg ctgggagagc ctcgctgcat       960
gctaccttgt tgggtattgg gcgtgcatgt gggtgtccgg tatgtatttg tttggccact      1020
tttcgctctc ccacactcat atggacattg tggaggcgga cgtgcataag aactgggtca      1080
ggtacgctgt tgaccacact gttgacatca gccatccaa cccgctcgtg tgctgggtca      1140
tgggttacct caacatgcag accatccacc acttgtggcc tgccatgccc cagtaccacc      1200
```

-continued

```
aggtcgaggt ctcacgccgc tttgccatct tcgccaaaaa acacggcctc aactaccgcg    1260
tcgtctctta ctttgaggct tggcgcctga tgctccaaaa tcttgctgac gtcggttccc    1320
actaccatga gaacggtgtc aagcgcgccc caaagaaagc caaggcgcag tagaaagcta    1380
t                                                                    1381
```

<210> SEQ ID NO 33
<211> LENGTH: 456
<212> TYPE: PRT
<213> ORGANISM: Thraustochytrium aureum

<400> SEQUENCE: 33

```
Met Gly Arg Gly Gly Glu Lys Ser Glu Val Asp Gln Val Gln Pro Gln
  1               5                  10                  15

Lys Thr Glu Gln Leu Gln Lys Ala Lys Trp Glu Asp Val Val Arg Ile
             20                  25                  30

Asn Gly Val Glu Tyr Asp Val Thr Asp Tyr Leu Arg Lys His Pro Gly
         35                  40                  45

Gly Ser Val Ile Lys Tyr Gly Leu Ala Asn Thr Gly Ala Asp Ala Thr
     50                  55                  60

Ser Leu Phe Glu Ala Phe His Met Arg Ser Lys Lys Ala Gln Met Val
 65                  70                  75                  80

Leu Lys Ser Leu Pro Lys Arg Ala Pro Val Leu Glu Ile Gln Pro Asn
                 85                  90                  95

Gln Leu Pro Glu Glu Gln Thr Lys Glu Ala Glu Met Leu Arg Asp Phe
            100                 105                 110

Lys Lys Phe Glu Asp Glu Ile Arg Arg Asp Gly Leu Met Glu Pro Ser
        115                 120                 125

Phe Trp His Arg Ala Tyr Arg Leu Ser Glu Leu Val Gly Met Phe Thr
    130                 135                 140

Leu Gly Leu Tyr Leu Phe Ser Leu Asn Thr Pro Leu Ser Ile Ala Ala
145                 150                 155                 160

Gly Val Leu Val His Gly Leu Phe Gly Ala Phe Cys Gly Trp Cys Gln
                165                 170                 175

His Glu Ala Gly His Gly Ser Phe Phe Tyr Ser Leu Trp Trp Gly Lys
            180                 185                 190

Arg Val Gln Ala Met Leu Ile Gly Phe Gly Leu Gly Thr Ser Gly Asp
        195                 200                 205

Met Trp Asn Met Met His Asn Lys His His Ala Ala Thr Gln Lys Val
    210                 215                 220

His His Asp Leu Asp Ile Asp Thr Thr Pro Phe Val Ala Phe Phe Asn
225                 230                 235                 240

Thr Ala Phe Glu Lys Asn Arg Trp Lys Gly Phe Ser Lys Ala Trp Val
                245                 250                 255

Arg Phe Gln Ala Phe Thr Phe Ile Pro Val Thr Ser Gly Met Ile Val
            260                 265                 270

Met Leu Phe Trp Leu Phe Phe Leu His Pro Arg Arg Val Val Gln Lys
        275                 280                 285

Lys Asn Phe Glu Glu Gly Phe Trp Met Leu Ser Ser His Ile Val Arg
    290                 295                 300

Thr Tyr Leu Phe His Leu Val Thr Gly Trp Glu Ser Leu Ala Ala Cys
305                 310                 315                 320

Tyr Leu Val Gly Tyr Trp Ala Cys Met Trp Val Ser Gly Met Tyr Leu
                325                 330                 335
```

| | | | | | | | | | | | | |
|---|---|---|---|---|---|---|---|---|---|---|---|---|
|Phe|Gly|His|Phe|Ser|Leu|Ser|His|Thr|His|Met|Asp|Ile|Val|Glu|Ala|
| | | |340| | | |345| | | |350| |
|Asp|Val|His|Lys|Asn|Trp|Val|Arg|Tyr|Ala|Val|Asp|His|Thr|Val|Asp|
| | | |355| | | |360| | | |365| |
|Ile|Ser|Pro|Ser|Asn|Pro|Leu|Val|Cys|Trp|Val|Met|Gly|Tyr|Leu|Asn|
| | | |370| | | |375| | | |380| |
|Met|Gln|Thr|Ile|His|His|Leu|Trp|Pro|Ala|Met|Pro|Gln|Tyr|His|Gln|
|385| | | | |390| | | | |395| | | | |400|
|Val|Glu|Val|Ser|Arg|Arg|Phe|Ala|Ile|Phe|Ala|Lys|Lys|His|Gly|Leu|
| | | |405| | | |410| | | |415| |
|Asn|Tyr|Arg|Val|Val|Ser|Tyr|Phe|Glu|Ala|Trp|Arg|Leu|Met|Leu|Gln|
| | | |420| | | |425| | | |430| |
|Asn|Leu|Ala|Asp|Val|Gly|Ser|His|Tyr|His|Glu|Asn|Gly|Val|Lys|Arg|
| | | |435| | | |440| | | |445| |
|Ala|Pro|Lys|Lys|Ala|Lys|Ala|Gln|
| | | |450| | | |455|

<210> SEQ ID NO 34
<211> LENGTH: 1329
<212> TYPE: DNA
<213> ORGANISM: Isochrysis galbana

<400> SEQUENCE: 34

```
atggtggcag gcaaatcagg cgctgcggcg cacgtgactc acagctcgac attgccccgt     60
gagtaccatg gcgcgaccaa cgactcgcgc tctgaggcgg ccgacgtcac cgtctctagc    120
atcgatgctg aaaaggagat gatcatcaac ggccgcgtgt atgacgtgtc gtcatttgtg    180
aagcggcacc caggtggctc ggtgatcaag ttccagctgg cgccgacgc gagcgacgcg     240
tacaacaact tcacgtccg ctccaagaag gcggacaaga tgctgtattc gctcccgtcc     300
cggccggccg aggccggcta cgcccaggac gacatctccc gcgactttga aagctgcgc    360
ctcgagctga aggaggaggg ctacttcgag cccaacctgg tgcacgtgag ctacaggtgt    420
gtggaggttc ttgccatgta ctgggctggc gtccagctca tctggtccgg gtactggttc    480
ctcggcgcga tcgtggccgg cattgcgcag ggccgctgcg gctggctcca gcatgagggt    540
gggcactact cgctcaccgg caacatcaag atcgaccggc atctgcagat ggccatctat    600
gggcttggct gcggcatgtc gggctgctac tggcgcaacc agcacaacaa gcaccacgcc    660
acgccgcaga gctcgggac cgaccccgac ctgcagacga tgccgctggt ggccttccac    720
aagatcgtcg gcgccaaggc gcgaggcaag ggcaaggcgt ggctggcgtg caggcgccg    780
ctcttctttg gcgggatcat ctgctcgctc gtctctttcg gctggcagtt cgtgctccac    840
cccaaccacg cgctgcgcgt gcacaatcac ctggagctcg cgtacatggg cctgcggtac    900
gtgctgtggc acctggcctt tggccacctc gggctgctga gctcgctccg cctgtacgcc    960
ttttacgtgg ccgtgggcgg cacctacatc ttcaccaact cgccgtctc gcacacccac   1020
aaggacgtcg tcccgcccac caagcacatc tcgtgggcac tctactcggc caaccacacg   1080
accaactgct ccgactcgcc ctttgtcaac tggtggatgg cctacctcaa cttccagatc   1140
gagcaccacc tcttcccgtc gatgccgcag tacaaccacc ccaagatcgc ccgcgggtg    1200
cgcgcgctct tcgagaagca cggggtcgag tatgacgtcc ggccataact ggagtgtttt   1260
cgggtcacgt acgtcaacct gctcgccgta ggcaacccgg agcactccta ccacgagcac   1320
acgcactag                                                           1329
```

<210> SEQ ID NO 35
<211> LENGTH: 442
<212> TYPE: PRT
<213> ORGANISM: Isochrysis galbana

<400> SEQUENCE: 35

```
Met Val Ala Gly Lys Ser Gly Ala Ala His Val Thr His Ser Ser
 1               5                  10                  15

Thr Leu Pro Arg Glu Tyr His Gly Ala Thr Asn Asp Ser Arg Ser Glu
            20                  25                  30

Ala Ala Asp Val Thr Val Ser Ser Ile Asp Ala Glu Lys Glu Met Ile
        35                  40                  45

Ile Asn Gly Arg Val Tyr Asp Val Ser Ser Phe Val Lys Arg His Pro
    50                  55                  60

Gly Gly Ser Val Ile Lys Phe Gln Leu Gly Ala Asp Ala Ser Asp Ala
65                  70                  75                  80

Tyr Asn Asn Phe His Val Arg Ser Lys Lys Ala Asp Lys Met Leu Tyr
                85                  90                  95

Ser Leu Pro Ser Arg Pro Ala Glu Ala Gly Tyr Ala Gln Asp Asp Ile
            100                 105                 110

Ser Arg Asp Phe Glu Lys Leu Arg Leu Glu Leu Lys Glu Glu Gly Tyr
        115                 120                 125

Phe Glu Pro Asn Leu Val His Val Ser Tyr Arg Cys Val Glu Val Leu
    130                 135                 140

Ala Met Tyr Trp Ala Gly Val Gln Leu Ile Trp Ser Gly Tyr Trp Phe
145                 150                 155                 160

Leu Gly Ala Ile Val Ala Gly Ile Ala Gln Gly Arg Cys Gly Trp Leu
                165                 170                 175

Gln His Glu Gly Gly His Tyr Ser Leu Thr Gly Asn Ile Lys Ile Asp
            180                 185                 190

Arg His Leu Gln Met Ala Ile Tyr Gly Leu Gly Cys Gly Met Ser Gly
        195                 200                 205

Cys Tyr Trp Arg Asn Gln His Asn Lys His His Ala Thr Pro Gln Lys
    210                 215                 220

Leu Gly Thr Asp Pro Asp Leu Gln Thr Met Pro Leu Val Ala Phe His
225                 230                 235                 240

Lys Ile Val Gly Ala Lys Ala Arg Gly Lys Gly Lys Ala Trp Leu Ala
                245                 250                 255

Trp Gln Ala Pro Leu Phe Phe Gly Gly Ile Ile Cys Ser Leu Val Ser
            260                 265                 270

Phe Gly Trp Gln Phe Val Leu His Pro Asn His Ala Leu Arg Val His
        275                 280                 285

Asn His Leu Glu Leu Ala Tyr Met Gly Leu Arg Tyr Val Leu Trp His
    290                 295                 300

Leu Ala Phe Gly His Leu Gly Leu Leu Ser Ser Leu Arg Leu Tyr Ala
305                 310                 315                 320

Phe Tyr Val Ala Val Gly Gly Thr Tyr Ile Phe Thr Asn Phe Ala Val
                325                 330                 335

Ser His Thr His Lys Asp Val Val Pro Pro Thr Lys His Ile Ser Trp
            340                 345                 350

Ala Leu Tyr Ser Ala Asn His Thr Thr Asn Cys Ser Asp Ser Pro Phe
        355                 360                 365

Val Asn Trp Trp Met Ala Tyr Leu Asn Phe Gln Ile Glu His His Leu
    370                 375                 380
```

```
Phe Pro Ser Met Pro Gln Tyr Asn His Pro Lys Ile Ala Pro Arg Val
385                 390                 395                 400

Arg Ala Leu Phe Glu Lys His Gly Val Glu Tyr Asp Val Arg Pro Tyr
            405                 410                 415

Leu Glu Cys Phe Arg Val Thr Tyr Val Asn Leu Leu Ala Val Gly Asn
        420                 425                 430

Pro Glu His Ser Tyr His Glu His Thr His
        435                 440
```

<210> SEQ ID NO 36
<211> LENGTH: 36
<212> TYPE: DNA
<213> ORGANISM: Artificial Sequence
<220> FEATURE:
<223> OTHER INFORMATION: Primer RO838
<220> FEATURE:
<221> NAME/KEY: misc_feature
<222> LOCATION: (7)...(7)
<223> OTHER INFORMATION: v = a or g or c at position 7
<220> FEATURE:
<221> NAME/KEY: misc_feature
<222> LOCATION: (10)...(10)
<223> OTHER INFORMATION: r = g or a at position 10
<220> FEATURE:
<221> NAME/KEY: misc_feature
<222> LOCATION: (13)...(13)
<223> OTHER INFORMATION: s = g or c at position 13
<220> FEATURE:
<221> NAME/KEY: misc_feature
<222> LOCATION: (16)...(16)
<223> OTHER INFORMATION: r = g or a at position 16
<220> FEATURE:
<221> NAME/KEY: misc_feature
<222> LOCATION: (19)...(19)
<223> OTHER INFORMATION: r = g or a at position 19
<220> FEATURE:
<221> NAME/KEY: misc_feature
<222> LOCATION: (22)...(22)
<223> OTHER INFORMATION: y = t/u or c at position 22
<220> FEATURE:
<221> NAME/KEY: misc_feature
<222> LOCATION: (25)...(25)
<223> OTHER INFORMATION: r = g or a at position 25
<220> FEATURE:
<221> NAME/KEY: misc_feature
<222> LOCATION: (31)...(31)
<223> OTHER INFORMATION: r = g or a at position 31

<400> SEQUENCE: 36
catggtvggr aasagrtgrt gytcratctg rtagtt                              36

<210> SEQ ID NO 37
<211> LENGTH: 25
<212> TYPE: DNA
<213> ORGANISM: Artificial Sequence
<220> FEATURE:
<223> OTHER INFORMATION: Primer RO1065

<400> SEQUENCE: 37
cgacaagagg aagagtgtcc aaatc                                          25

<210> SEQ ID NO 38
<211> LENGTH: 30
<212> TYPE: DNA
<213> ORGANISM: Artificial Sequence
<220> FEATURE:
<223> OTHER INFORMATION: Primer RO1064

<400> SEQUENCE: 38
cgccttcaag agtttttgta cggaattggg                                     30

<210> SEQ ID NO 39
<211> LENGTH: 30
<212> TYPE: DNA
<213> ORGANISM: Artificial Sequence
<220> FEATURE:
<223> OTHER INFORMATION: Primer RO1097

<400> SEQUENCE: 39
cttgtaccat gggtcgcgga gcacagggag                                              30

<210> SEQ ID NO 40
<211> LENGTH: 30
<212> TYPE: DNA
<213> ORGANISM: Artificial Sequence
<220> FEATURE:
<223> OTHER INFORMATION: Primer RO1098

<400> SEQUENCE: 40
tgaagcttac tcgctcttgg cagcttggcc                                              30

<210> SEQ ID NO 41
<211> LENGTH: 30
<212> TYPE: DNA
<213> ORGANISM: Artificial Sequence
<220> FEATURE:
<223> OTHER INFORMATION: Primer RO1107

<400> SEQUENCE: 41
tttaaccatg ggccgcggcg gcgagaaaag                                              30

<210> SEQ ID NO 42
<211> LENGTH: 36
<212> TYPE: DNA
<213> ORGANISM: Artificial Sequence
<220> FEATURE:
<223> OTHER INFORMATION: Primer RO1108

<400> SEQUENCE: 42
gggaagaagc tttctactgc gccttggctt tctttg                                       36

<210> SEQ ID NO 43
<211> LENGTH: 26
<212> TYPE: DNA
<213> ORGANISM: Artificial Sequence
<220> FEATURE:
<223> OTHER INFORMATION: Primer RO1235

<400> SEQUENCE: 43
cgaagttggt gaagatgtag gtgccg                                                  26

<210> SEQ ID NO 44
<211> LENGTH: 27
<212> TYPE: DNA
<213> ORGANISM: Artificial Sequence
<220> FEATURE:
<223> OTHER INFORMATION: Primer RO1232

<400> SEQUENCE: 44
gagcgacgcg tacaacaact ttcacgt                                                 27

<210> SEQ ID NO 45
<211> LENGTH: 23
<212> TYPE: DNA
<213> ORGANISM: Artificial Sequence
<220> FEATURE:

<223> OTHER INFORMATION: Primer

<400> SEQUENCE: 45
cgactggagc acgaggacac tga                 23

<210> SEQ ID NO 46
<211> LENGTH: 25
<212> TYPE: DNA
<213> ORGANISM: Artificial Sequence
<220> FEATURE:
<223> OTHER INFORMATION: GeneRacer 3 Prime Primer

<400> SEQUENCE: 46
gctgtcaacg atacgctacg taacg                 25

<210> SEQ ID NO 47
<211> LENGTH: 26
<212> TYPE: DNA
<213> ORGANISM: Artificial Sequence
<220> FEATURE:
<223> OTHER INFORMATION: Nested Primer RO1234

<400> SEQUENCE: 47
agctccaggt gattgtgcac gcgcag                 26

<210> SEQ ID NO 48
<211> LENGTH: 27
<212> TYPE: DNA
<213> ORGANISM: Artificial Sequence
<220> FEATURE:
<223> OTHER INFORMATION: Primer RO1233

<400> SEQUENCE: 48
gactttgaga agctgcgcct cgagctg                 27

<210> SEQ ID NO 49
<211> LENGTH: 26
<212> TYPE: DNA
<213> ORGANISM: Artificial Sequence
<220> FEATURE:
<223> OTHER INFORMATION: Nested 5 Prime Primer

<400> SEQUENCE: 49
ggacactgac atggactgaa ggagta                 26

<210> SEQ ID NO 50
<211> LENGTH: 23
<212> TYPE: DNA
<213> ORGANISM: Artificial Sequence
<220> FEATURE:
<223> OTHER INFORMATION: Nested 3 Prime Primer

<400> SEQUENCE: 50
cgctacgtaa cggcatgaca gtg                 23

<210> SEQ ID NO 51
<211> LENGTH: 35
<212> TYPE: DNA
<213> ORGANISM: Artificial Sequence
<220> FEATURE:
<223> OTHER INFORMATION: Primer RO1309

<400> SEQUENCE: 51
atgatggaat tcatggtggc aggcaaatca ggcgc                 35

```
<210> SEQ ID NO 52
<211> LENGTH: 35
<212> TYPE: DNA
<213> ORGANISM: Artificial Sequence
<220> FEATURE:
<223> OTHER INFORMATION: Primer RO1310

<400> SEQUENCE: 52
aataatgtcg acctagtgcg tgtgctcgtg gtagg                              35

<210> SEQ ID NO 53
<211> LENGTH: 14
<212> TYPE: PRT
<213> ORGANISM: Artificial Sequence
<220> FEATURE:
<223> OTHER INFORMATION: Consensus Peptide Sequence

<400> SEQUENCE: 53

Val Tyr Asp Val Thr Glu Trp Val Lys Arg His Pro Gly Gly
 1               5                  10

<210> SEQ ID NO 54
<211> LENGTH: 15
<212> TYPE: PRT
<213> ORGANISM: Artificial Sequence
<220> FEATURE:
<223> OTHER INFORMATION: Consensus Peptide Sequence

<400> SEQUENCE: 54

Gly Ala Ser Ala Asn Trp Trp Lys His Gln His Asn Val His His
 1               5                  10                  15

<210> SEQ ID NO 55
<211> LENGTH: 12
<212> TYPE: PRT
<213> ORGANISM: Artificial Sequence
<220> FEATURE:
<223> OTHER INFORMATION: Consensus Peptide Sequence

<400> SEQUENCE: 55

Asn Tyr Gln Ile Glu His His Leu Phe Pro Thr Met
 1               5                  10
```